(12) United States Patent
Slukvin et al.

(10) Patent No.: US 10,982,192 B2
(45) Date of Patent: Apr. 20, 2021

(54) METHOD FOR THE INDUCTION OF ARTERIAL-TYPE OF HEMOGENIC ENDOTHELIUM FROM HPSCS

(71) Applicant: Wisconsin Alumni Research Foundation, Madison, WI (US)

(72) Inventors: Igor I. Slukvin, Verona, WI (US); Gene Uenishi, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 51 days.

(21) Appl. No.: 15/932,317

(22) Filed: Feb. 16, 2018

(65) Prior Publication Data

US 2018/0291349 A1   Oct. 11, 2018

Related U.S. Application Data

(60) Provisional application No. 62/460,348, filed on Feb. 17, 2017.

(51) Int. Cl.
| | |
|---|---|
| *C12N 11/02* | (2006.01) |
| *C12N 5/071* | (2010.01) |
| *C12N 5/0789* | (2010.01) |
| *C07K 16/28* | (2006.01) |
| *C12N 5/074* | (2010.01) |
| *C12N 5/0735* | (2010.01) |
| *C07K 16/00* | (2006.01) |

(52) U.S. Cl.
CPC .......... *C12N 5/0691* (2013.01); *C07K 16/00* (2013.01); *C07K 16/28* (2013.01); *C12N 5/0606* (2013.01); *C12N 5/0647* (2013.01); *C12N 5/0696* (2013.01); *C12N 11/02* (2013.01); *C07K 2317/52* (2013.01); *C07K 2319/30* (2013.01); *C07K 2319/32* (2013.01); *C12N 2500/99* (2013.01); *C12N 2501/42* (2013.01); *C12N 2506/02* (2013.01); *C12N 2506/45* (2013.01); *C12N 2533/50* (2013.01); *C12N 2533/90* (2013.01)

(58) Field of Classification Search
None
See application file for complete search history.

(56) References Cited

PUBLICATIONS

Aylon (Leukemia, 29: 1741-1753, 2015) (Year: 2015).*
Boiers (Cell Stem Cell 13, 535-548, Nov. 7, 2013). (Year: 2013).*
Kumano, K. et al. Notch1 but not Notch2 is essential for generating hematopoietic stem cells from endothelial cells. Immunity 18, 699-711 (2003).
Lahoud, M.H. et al. Gene targeting of Desrt, a novel ARID class DNA-binding protein, causes growth retardation and abnormal development of reproductive organs. Genome Res 11, 1327-1334 (2001).
Langmead, B., Trapnell, C., Pop, M. & Salzberg, S.L. Ultrafast and memory-efficient alignment of short DNA sequences to the human genome. Genome Biol 10, R25 (2009).
Lawson, N.D. et al. Notch signaling is required for arterial-venous differentiation during embryonic vascular development. Development 128, 3675-3683 (2001).
Lawson, N.D., Vogel, A.M. & Weinstein, B.M. sonic hedgehog and vascular endothelial growth factor act upstream of the Notch pathway during arterial endothelial differentiation. Dev Cell 3, 127-136 (2002).
Ledran, M.H. et al. Efficient hematopoietic differentiation of human embryonic stem cells on stromal cells derived from hematopoietic niches. Cell Stem Cell 3, 85-98. (2008).
Lee, J.B. et al. Notch-HES1 signaling axis controls hematoendothelial fate decisions of human embryonic and induced pluripotent stem cells. Blood 122, 1162-1173 (2013).
Leng, N. et al. EBSeq: an empirical Bayes hierarchical model for inference in RNA-seq experiments. Bioinformatics 29, 1035-1043 (2013).
Li, B., Ruotti, V., Stewart, R.M., Thomson, J.A. & Dewey, C.N. RNA-Seq gene expression estimation with read mapping uncertainty. Bioinformatics 26, 493-500 (2010).
Li, B. & Dewey, C.N. RSEM: accurate transcript quantification from RNA-Seq data with or without a reference genome. BMC Bioinformatics 12, 323 (2011).
Li, Y. et al. Inflammatory signaling regulates embryonic hematopoietic stem and progenitor cell production. Genes Dev 28, 2597-2612 (2014).
Lizama, C.O. et al. Repression of arterial genes in hemogenic endothelium is sufficient for haematopoietic fate acquisition. Nat Commun 6, 7739 (2015).
Lu, YF., et al. (2016) Engineered Murine HSCs Reconstitute Multi-lineage Hematopoiesis and Adaptive Immunity. Cell Report 17, 3178-3192.
Manna, S. et al. Histone H3 Lysine 27 demethylases Jmjd3 and Utx are required for T-cell differentiation. Nat Commun 6, 8152 (2015).
Medvinsky, A., et al. Embryonic origin of the adult hematopoietic system: advances and questions. Development 138, 1017-1031 (2011).
Monteiro, R. et al. Transforming Growth Factor beta Drives Hemogenic Endothelium Programming and the Transition to Hematopoietic Stem Cells. Dev Cell (2016).
Moskvin, O.V., McIlwain, S. & Ong, I.M. Camda 2014: Making sense of RNA-Seq data: from low-level processing to functional analysis. . Systems Biomedicine 2, 31-40 (2014).
Nakagawa, M. et al. AML1/Runx1 rescues Notch1-null mutation-induced deficiency of para-aortic splanchnopleural hematopoiesis. Blood 108, 3329-3334 (2006).
NG, C.E. et al. A Runx1 intronic enhancer marks hemogenic endothelial cells and hematopoietic stem cells. Stem Cells 28, 1869-1881 (2010).
NG, E.S. et al. Differentiation of human embryonic stem cells to HOXA+ hemogenic vasculature that resembles the aorta-gonad-mesonephros. Nat Biotechnol (2016).

(Continued)

*Primary Examiner* — Anoop K Singh
*Assistant Examiner* — Magdalene K Sgagias
(74) *Attorney, Agent, or Firm* — Quarles & Brady LLP

(57) ABSTRACT

This invention discloses a method for the induction of arterial-type of hemogenic endothelium.

9 Claims, 34 Drawing Sheets
(15 of 34 Drawing Sheet(s) Filed in Color)
Specification includes a Sequence Listing.

(56) References Cited

PUBLICATIONS

North, T. et al. Cbfa2 is required for the formation of intra-aortic hematopoietic clusters. Development 126, 2563-2575 (1999).

North, T.E. et al. Hematopoietic stem cell development is dependent on blood flow. Cell 137, 736-748 (2009).

Nottingham, W.T. et al. Runx1-mediated hematopoietic stem-cell emergence is controlled by a Gata/Ets/SCL-regulated enhancer. Blood 110, 4188-4197 (2007).

Ohishi, K., Varnum-Finney, B. & Bernstein, I.D. Delta-1 enhances marrow and thymus repopulating ability of human CD34(+)CD38(-) cord blood cells. J Clin Invest 110, 1165-1174 (2002).

Rahman, N. et al. Engineering the haemogenic niche mitigates endogenous inhibitory signals and controls pluripotent stem cell-derived blood emergence. Nat Commun 8, 15380 (2017).

Redecke, V. et al. Hematopoietic progenitor cell lines with myeloid and lymphoid potential. Nat Methods 10, 795-803 (2013).

Richard, C. et al. Endothelio-mesenchymal interaction controls runx1 expression and modulates the notch pathway to initiate aortic hematopoiesis. Dev Cell 24, 600-611 (2013).

Robert-Moreno, A., Espinosa, L., de la Pompa, J.L. & Bigas, A. RBPjkappa-dependent Notch function regulates Gata2 and is essential for the formation of intra-embryonic hematopoietic cells. Development 132, 1117-1126 (2005).

Robert-Moreno, A. et al. Impaired embryonic haematopoiesis yet normal arterial development in the absence of the Notch ligand Jagged1. EMBO J 27, 1886-1895 (2008).

Rybtsov, S., Ivanovs, A., Zhao, S. & Medvinsky, A. Concealed expansion of immature precursors underpins acute burst of adult HSC activity in foetal liver. Development 143, 1284-1289 (2016).

Sato, T. et al. Evi-1 promotes para-aortic splanchnopleural hematopoiesis through up-regulation of GATA-2 and repression of TGF-b signaling. Cancer Sci 99, 1407-1413 (2008).

Shannon, P. et al. Cytoscape: a software environment for integrated models of biomolecular interaction networks. Genome Res 13, 2498-2504 (2003).

Shojaei, F. et al. Hierarchical and ontogenic positions serve to define the molecular basis of human hematopoietic stem cell behavior. Dev Cell 8, 651-663. (2005).

Slukvin, II Generating human hematopoietic stem cells in vitro—exploring endothelial to hematopoietic transition as a portal for sternness acquisition. FEBS Lett (2016).

Souihol, C. et al. Inductive interactions mediated by interplay of asymmetric signalling underlie development of adult haematopoietic stem cells. Nat Commun 7, 10784 (2016).

Sprinzak, D. et al. Cis-interactions between Notch and Delta generate mutually exclusive signalling states. Nature 465, 86-90 (2010).

Sugimura, R. et al. Haematopoietic stem and progenitor cells from human pluripotent stem cells. Nature 545, 432-438 (2017).

Swiers, G. et al. Early dynamic fate changes in haemogenic endothelium characterized at the single-cell level. Nat Commun 4, 2924 (2013).

Tamplin, O.J. et al. Hematopoietic stem cell arrival triggers dynamic remodeling of the perivascular niche. Cell 160, 241-252 (2015).

Taoudi, S. et al. ERG dependence distinguishes developmental control of hematopoietic stem cell maintenance from hematopoietic specification. Genes Dev 25, 251-262 (2011).

Thambyrajiah, R. et al. GFI1 proteins orchestrate the emergence of haematopoietic stem cells through recruitment of LSD1. Nat Cell Biol 18, 21-32 (2016).

Jenishi, G. et al. Tenascin C promotes hematoendothelial development and T lymphoid commitment from human pluripotent stem cells in chemically defined conditions. Stem cell reports 3, 1073-1084 (2014).

Vodyanik, Maxim A., et al. "Human embryonic stem cell—derived CD34+ cells: efficient production in the coculture with OP9 stromal cells and analysis of lymphohematopoietic potential." Blood 105.2 (2005): 617-626.

Vodyanik, M.A. et al. Hematoendothelial differentiation of human embryonic stem cells. Current protocols in cell biology / editorial board, Juan S. Bonifacino . . . [et al.] Chapter 23, Unit 23.26 (2007).

Wang, L. et al. Generation of hematopoietic repopulating cells from human embryonic stem cells independent of ectopic HOXB4 expression. J Exp Med 201, 1603-1614. Epub May 2005 1609. (2005).

Yzaguirre, A.D. & Speck, N.A. Insights into blood cell formation from hemogenic endothelium in lesser-known anatomic sites. Dev Dyn (2016).

Zhang, W.J., Park, C., Arentson, E. & Choi, K. Modulation of hematopoietic and endothelial cell differentiation from mouse embryonic stem cells by different culture conditions. Blood 105, 111-114. Epub 2004 Jul 2001. (2005).

Rowe, et al. Engineering Hematopoietic Stem Cells: Lessons from Development, Cell Stem Cell. Jun. 2, 2016; 18(6): 707-720.

Seita, et al. Hematopoietic Stem Cell: Self-renewal versus Differentiation, Wiley Interdiscip Rev Syst Biol Med. 2010 ; 2(6): 640-653.

Vizcardo, et al. Regeneration of Human Tumor Antigen-Specific T Cells from iPSCs Derived from Mature CD8+ T Cells, Cell Stem Cell 12, 31-36, Jan. 3, 2013.

Ayllon, V. et al. The Notch ligand DLL4 specifically marks human hematoendothelial progenitors and regulates their hematopoietic fate. Leukemia 29, 1741-1753 (2015).

Barnes, R.M., et al. Analysis of the Hand1 cell lineage reveals novel contributions to cardiovascular, neural crest, extra-embryonic, and lateral mesoderm derivatives. Dev Dyn 239, 3086-3097 (2010).

Basecke, J. et al. AML1/ETO promotes the maintenance of early hematopoietic progenitors in NOD/SCID mice but does not abrogate their lineage specific differentiation. Leuk Lymphoma 46, 265-272 (2005).

Bee, T. et al. The mouse Runx1 +23 hematopoietic stem cell enhancer confers hematopoietic specificity to both Runx1 promoters. Blood 113, 5121-5124 (2009).

Beguelin, W. et al. EZH2 and BCL6 Cooperate to Assemble CBX8-BCOR Complex to Repress Bivalent Promoters, Mediate Germinal Center Formation and Lymphomagenesis. Cancer Cell 30, 197-213 (2016).

Bellefroid, E.J. et al. Clustered organization of homologous KRAB zinc-finger genes with enhanced expression in human T lymphoid cells. EMBO J 12, 1363-1374 (1993).

Bertrand, J.Y. et al. Haematopoietic stem cells derive directly from aortic endothelium during development. Nature 464, 108-111 (2010).

Bigas, A., et al. The Notch pathway in hematopoietic stem cells. Curr Top Microbiol Immunol 360, 1-18 (2012).

Bigas, A. & Espinosa, L. Hematopoietic stem cells: to be or Notch to be. Blood 119, 3226-3235 (2012).

Bigas, A., et al. Notch and Wnt signaling in the emergence of hematopoietic stem cells. Blood Cells Mol Dis 51, 264-270 (2013).

Bovolenta, L.A., Acencio, M.L. & Lemke, N. HTRIdb: an open-access database for experimentally verified human transcriptional regulation interactions. BMC Genomics 13, 405 (2012).

Burns, C.E., Traver, D., Mayhall, E., Shepard, J.L. & Zon, L.I. Hematopoietic stem cell fate is established by the Notch-Runx pathway. Genes Dev 19, 2331-2342 (2005).

Burns, C.E. et al. A genetic screen in zebrafish defines a hierarchical network of pathways required for hematopoietic stem cell emergence. Blood 113, 5776-5782 (2009).

Butko, E., Pouget, C., and Traver, D. (2016). Complex regulation of HSC emergence by the Notch signaling pathway. Dev Biol 409, 129-138.

Cahan, P. et al. CellNet: network biology applied to stem cell engineering. Cell 158, 903-915 (2014).

Chanda, B., Ditadi, A., Iscove, N.N. & Keller, G. Retinoic acid signaling is essential for embryonic hematopoietic stem cell development. Cell 155, 215-227 (2013).

Chen, G. et al. Chemically defined conditions for human iPSC derivation and culture. Nat Methods 8, 424-429 (2011).

Choi, K.-D. et al. Identification of the Hemogenic Endothelial Progenitor and Its Direct Precursor in Human Pluripotent Stem Cell Differentiation Cultures. Cell Rep 2, 553-567 (2012).

De Bruijn, M.F., Speck, N.A., Peeters, M.C. & Dzierzak, E. Definitive hematopoietic stem cells first develop within the major arterial regions of the mouse embryo. The EMBO journal 19, 2465-2474 (2000).

(56) References Cited

PUBLICATIONS

Del Alamo, D., et al. Mechanism and significance of cis-inhibition in Notch signalling. Curr Biol 21, R40-47 (2011).
Deng, Y. et al. Endothelial RAF1/ERK activation regulates arterial morphogenesis. Blood 121, 3988-3996, S3981-3989 (2013).
Dias, J. et al. Generation of red blood cells from human induced pluripotent stem cells. Stem Cells Dev 20, 1639-1647 (2011).
Ditadi, A. et al. Human definitive haemogenic endothelium and arterial vascular endothelium represent distinct lineages. Nat Cell Biol 17, 580-591 (2015).
Dou, D.R. et al. Medial HOXA genes demarcate haematopoietic stem cell fate during human development. Nat Cell Biol 18, 595-606 (2016).
Duarte, A. et al. Dosage-sensitive requirement for mouse Dll4 in artery development. Genes Dev 18, 2474-2478 (2004).
Dzierzak, E. et al. Of lineage and legacy: the development of mammalian hematopoietic stem cells. Nat Immunol 9, 129-136 (2008).
Elcheva, I. et al. Direct induction of haematoendothelial programs in human pluripotent stem cells by transcriptional regulators. Nat Commun 5, 4372 (2014).
Gama-Norton, L. et al. Notch signal strength controls cell fate in the haemogenic endothelium. Nat Commun 6, 8510 (2015).
Gerhardt, D.M. et al. The Notch1 transcriptional activation domain is required for development and reveals a novel role for Notch1 signaling in fetal hematopoietic stem cells. Genes Dev 28, 576-593 (2014).
Gering, M. et al.. Hedgehog signaling is required for adult blood stem cell formation in zebrafish embryos. Dev Cell 8, 389-400 (2005).
Ghiaur, G. et al. Regulation of human hematopoietic stem cell self-renewal by the microenvironment's control of retinoic acid signaling. Proc Natl Acad Sci U S A 110, 16121-16126 (2013).
Gordon-Keylock, S., et al. Mouse extraembryonic arterial vessels harbor precursors capable of maturing into lefinitive HSCs. Blood 122, 2338-2345 (2013).
Goyama, S. et al. Evi-1 is a critical regulator for hematopoietic stem cells and transformed leukemic cells. Cell Stem Cell 3, 207-220 (2008).
Guibentif, C. et al. Single-Cell Analysis Identifies Distinct Stages of Human Endothelial-to-Hematopoietic Transition. Cell Rep 19, 10-19 (2017).
Guiu, J. et al. Hes repressors are essential regulators of hematopoietic stem cell development downstream of Notch signaling. J Exp Med 210, 71-84 (2013).
Hadland, B.K. et al. A requirement for Notch1 distinguishes 2 phases of definitive hematopoiesis during development. Blood 104, 3097-3105 (2004).
Hadland, B.K. et al. Endothelium and Notch specify and amplify aorta-gonad-mesonephros-derived hematopoietic stem cells. J Clin Invest 125, 2032-2045 (2015).
Hadland, B.K. et al. A Common Origin for B-1a and B-2 Lymphocytes in Clonal Pre-Hematopoietic Stem Cells. Stem cell reports 8, 1563-1572 (2017).
He, Q. et al. Inflammatory signaling regulates hematopoietic stem and progenitor cell emergence in vertebrates. Blood 125, 1098-1106 (2015).
He, Q. et al. Unexpected role of inflammatory signaling in hematopoietic stem cell development: its role beyond Inflammation. Curr Opin Hematol 23, 18-22 (2016).
Heo, H.R. et al. Hormonal regulation of hematopoietic stem cells and their niche: a focus on estrogen. Int J Stem Cells 8, 18-23 (2015).
Hsu, H.C. et al. Hematopoietic stem cells express Tie-2 receptor in the murine fetal liver. Blood 96, 3757-3762 (2000).
Hu, Y. & Smyth, G.K. Elda: extreme limiting dilution analysis for comparing depleted and enriched populations in stem cell and other assays. J Immunol Methods 347, 70-78 (2009).
Jang, I.H. et al. Notch1 acts via Foxc2 to promote definitive hematopoiesis via effects on hemogenic endothelium. Blood 125, 1418-1426 (2015).
Jokubaistis, V.J. et al. Angiotensin-converting enzyme (CD143) marks hematopoietic stem cells in human embryonic, fetal, and adult hematopoietic tissues. Blood 111, 4055-4063. Epub Nov. 2007 4059. (2008).
Jung, H.S. et al. A human VE-cadherin-tdTomato and CD43-green fluorescent protein dual reporter cell line for study endothelial to hematopoietic transition. Stem Cell Res 17, 401-405 (2016).
Kennedy, M. et al. T lymphocyte potential marks the emergence of definitive hematopoietic progenitors in human pluripotent stem cell differentiation cultures. Cell Rep 2, 1722-1735 (2012).
Kim, P.G. et al. Signaling axis involving Hedgehog, Notch, and Scl promotes the embryonic endothelial-to-hematopoietic transition. Proc Natl Acad Sci U S A 110, E141-150 (2013).
Kim, P.G. et al. Flow-induced protein kinase A-CREB pathway acts via BMP signaling to promote HSC emergence. J Exp Med 212, 633-648 (2015).
Kim, H.R. et al. Improved hematopoietic differentiation of human pluripotent stem cells via estrogen receptor signaling pathway. Cell Biosci 6, 50 (2016).

* cited by examiner

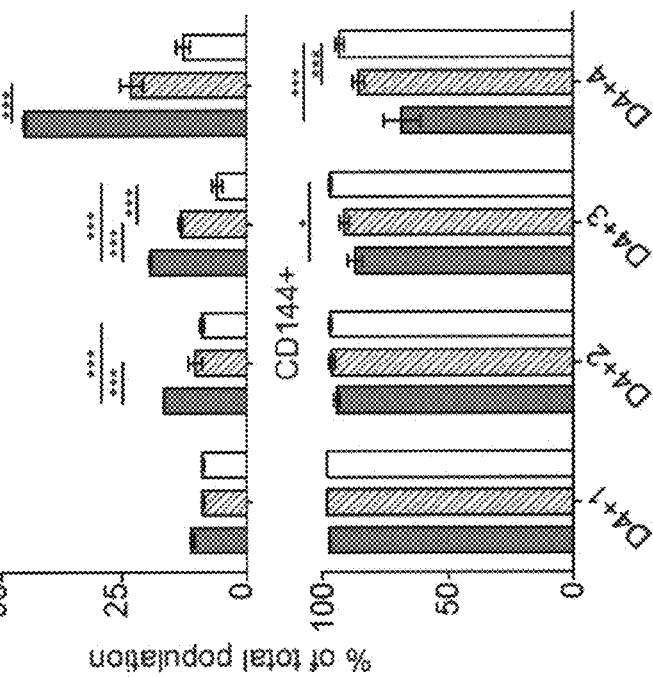
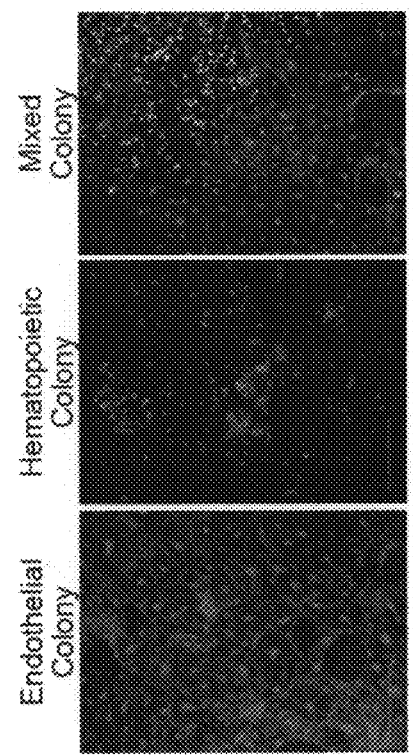
FIGS. 2A-2G CONTINUED

FIGS. 4A-4E CONTINUED
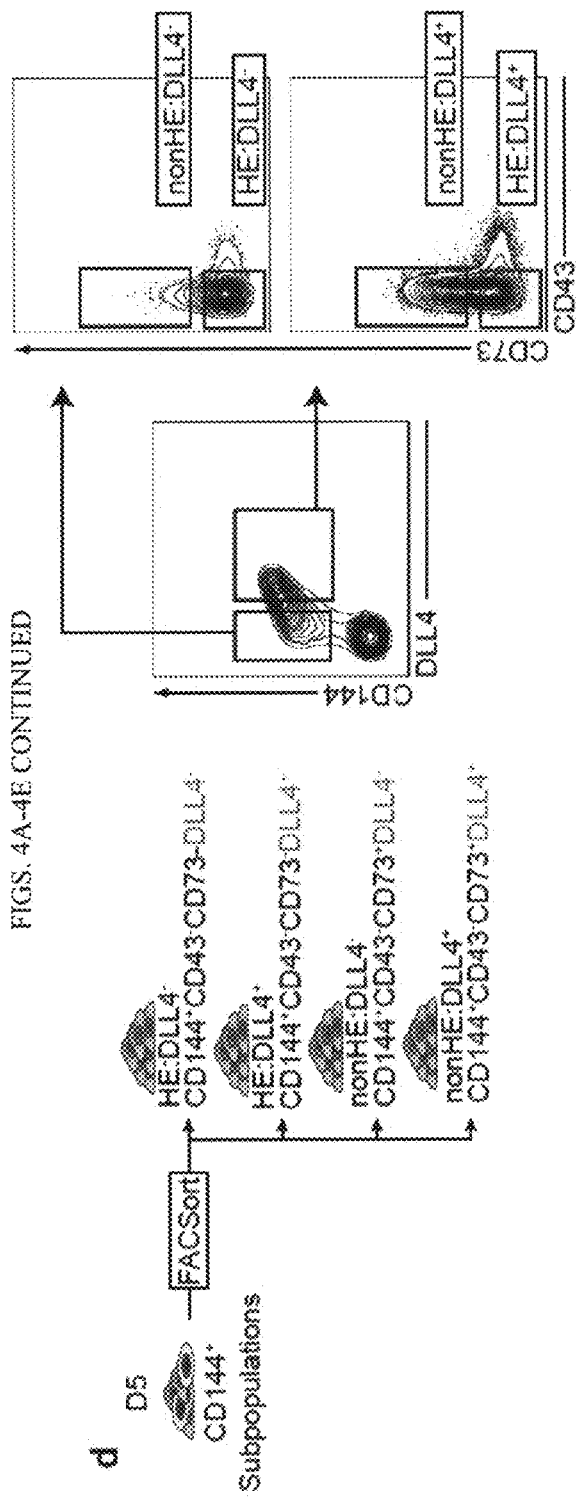
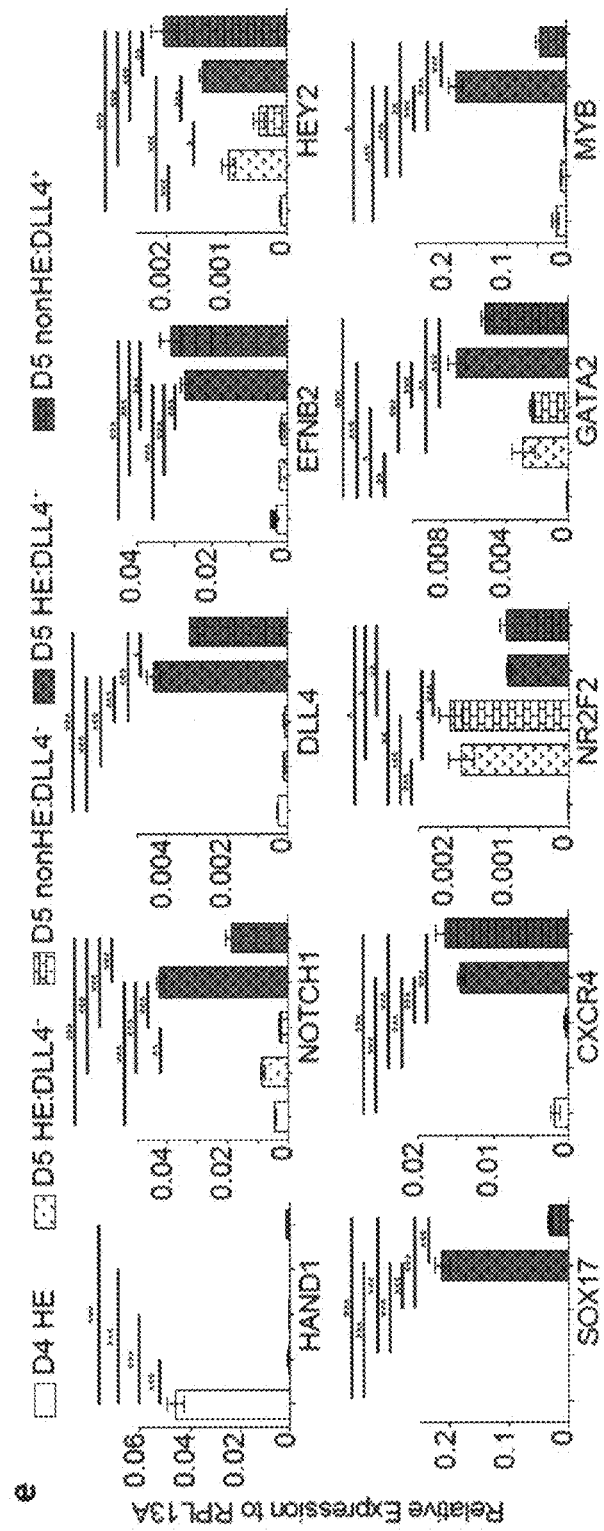

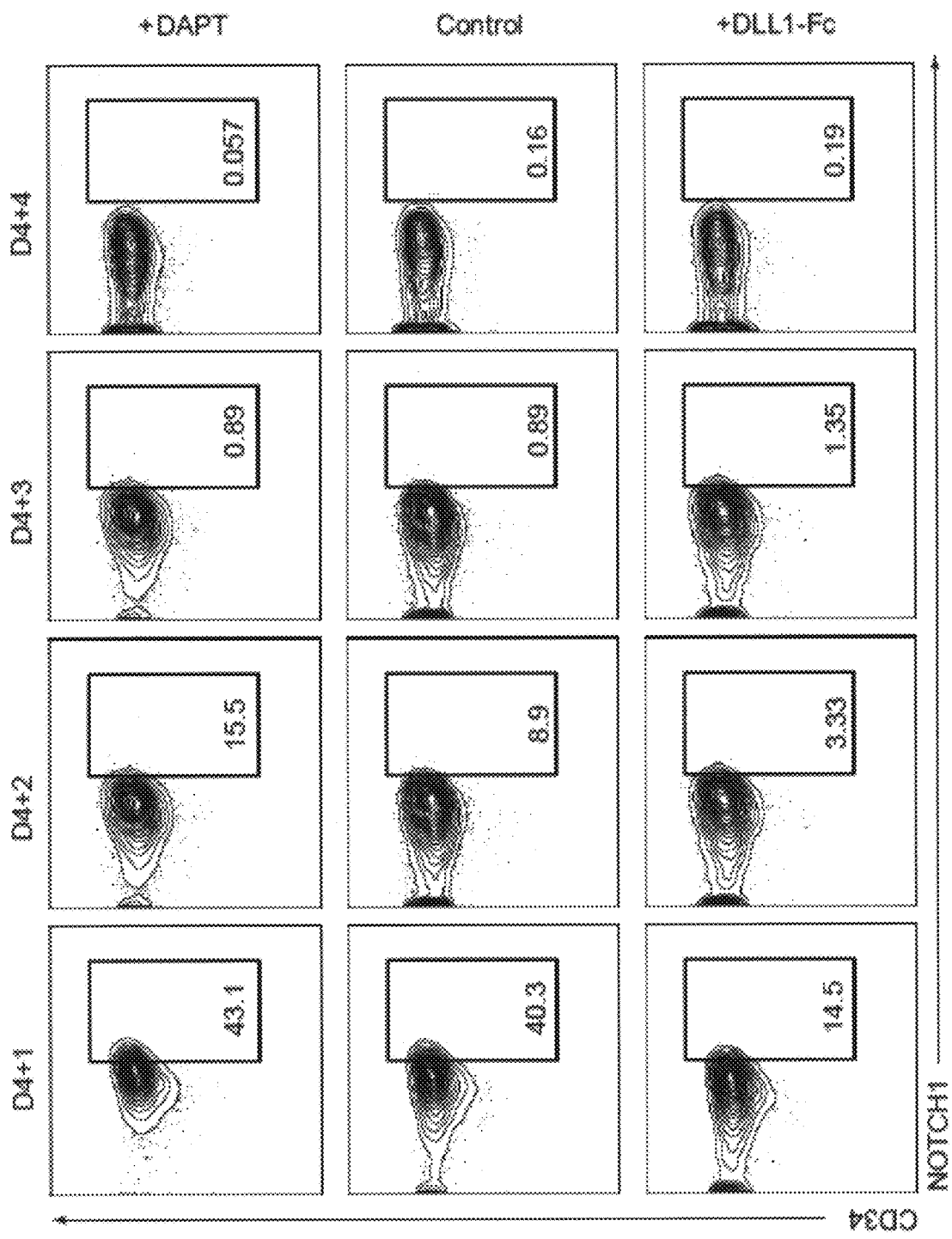

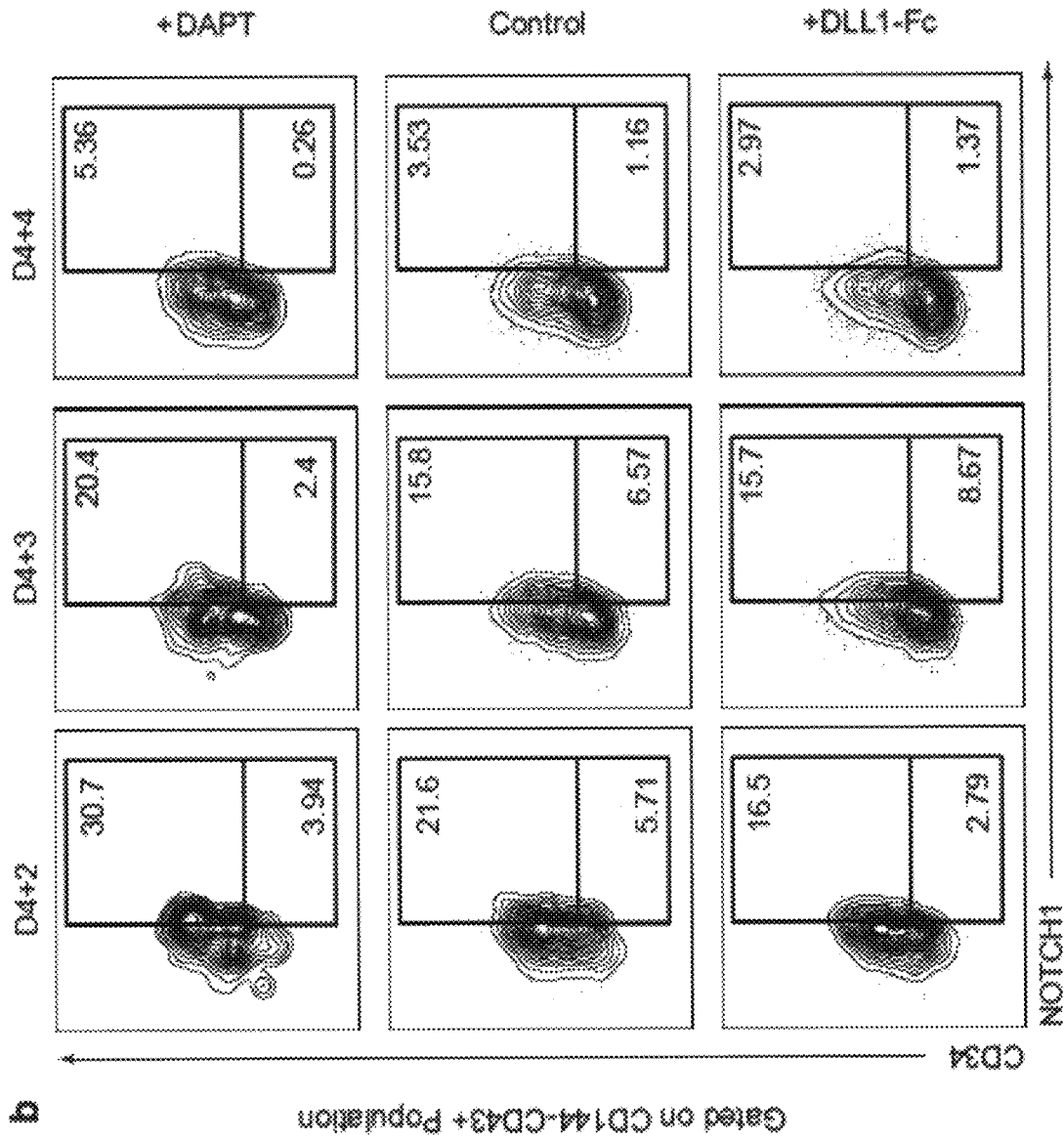

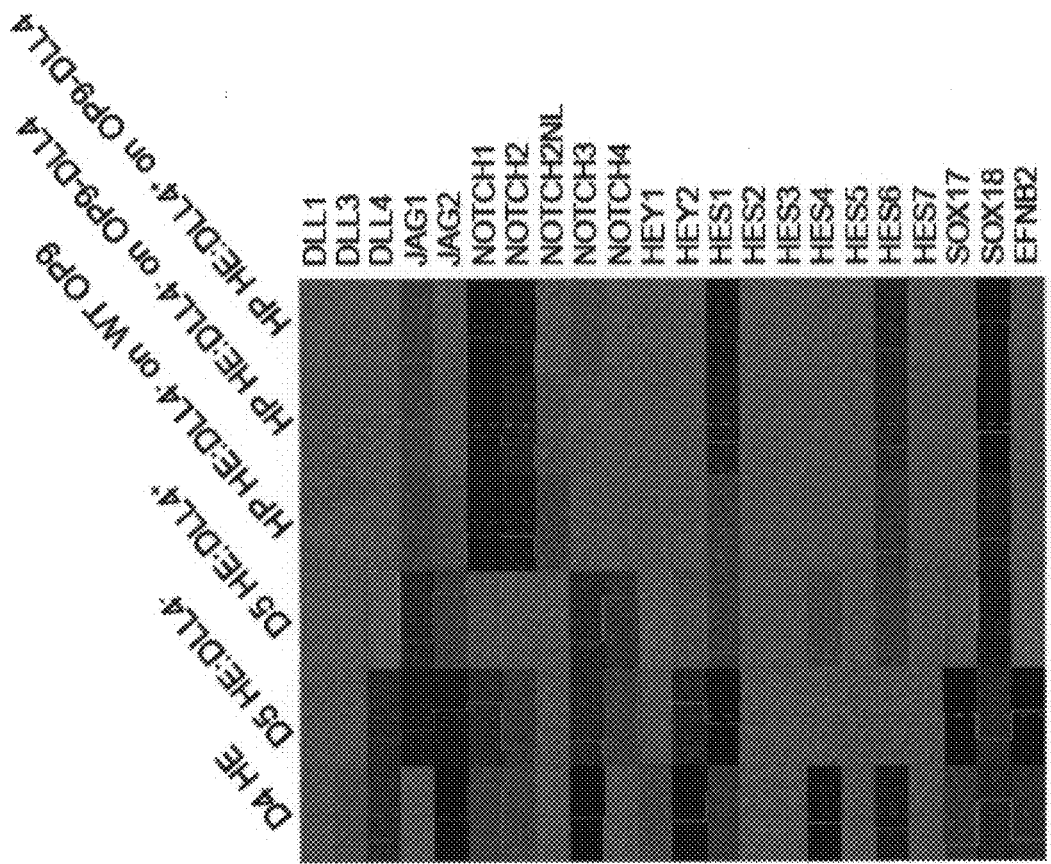
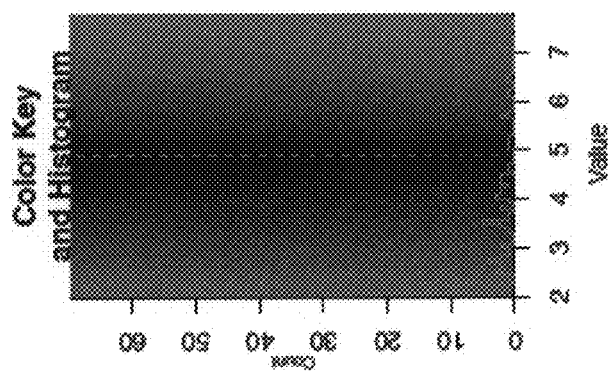
FIG. 13

FIG. 14

| Antigen | Conjugate | Source | Clone | Cat No. |
|---|---|---|---|---|
| CD4 | APC | BD Biosciences | RPA-T4 | 555349 |
| CD5 | PE-Vio770 | Miltenyi Biotec | 130-111-109 | REA782 |
| CD7 | FITC | Miltenyi Biotec | 130-105-844 | CD7-6B7 |
| CD8 | PE | BD Biosciences | HIT8a | 555635 |
| CD31 | FITC | BD Biosciences | WM59 | 555445 |
| CD31 | PE | BD Biosciences | WM59 | 555446 |
| CD31 | MicroBeads | Miltenyi Biotec | N/A | 130-091-935 |
| CD34 | FITC | BD Biosciences | 8G12 | 555821 |
| CD34 | PE-Vio770 | Miltenyi Biotec | 24D2 | 130-100-844 |
| CD41a | PE | BD Biosciences | HIP8 | 555467 |
| CD41a | APC | BD Biosciences | HIP8 | 559777 |
| CD41a | PE-Cy5 | BD Biosciences | HIP8 | 559768 |
| CD41a | PE-Cy7 | BD Biosciences | HIP8 | 561424 |
| CD41a | FITC | BD Biosciences | HIP8 | 555466 |
| CD41a | PerCP-Cy5.5 | BD Biosciences | HIP8 | 340931 |
| CD41a | PE | Miltenyi Biotec | REA386 | 130-105-612 |
| CD41a | APC-Vio770 | Miltenyi Biotec | REA386 | 130-105-563 |
| CD43 | PE | BD Biosciences | 1G10 | 560199 |
| CD43 | APC | BD Biosciences | 1G10 | 560198 |
| CD43 | BV421 | BD Biosciences | 1G10 | 562916 |
| CD43 | BV510 | BD Biosciences | 1G10 | 563377 |
| CD43 | PE | Miltenyi Biotec | DF-T1 | 130-097-362 |
| CD43 | APC | Miltenyi Biotec | DF-T1 | 130-097-367 |
| CD43 | APC-Vio770 | Miltenyi Biotec | DF-T1 | 130-101-174 |
| CD43 | VioBlue | Miltenyi Biotec | DF-T1 | 130-097-373 |
| CD43 | purified | BD Biosciences | 1G10 | 551457 |
| CD45 | PE | BD Biosciences | HI30 | 555483 |
| CD45 | APC | BD Biosciences | HI30 | 555485 |
| CD45 | BV421 | BD Biosciences | HI30 | 563879 |
| CD45 | PE | Miltenyi Biotec | 130-080-201 | 5B1 |
| CD45 | PE-Vio770 | Miltenyi Biotec | 130-096-616 | 5B1 |
| CD45 | APC | Miltenyi Biotec | 130-091-230 | 5B1 |
| CD45 | APC-Vio770 | Miltenyi Biotec | 130-096-609 | 5B1 |
| CD73 | PE | BD Biosciences | AD2 | 550257 |
| CD73 | PE-Cy7 | BD Biosciences | AD2 | 561258 |
| CD73 | Purified | BD Biosciences | AD2 | 550256 |

FIG. 14 CONTINUED

| Antigen | Conjugate | Source | Clone | Cat No. |
|---|---|---|---|---|
| CD73 | APC | BD Biosciences | AD2 | 560847 |
| CD73 | FITC | BD Biosciences | AD2 | 561254 |
| CD73 | BV421 | BD Biosciences | AD2 | 562430 |
| CD144 | PE | BD Biosciences | 55-7H1 | 560410 |
| CD144 | FITC | BD Biosciences | 55-7H1 | 560411 |
| CD144 | PerCP-Cy5.5 | BD Biosciences | 55-7H1 | 561566 |
| CD144 | PE-Vio770 | Miltenyi Biotec | REA199 | 130-100-720 |
| CD144 | VioBlue | Miltenyi Biotec | REA199 | 130-100-724 |
| CD144 | purified | eBioscience | BV13 | 14-1441 |
| CD184 | PE | BD Biosciences | 12G5 | 555974 |
| CD184 | PerCP-Cy5.5 | BD Biosciences | 12G5 | 560670 |
| CD235a | PE | BD Biosciences | GA-R2 (HIR2) | 555570 |
| CD235a | FITC | BD Biosciences | GA-R2 (HIR2) | 559943 |
| CD235a | APC | BD Biosciences | GA-R2 (HIR2) | 551336 |
| CD309 | PE | BD Biosciences | 89106 | 560494 |
| CD309 | Alexa Fluor® 647 | BD Biosciences | 89106 | 560495 |
| CD309 | APC | Miltenyi Biotec | ES8-20E6 | 130-093-910 |
| Actin | purified | Santa Cruz Biotechnology | C-2 | SC-8432 |
| Mouse IgG | Alexa Fluor® 488 | Life Technologies | polyclonal | A11001 |
| Mouse IgG | HRP | Santa Cruz Biotechnology | polyclonal | SC-2005 |
| DLL4 | PE | Miltenyi Biotec | MHD4-46 | 130-096-567 |
| DLL4 | PE-Vio770 | Miltenyi Biotec | MHD4-46 | 130-101-563 |
| DLL4 | PE | R&D Systems | 447506 | FAB1506P |
| NOTCH1 | APC | R&D Systems | 527425 | FAB5317A |
| NOTCH1 | purified | Cell Signaling Technology | C37C7 | 3439 |
| NOTCH1-ICD | purified | Cell Signaling Technology | D3B8 | 4147 |
| Rabbit IgG | Alexa Fluor® 594 | Life Technologies | polyclonal | A11012 |
| Rabbit IgG | HRP | Santa Cruz Biotechnology | polyclonal | SC-2004 |

FIG. 15

| Reagent | Fluorescence | Source | Cat No |
|---|---|---|---|
| 7-AAD | 488/647 | Cayman Chemicals | 11397 |
| Annexin V | PE | BD Biosceinces | 556421 |
| CellTracer | 405/450 | ThermoFisher | C34557 |
| Ghost Dye Red 780 | 633/780 | Tonbo Bio | 13-0865 |
| Ghost Dye Violet 510 | 405/510 | Tonbo Bio | 13-0870 |

FIG. 16

| Gene | Forward Sequence | SEQ ID NO: | Reverse Sequence | SEQ ID NO: |
|---|---|---|---|---|
| CXCR4 | TCAGTGGCTGACCTCCTCTT | 1 | CTTGGCCTTTGACTGTTGGT | 2 |
| DLL4 | CAGTGGGCAGCGAAGCTACA | 3 | ACAGGCAGTGGTAGCCATCCTC | 4 |
| EPHB2 | CTCCTCAACTGTGCCAAACCA | 5 | GGTTATCCAGGCCCTCCAAA | 6 |
| GATA2 | CCCTAAGCAGCGCAGCAA | 7 | TGACTTCTCCTGCATGCACT | 8 |
| HAND1 | GCCTACCTGATGGACGTGCT | 9 | GCCGGTGCGTCCTTTAATCC | 10 |
| HBA2 | CGGTCAACTTCAAGCTCCTAA | 11 | GCCCACTCAGACTTTATT | 12 |
| HBB | GGCACCTTTGCCACACTG | 13 | CACTGGTGGGGTGAATTCTT | 14 |
| HBE1 | GCCTGTGGAGCAAGATGAAT | 15 | GCGGGCTTGAGGTTGT | 16 |
| HBG1 | CTTCAAGCTCCTGGGAAATGT | 17 | GCAGAATAAAGCCTATCCTTGAAAG | 18 |
| HBZ1 | CGGTGAAGAGCATCGACG | 19 | GGATACGACCGATAGGAACTTGT | 20 |
| HES1 | TACCCCAGCCAGTGTCAAC | 21 | TCAGCTGGCTCAGACTTTCA | 22 |
| HEY2 | TTCAAGGCAGCTCGGTAACTGAC | 23 | CATACTGATGCACTGCTGGATGG | 24 |
| MYB | ACGGTCCGAAACGTTGGTCTG | 25 | CCCCAGTCTCTTGTGTGCCTGG | 26 |
| NOTCH1 | CAATGTGGATGCCGCAGTTGTG | 27 | CAGCACCTTGGCGGTCTCGTA | 28 |
| NR2F2 | TGGTTCCAAACCAGTTTATTCTGT | 29 | AAGTGCGTTTCCATCATCTTTGAG | 30 |
| RPL13a | CCTGGAGGAGAAGAGGAAAGAGA | 31 | TTGAGGACCTCTGTGTATTTGTCAA | 32 |
| SOX17 | GCCAAGGGCGAGTCCCGTA | 33 | GCATCTTGCTCAACTCGGCGTTGTGCA | 34 |

METHOD FOR THE INDUCTION OF ARTERIAL-TYPE OF HEMOGENIC ENDOTHELIUM FROM HPSCS

CROSS-REFERENCE TO RELATED APPLICATIONS

This application claims priority to U.S. Provisional Application No. 62/460,348 filed on Feb. 17, 2016, the contents of which are incorporated by reference in its entirety

STATEMENT REGARDING FEDERALLY SPONSORED RESEARCH

This invention was made with government support under HL099773, HL116221 and OD011106 awarded by the National Institutes of Health. The government has certain rights in the invention.

BACKGROUND

Generating autologous hematopoietic stem cells (HSCs) from induced pluripotent stem cells (iPSCs) that can be precisely genetically modified with designer endonucleases, and subsequently clonally selected, represents a promising approach for novel patient-specific gene therapies. Although multiple studies were able to generate hematopoietic progenitors (HPs) with a HSC phenotype and limited engraftment potential from pluripotent stem cells (PSCs)[1-4], the robust and consistent engraftment with recapitulation of the full spectrum of terminally differentiated hematopoietic cells, including lymphoid cells has not been achieved. Thus, identifying key cellular and molecular programs required for proper HSC specification in vitro is essential to overcome the current roadblocks.

SUMMARY OF THE INVENTION

The present disclosure provides methods of producing arterial type hemogenic endothelial cells (AHE) which are CD144+CD43−CD73−DLL4+ HE that express high level of EFNB2 and NOTCH1 arterial markers and MYB gene required for definitive hematopoiesis. These cells have broad lympho-myeloid and definitive erythroid potentials.

In one aspect, the disclosure provides method of inducing an arterial-type hemogenic endothelium (AHE) cell population, comprising the steps of (a) obtaining CD144+CD43−CD73-hemogenic endothelial cells on day 4 of differentiation (D4), and (b) exposing the D4 HE cells to a sufficient amount of a NOTCH activation agent, such that arterial-type cells (AHE cells) are created, wherein the AHE cells are detected as CD144+CD43−CD73−DLL4+ HE that express high level of EFNB2 and NOTCH1 arterial markers and MYB gene. In some aspects, the method additionally comprises the step of exposing the AHE created in step (b) to a sufficient amount of a NOTCH activation agent, such that the AHE undergo endothelial-to-hematopoietic transition and produce definitive-type hematopoietic progeny with adult-like characteristics.

In another aspect, the disclosure provides a method of inducing an arterial-type hemogenic endothelium (AHE) cell population, comprising the steps of exposing immature CD144$^+$CD43$^-$CD73$^-$ hemogenic endothelial (HE) cells which express HAND1 to a sufficient amount of a NOTCH activation agent, such that AHE cells are obtained, wherein the AHE cells are detected as CD144+CD43−CD73−DLL4+ HE that express EFNB2 and NOTCH1 arterial markers and MYB gene.

In another aspect, the disclosure provides a cell population comprising at least 90% AHE cells produced by the methods described herein. In another aspect, the disclosure provides a cell population comprising at least 95% AHE-cells produced by the methods described herein.

In another aspect, the disclosure provides a method of inducing a population of differentiated hematopoietic cells, comprising the steps of creating the AHE cells of claim 1 and further differentiating the cells into a cell type selected from the group of platelet-producing megakaryocytes, adult-globin expressing erythrocytes, and T-lymphocytes.

In yet another aspect, the disclosure provides a method of differentiating T cells from CD144+CD43−CD73− hemogenic endothelial cells, the method comprising: (a) culturing CD144+CD43−CD73− hemogenic endothelial cells in a sufficient amount of a NOTCH activation agent to produce hematopoietic progenitors (HPs) with increased T-cell potential compared to cells not cultured with NOTCH activation agent, (b) culturing the hematopoietic progenitors in a sufficient amount of NOTCH activation agent with T-cell differentiation conditions for a sufficient time to produce T cells.

In yet another aspect, the disclosure provides a method of isolating an arterial-type hemogenic endothelium (AHE) cell population, comprising the steps of detecting and isolating DLL4+ AHE cells in day 5 of differentiation (D5), wherein the DLL4+ AHE detected are CD144+CD43−CD73−DLL4+ HE that express high level of EFNB2 and NOTCH1 arterial markers and MYB gene.

In yet another aspect, the disclosure provides a method of obtaining a cellular composition comprising more than 95% arterial-type hemogenic endothelium (AHE) cell population, comprising the steps of a. differentiating human pluripotent stem cells (hPSCs) for five days in defined conditions to induce formation of CD144+CD43−CD73−D114+ arterial HE; and b. detecting and isolating a cell fraction being characterized by CD144+CD43−CD73−DLL4+ phenotype.

BRIEF DESCRIPTION OF THE DRAWINGS

The patent or patent application file contains at least one drawing in color. Copies of this patent or patent application publication with color drawings will be provided by the Office upon request and payment of the necessary fee.

Figures 1A, 1B, 1C, 1D, 1E, 1F:
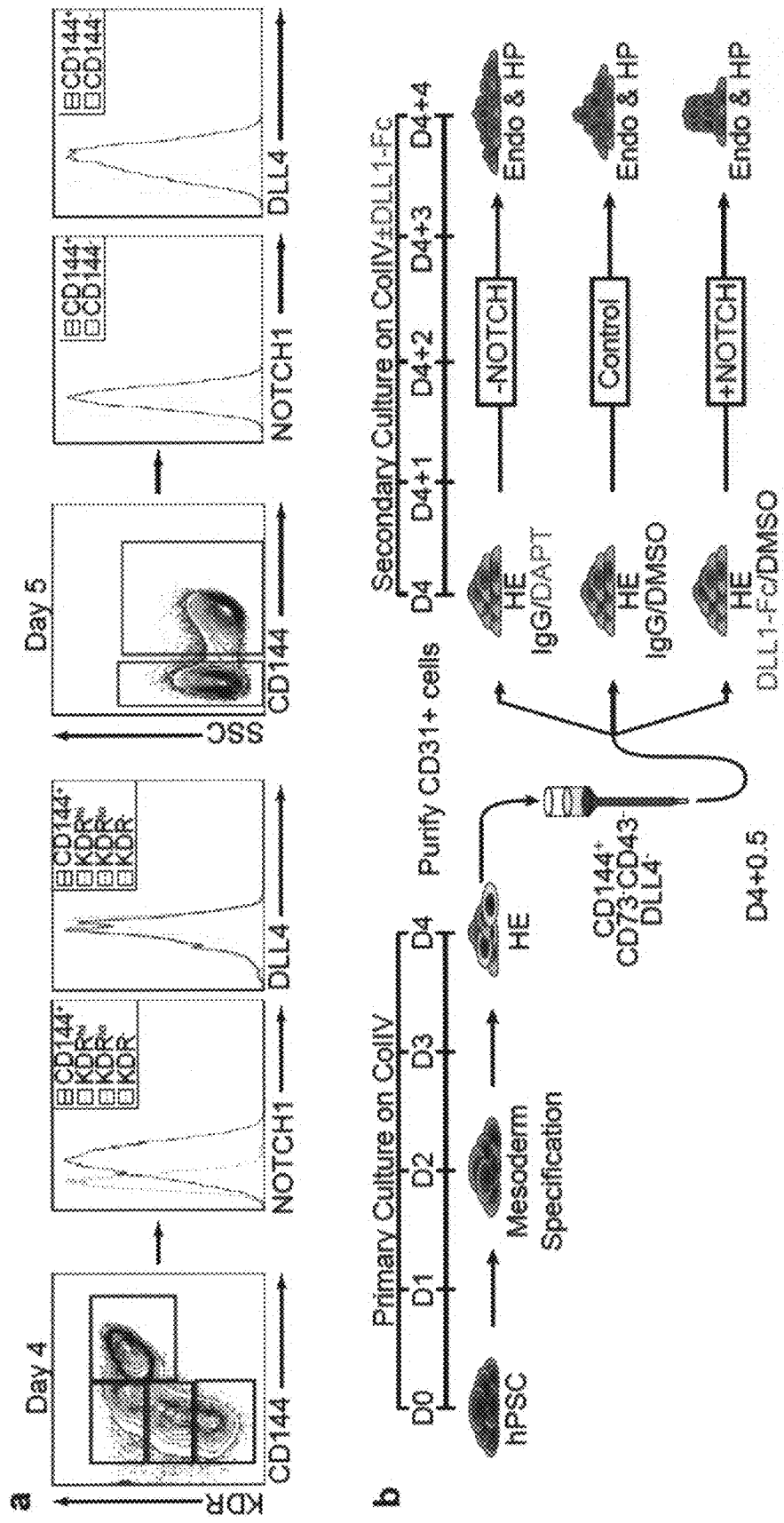
FIGS. 1A-1F show NOTCH activation increases hematopoiesis from D4 HE. (a) NOTCH1 receptor expression is first detected on D4 CD144+ cells. DLL4 expression is first detected on D5 CD144+ endothelial cells. (b) Schematic diagram of experiments. Cells were differentiated for 4 days on collagen-IV, D4 CD144+CD43−CD73− HE cells were purified using CD31-microbeads and plated in 3 different NOTCH conditions. (c) Western blot of D4 HE cultured for 24 h (D4+1) in presence of DAPT or DLL1-Fc shows a decrease in the activated cleaved form of NOTCH1 in DAPT treated cells, and an increase in the activated cleaved form of NOTCH1 in cells plated on DLL1-Fc. (d) qPCR analysis shows decreased HES1 mRNA expression in D4 HE cultured for 12 hours (D4+0.5) with DAPT, while HES1 mRNA expression is increased in cells plated on DLL1-Fc. Results are mean±SEM for at least 3 independent experiments. (e) Flow cytometry on each day from D4+1 to D4+4 shows decreased CD43+ HPs in the cultures treated with DAPT, and increased HPs in the cultures plated on DLL1-Fc. (f) Total numbers of CD43+ HPs and CD144+CD43− endothelial cells in cultures plated on DLL1-Fc. Results are mean±SEM for at least 3 independent experiments. *p<0.05, p<0.01, *p<0.001.
Figures 1A, 1B, 1C, 1D, 1E, 1F:
Figures 1A, 1B, 1C, 1D, 1E, 1F:
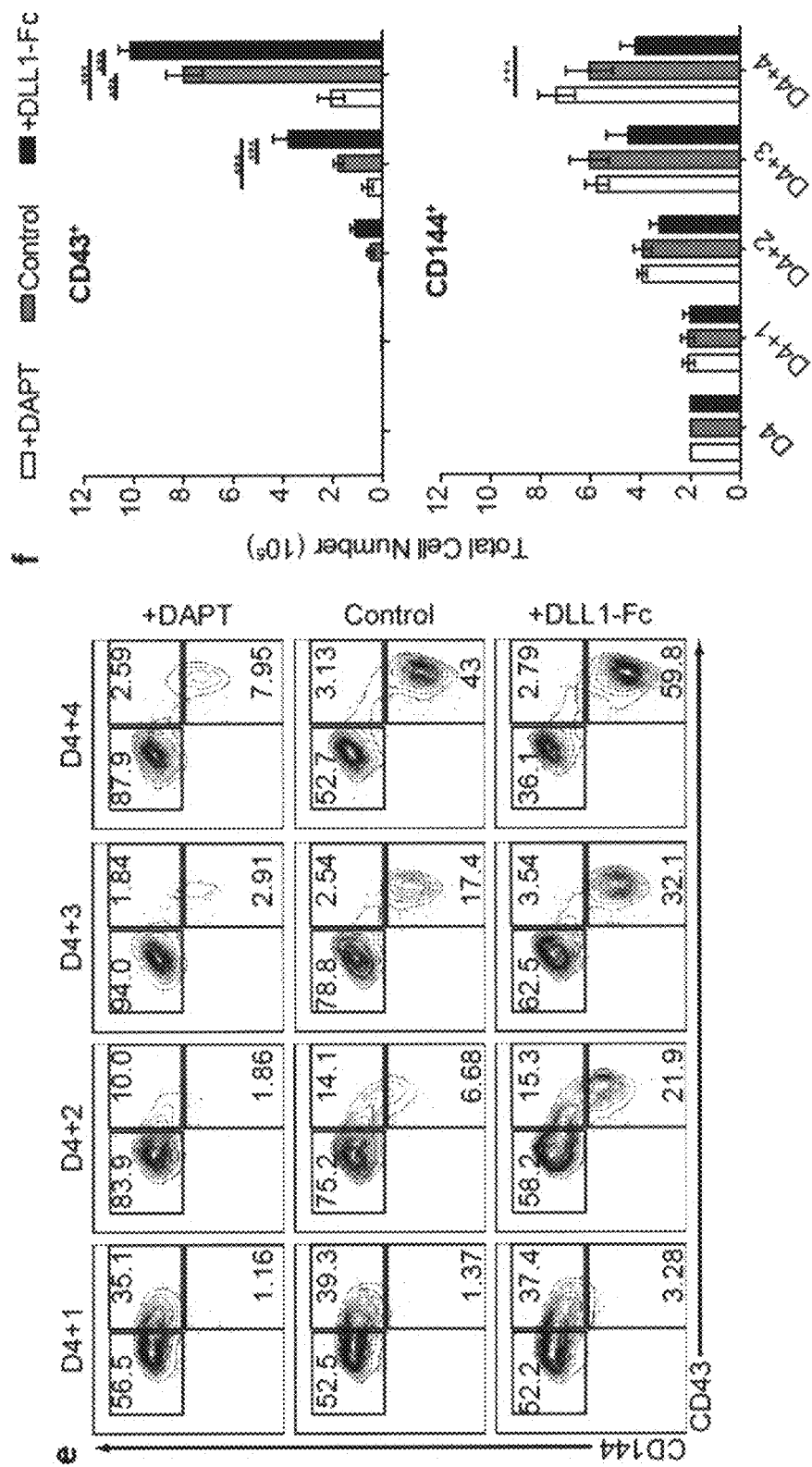

FIGS. 2A-2G show increased NOTCH activation facilitates EHT. (a) Schematic diagram of experiments. D4 HE cultured in presence of DAPT for 4 days (D4+4) or 1 day (D4+1), or DMSO (control). CD144+ endothelial and CD43+ blood cells were analyzed following 4 days of culture. (b) Flow cytometric analysis demonstrates that NOTCH activation facilitates EHT as evidenced by the decrease in hematopoietic activity when DAPT is added only from D4 to D4+1. (c) Frequencies of endothelial and blood cells in HE cultures treated with DAPT or DMSO (control). Results are mean±SEM for at least 3 independent experiments. (d) Single D4 HE cells were FACS sorted into 96 well plate with OP9, OP9+DAPT, and OP9-DLL4. Colonies were scored based on CD43 and CD144 expression on D4+10 by immunofluorescence and counted by eye. (e) Representative flow cytometric cell proliferation analysis and (f) bar graph conducted with CellTracer shows an increase in the first generation (Gen1) CD43+ cells on D4+1 and a proportional decrease in Gen1 CD144+ endothelial cells, suggesting that the increase in blood cells is due to an increase in EHT and not just proliferating HPs. (g) Line graph depicting the percent of each generation within the CD43+ population on D4+4 in each of the NOTCH treatment conditions. Results are mean±SEM for at least 3 independent experiments. No significant change of each generation between conditions suggests that NOTCH does not affect proliferation of HPs. Generation gates in (f) and (g) were determined by concatenating D4 to D4+4 results and utilizing FlowJo™'s proliferation assay. Scale bar represents 100 µm *p<0.05, p<0.01, *p<0.001

FIGS. 3A-3D show NOTCH activation at HE stage increases definitive hematopoiesis. (a) D4 HE were cultured with DAPT or in the presence of DLL1-Fc (see FIG. 1b schematic diagram). Cells were collected after 4 day of differentiation (D4+4) and used to determine frequencies of hematopoietic progenitors in CFU assay. Increase in multipotential GEMM and GM colonies in the DLL1-Fc culture condition suggests that NOTCH activation supports expansion of the most immature HPs. Results are mean±SEM for at least 3 independent experiments. (b) Flow cytometric analysis of Runx1+23-eGFP transgene expression in D4 HEPs cultured with DAPT or on DLL1-Fc. Runx1+23 enhancer activity increases in the cultures plated on DLL1-Fc and decreases in the DAPT treated cultures. (c) T cell potential of HP collected after 4 days of culture D4 HEs in presence of DAPT or DLL1-Fc. Bars are mean+SEM for at least 3 independent experiments. (d) Ratio of α/ζβ/γ and β/ε globin chain expression in erythroid cultures generated from D4 HE in presence of DAPT or DLL1-Fc. Results are mean±SEM for at least 3 independent experiments. *p<0.05, p<0.01, *p<0.001.

FIGS. 4A-4E show NOTCH activation induces formation of arterial type HE cells. (a) Flow cytometric analysis of DLL4 and CD73 expression following culture of D4 HE for 1 or 2 days in the presence of DAPT or DLL1-Fc. NOTCH activation on D4 HE specifically increases the CD144+ CD73−DLL4+ population. (b) Frequencies of DLL4+ cells in hemogenic (CD73−) and non-hemogenic fractions of endothelium following 1 and 2 days of culture of D4 HE in the presence of DAPT or DLL1-Fc. Results are mean±SEM for at least 3 independent experiments. (c) Flow cytometric analysis of Runx1+23 enhancer activity following 1 day of culture of D4 HE in presence of DAPT or DLL1-Fc. Runx1+23 enhancer activity is limited to the CD144+CD73− DLL4+ population. (d) Schematic diagram of FACS isolation of endothelial subpopulations formed on D5 of differentiation. (e) qPCR analysis of arterial (NOTCH1, DLL4, EFNB2, HEY2, SOX17, CXCR4), venous (NR2F2), hematopoietic (MYB, GATA2) and mesodermal (HAND1) genes in D4 HE and D5 endothelial subpopulations. Results are mean±SEM for at least 3 independent experiments. *p<0.05, p<0.01, *p<0.001.

FIGS. 5A-5G show arterial-type HE undergoes EHT under high NOTCH activation and produce definitive-type HPs. (a) Schematic diagram of subsequent experiments. D5 CD144+CD43−CD73− cells were sorted based on DLL4 expression (D5 HE:DLL4+/−) using FACS and cultured on either OP9 or OP9-DLL4 for 4 days (D5+4). (b) and (c) Flow cytometric analysis of CD43+ hematopoietic and CD144+ endothelial cells following culture of D5 HE:DLL4+ and D5 HE:DLL4− on either OP9 or OP9-DLL4. Bars in (c) are mean±SEM for at least 3 independent experiments. (d) The effect of NOTCH inhibition with DAPT on blood production from D5 DLL4+ and DLL4− HE. No significant differences were found when HE:DLL4− cells were treated with DAPT. Results are mean±SEM for at least 3 independent experiments. *p<0.05, p<0.01, *p<0.001 (e) CFC potential of hematopoietic cells generated from D5 DLL4+ and DLL4− HE following 5 days culture on OP9-DLL4. Results are mean±SEM for at least 3 independent experiments. CFC-GEMMs are significantly increased in DLL4+ cultures on OP9-DLL4. (f) Ratio of α/ζ, β/γ and β/ε globin chain expression in erythroid cultures generated form hematopoietic cells collected from D5 DLL4+ and DLL4− HE cultured on OP9-DLL4 (D5+4 cells). Results are mean±SEM for at least 3 independent experiments. *p<0.05, p<0.01, *p<0.001. (g) Limiting dilution assay to determine the frequency of T cell progenitors within the D5+5 HPs generated from HE:DLL4− on OP9, HE:DLL4− on OP9-DLL4, and HE:DLL4+ on OP9-DLL4.

FIGS. 6A-6D show HPs derived from DLL4+ HE cells activate definitive hematopoietic program. (a) Experimental strategy for generating and characterizing HE:DLL4+/−-derived HPs. D4 HE cells were cultured on DLL1-Fc for 24 h, followed by purification of D4+1 HE:DLL4+ and HE:DLL4− and subsequent culture on OP9 or OP9-DLL4. Five days later (D4+1+5), CD34+CD43+CD45+CD235a/41a− population was FACSorted from each condition and RNA was extracted for RNA-seq. (b) A heatmap of differentially expressed transcription factor genes in HPs derived from indicated cell populations. The expression is shown as a log ratio of gene expression relative to HPs generated from HE:DLL4− cells on OP9-DLL4. (c) Transcriptional regulatory network reconstructed with the nine transcription factor-encoding genes (the nodes with incoming interactions) differentially expressed in HPs derived from HE:DLL4+. Size of the nodes represents relative abundance of mRNA of the respective gene, computed as log 2 (fold change) in DLL4+ versus DLL4− (see circle size scale below). Statistically insignificant changes in mRNA abundance (examples: GATA1, GATA2) were set to zero. Upregulation effects are mapped onto the node size as indicated; nodes of size less than those of GATA1/GATA2 reflect genes which mRNA levels were downregulated in DLL4+. Note that the absolute abundance of GATA2 mRNA was systematically higher than GATA1 in all the samples. The color density represents enrichment of known targets of that transcription factor (regulon members) among the differentially expressed genes (see −log 10(FDR) color scale below). Network visualization was performed using Cytoscape ver. 3.4.0. (d)

Schematic diagram of NOTCH regulation on HE specification and EHT. The most immature hPSC-derived CD144+ CD43−CD73− HE cells expressing NOTCH1 but lacking arterial and venous identity arise on day 4 of differentiation. NOTCH activation induces specification of arterial-type CD73− HE and CD73+ non-HE that are DLL4+, first detectable on day 5 of differentiation. DLL4+ HE cells upregulate arterial markers, but also express hematopoietic genes. Subsequently, arterial-type HE:DLL4+ are NOTCH-dependent and produce hematopoietic progenitors that have definitive-type characteristics. Day 4 HE cells that are not DLL4+ by day 5 of differentiation undergo EHT independent of NOTCH activation and produce NOTCH-independent hematopoietic progenitors with primitive potential.

FIGS. 7A-7F show the effect of NOTCH signaling on EHT. (a) Phenotype of day 4 CD144+ cells. (b) Effect of NOTCH inhibition and activation on hematopoiesis from D4 HE cells generated from WA09 embryonic stem cells (ESCs), and induced pluripotent stem cells (iPSUs) derived from bone marrow hematopoietic cells (IISH2i-BM9), cord blood (CB-iPSC6) and dermal fibroblasts (DF19-9-7T). The NOTCH effects are consistent across different hPSC lines. (c) Evaluation of EHT from D4 HE cultured on OP9, OP9-DLL4 or in presence of DAPT. NOTCH activation had similar effects on hematopoiesis whether in stroma/serum or stroma-/serum-free conditions. (d) Evaluation of EHT from D4 HE cultured on OP9 versus OP9-JAG1. OP9-JAG1 had little effect on EHT, unlike OP9-DLL4. (e) Measuring the effect of increasing concentrations of DLL1-Fc with increasing cell density of D4 HE cells. (f) Effect of JAG1-Fc on hematopoiesis from day 4 HE.

Figures 8A, 8B, 8C:
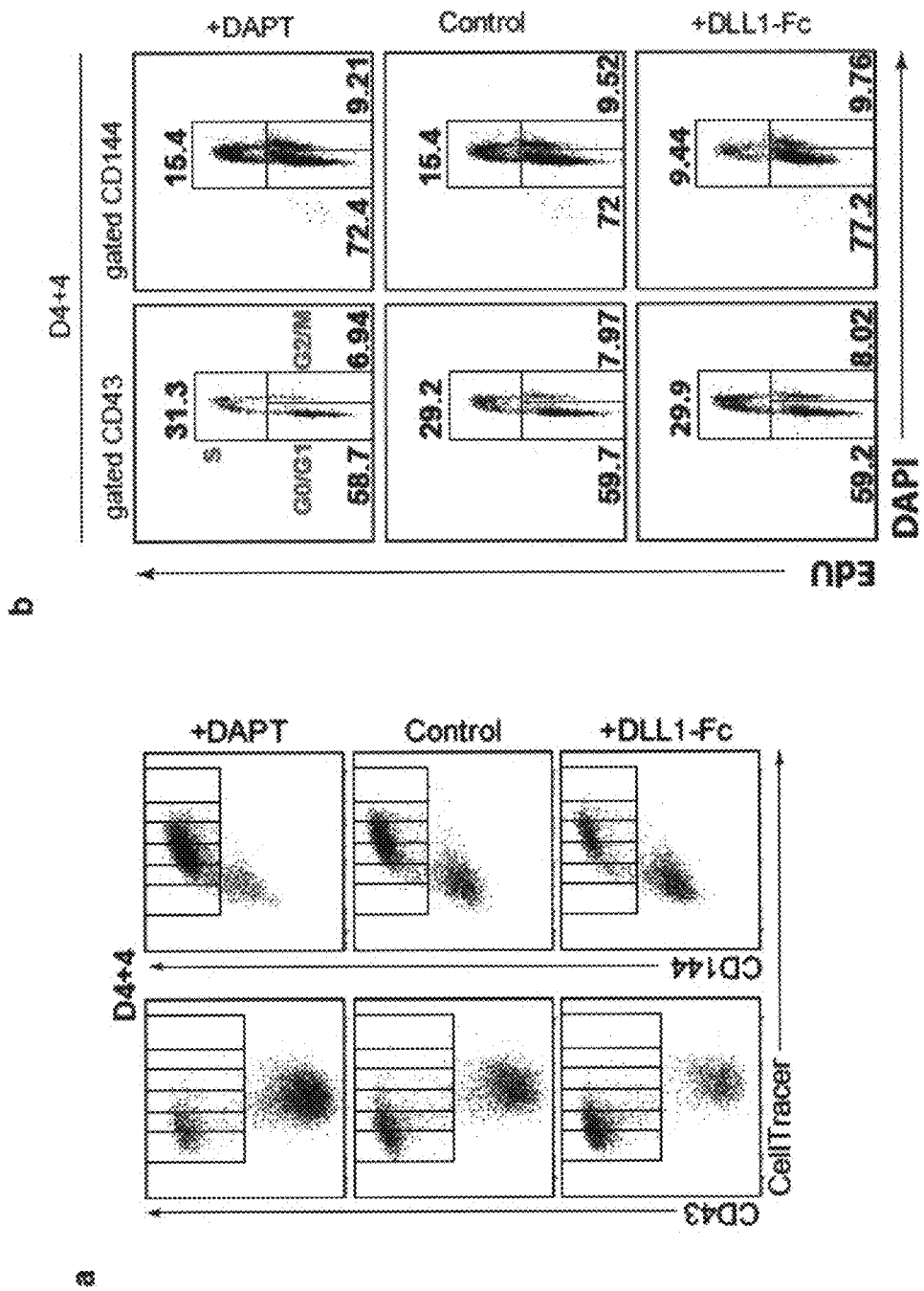
Figures 8A, 8B, 8C:
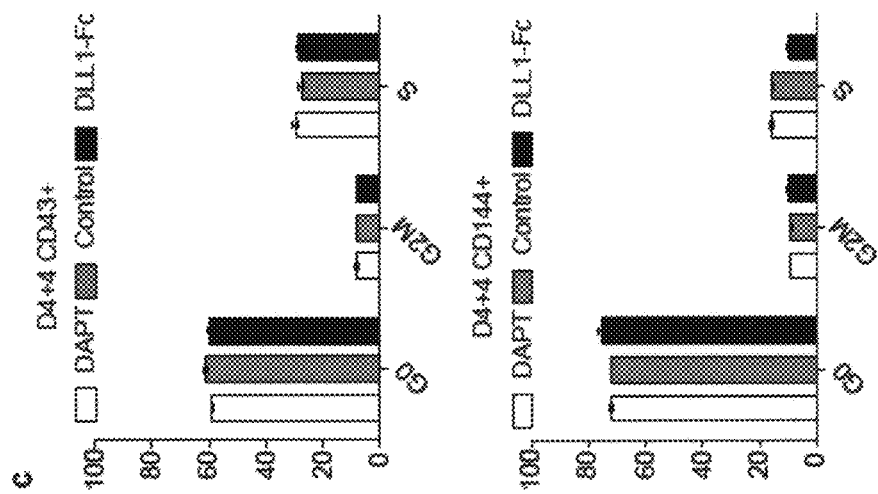

FIGS. 8A-8C show effect of NOTCH signaling on proliferation and cycling of D4+4 cells. (a) Representative flow cytometric cell proliferation analysis representing at least 3 independent experiments conducted with CellTracer. Generation gates were determined by concatenating D4 to D4+4 results and utilizing FlowJo™'s proliferation assay. (b) Representative dot plots show flow cytometric analysis of cell cycle using EdU and DAPI staining on D4+4 cells. (c) Bar graphs reveal no significant changes in cell cycling phases between each condition on D4+4. Results are mean±SEM for at least 3 independent experiments.

Figures 9A, 9B:
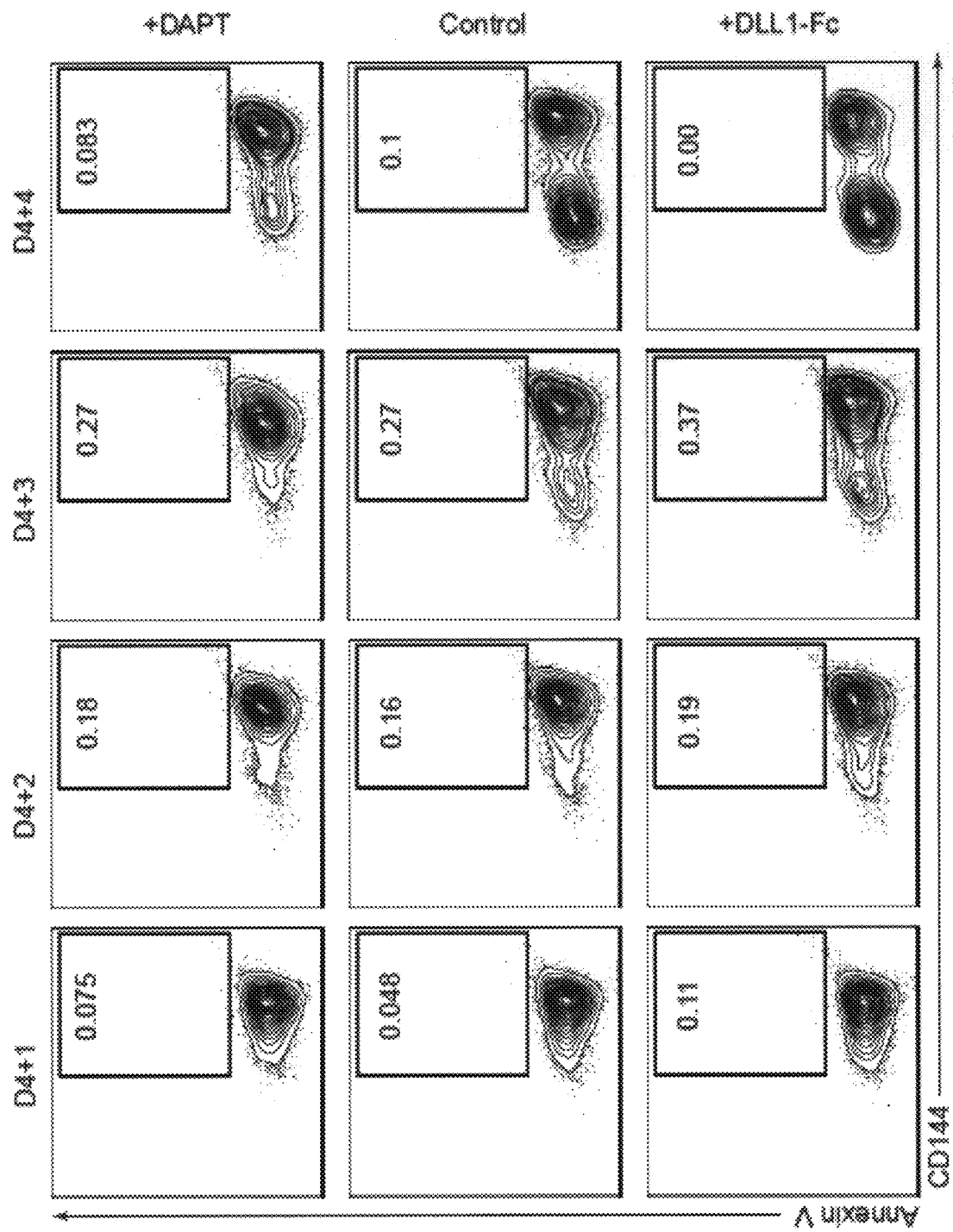
Figures 9A, 9B:
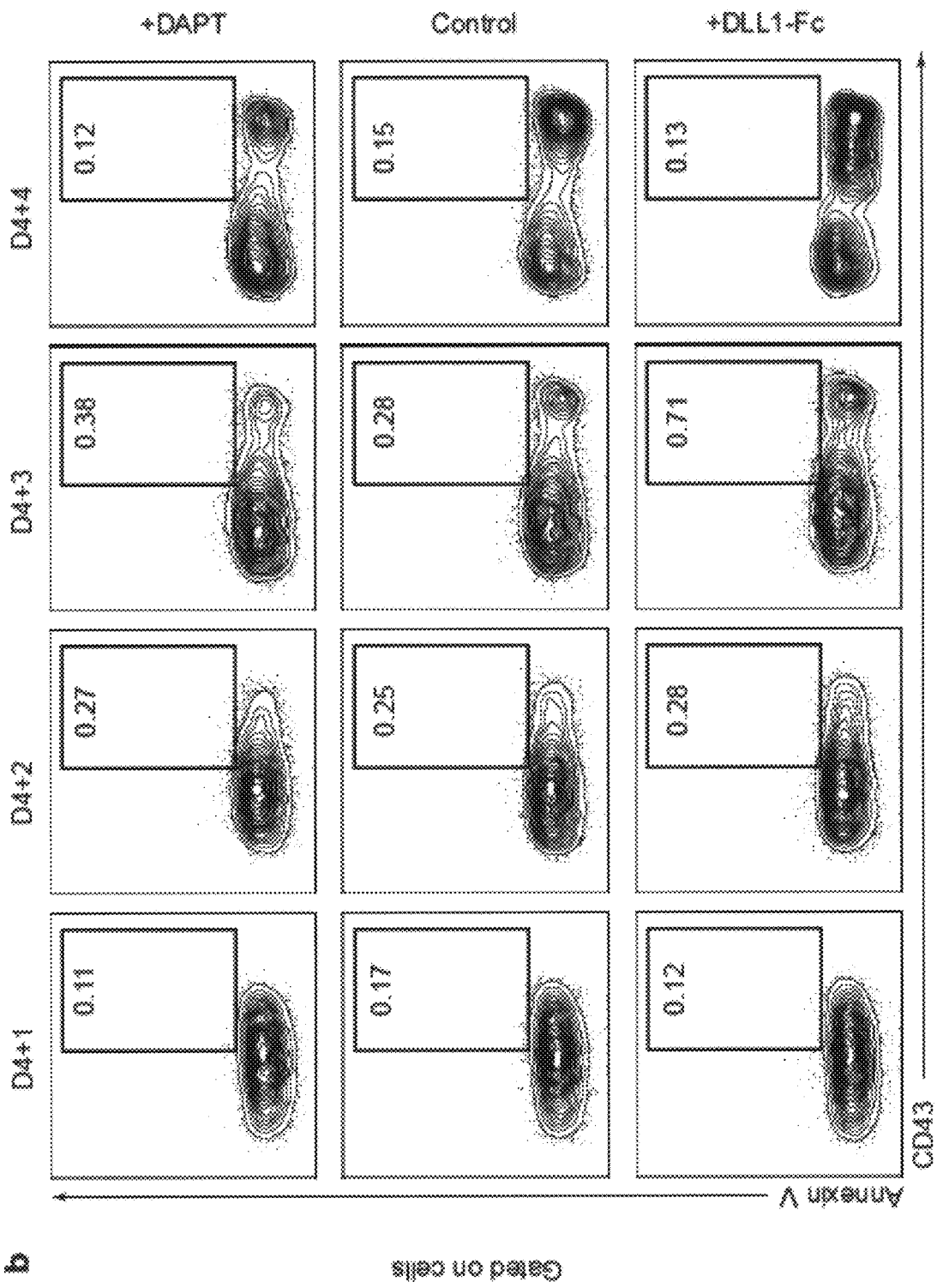

FIGS. 9A-9B show flow cytometry of Annexin V to determine apoptosis during secondary culture of D4 HE cells in the presence of DAPT or DLL1-Fc. Flow cytometry showing the percent of apoptotic cells via Annexin V staining in the (a) endothelial and (b) hematopoietic populations. Lack of significant differences in apoptotic cells in different conditions provides evidence that NOTCH signaling does not affect cell survival following EHT.

FIGS. 10A-10B show NOTCH1 expression in CD34+ hematoendothelial populations during secondary culture of D4 HE cells in the presence of DAPT or DLL1-Fc. (a) Expression of NOTCH1 on endothelial cells following secondary culture of D4 HE cells. CD144+CD43-endothelial cells have decreased NOTCH1 expression from D4+1 to D4+4 and (b) Expression of NOTCH1 on hematopoietic cells following secondary culture of D4 HE cells. CD144-CD34+CD43+ hematopoietic progenitors have increased NOTCH1 expression D4+2 to D4+4 as compared to CD34-CD43+ cells.

Figures 11A, 11B, 11C:
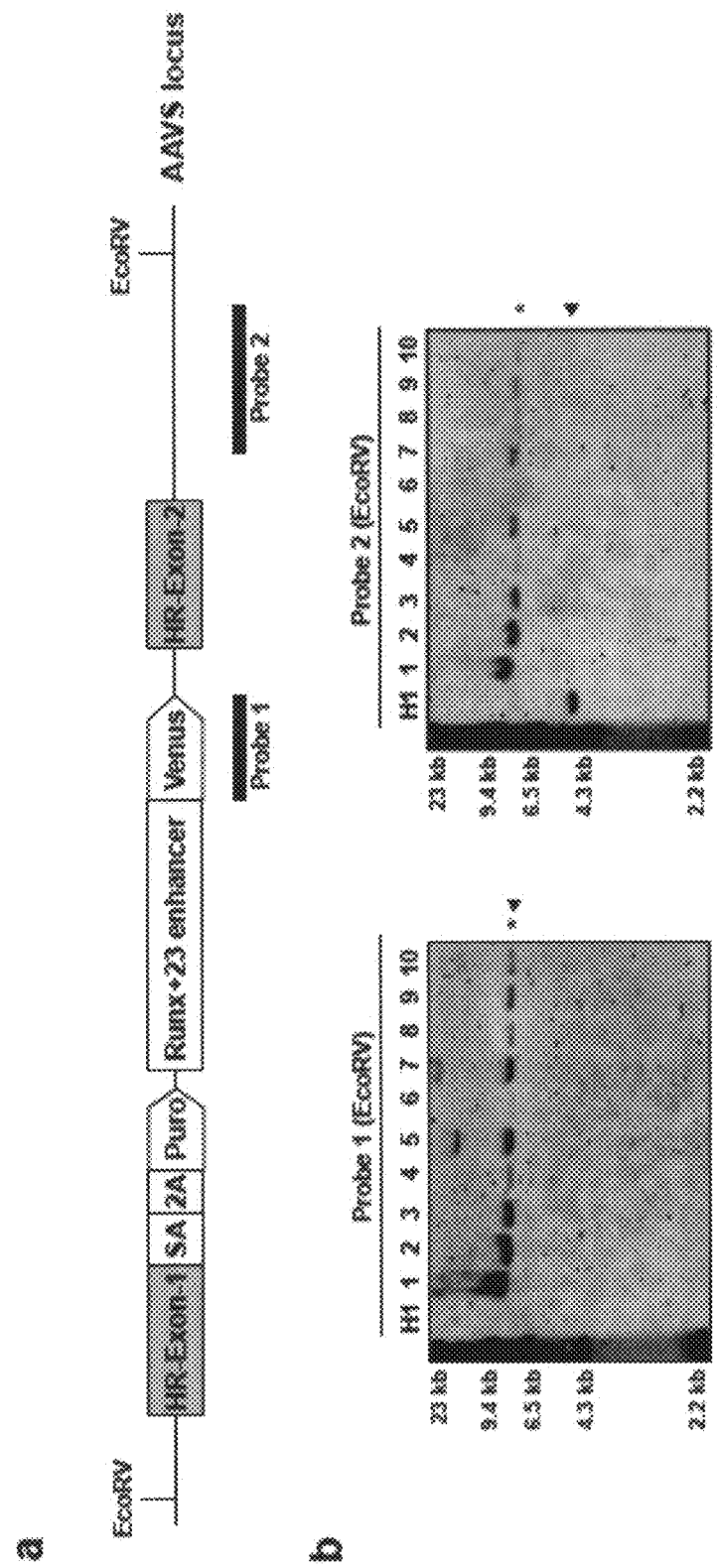
Figures 11A, 11B, 11C:
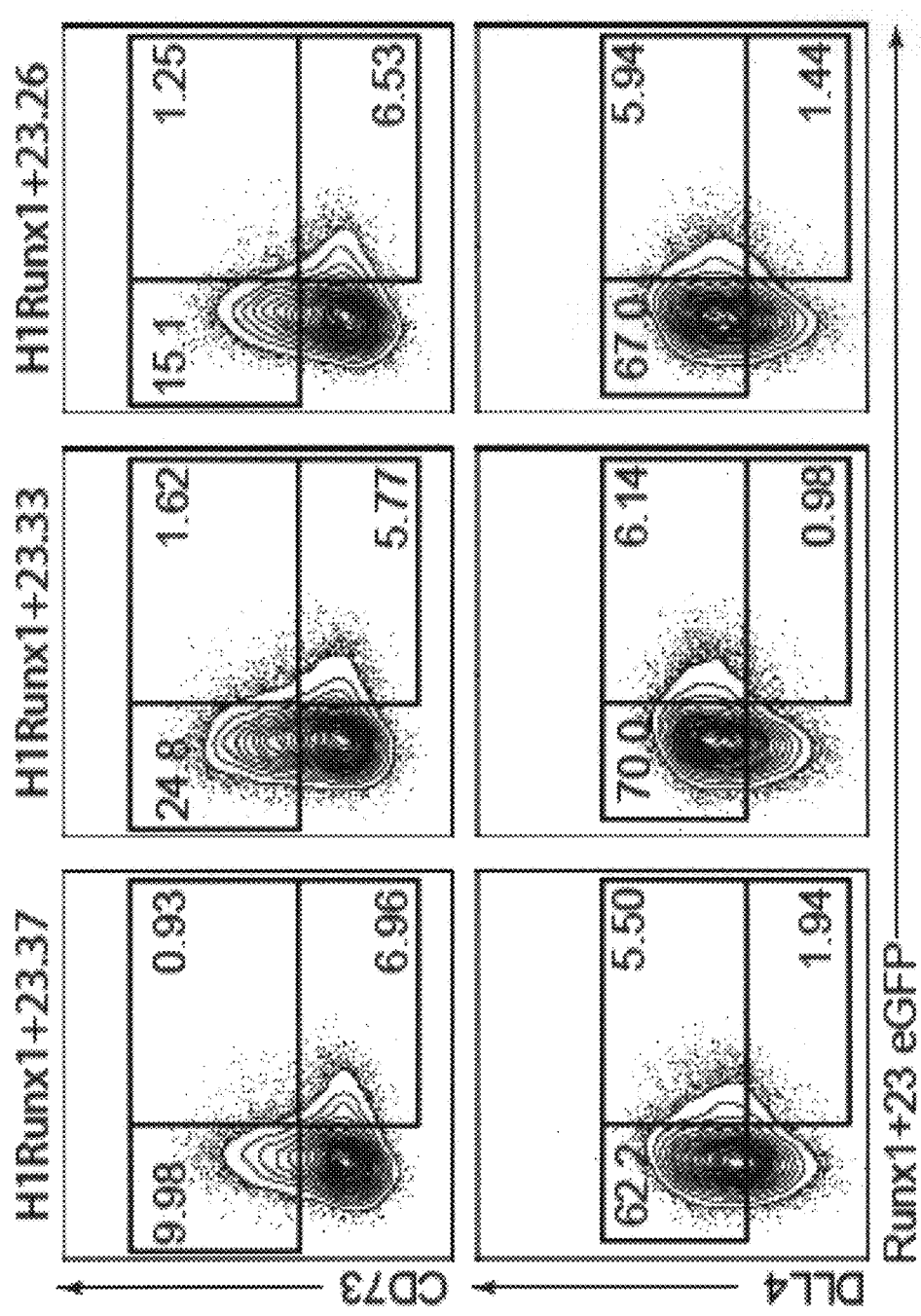

FIGS. 11A-11C show Generation of RUNX1+23-eGFP reporter H1 hESC line. (a) Schematic diagram of the construct used for the targeting of RUNX1+23-eGFP reporter into AAVS locus. Donor plasmid was integrated into the cleavage location of the Zinc Finger-Nuclease pair. (b) Southern blot analysis of the H1 cells targeted with the donor plasmid containing RUNX1+23-eGFP construct. Blot shows EcoRV digested genomic DNA hybridized with DIC-labeled 5' internal probe 1 (wt=no band, targeted=8.1 kb) and 3' external probe 2 (wt=5.4 kb, targeted=8.8 kb). Filled arrow=wild type; Asterisk=targeted (c) D5 flow of 3 different RUNX1+23 reporter hESC lines reveals that all eGFP+ cells are DLL4+CD73−.

Figure 12:
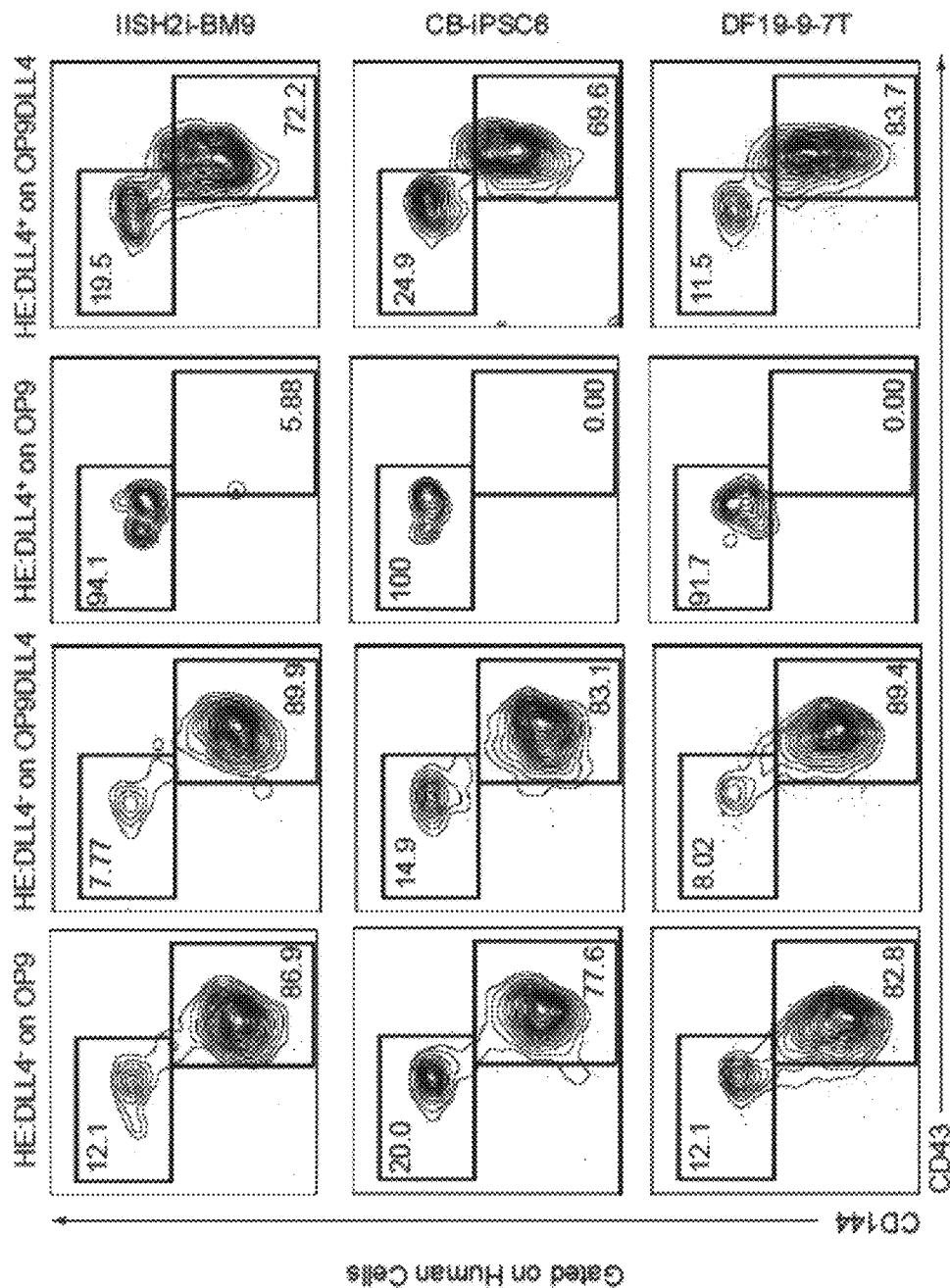

FIG. 12 shows D5 HE subsets derived from different hiPSC lines have the same response to OP9 and OP9-DLL4. Bone marrow IISH2iBM9, cord blood CB-iPSC6 or fibroblast-derived DF19-9-7T iPSCs were differentiated for 5 days in defined conditions. D5 HE:DLL4− and D5 HE:DLL4+ were sorted and cultured on OP9 or OP9-DLL4 for 4 days. D5+4 flow plots of D5 HE cells demonstrate that D5 HE:DLL4+ cells show hemogenic activity only when cultured on OP9-DLL4.

Figures 6A, 6B, 6C, 6D:
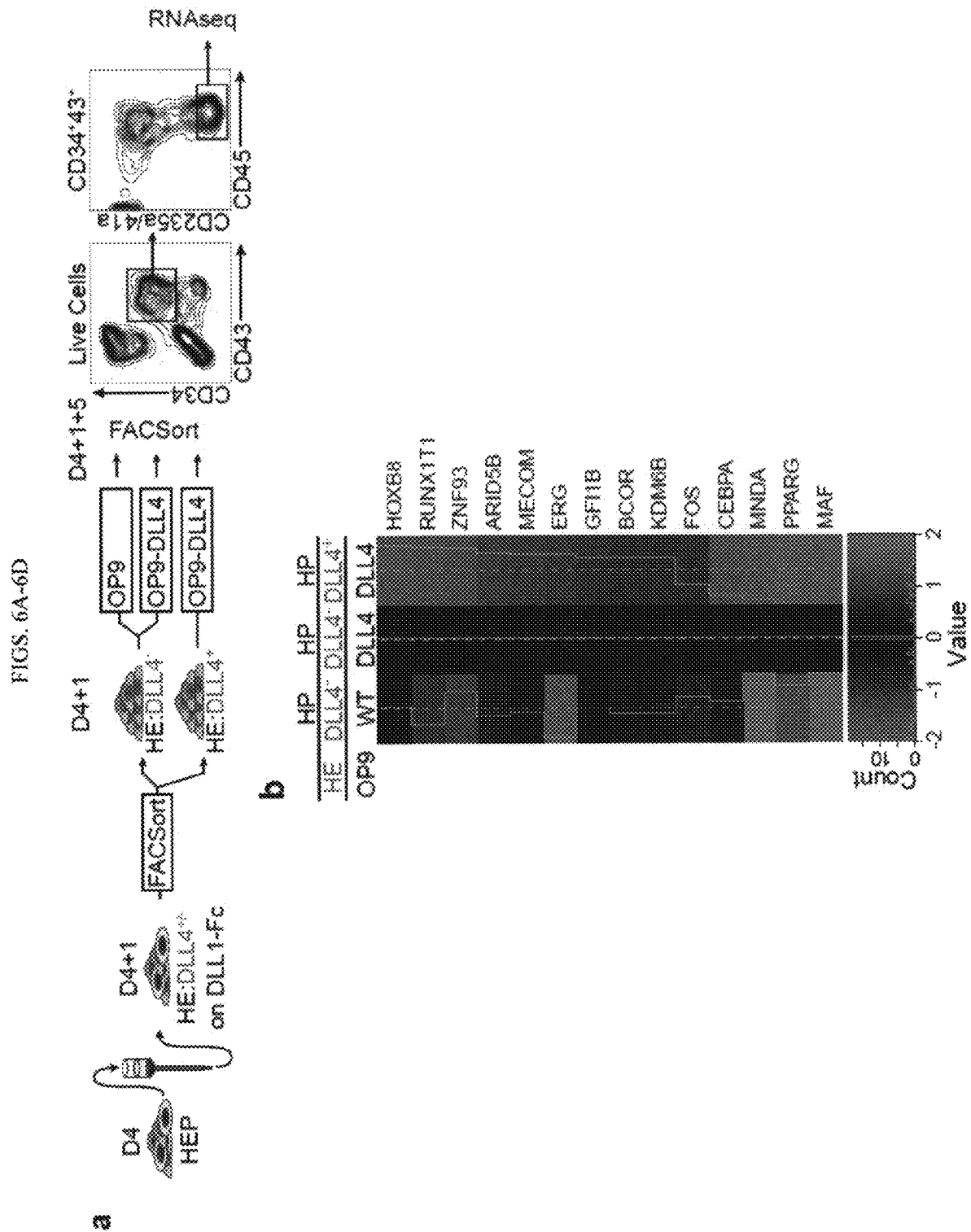
Figures 6A, 6B, 6C, 6D:
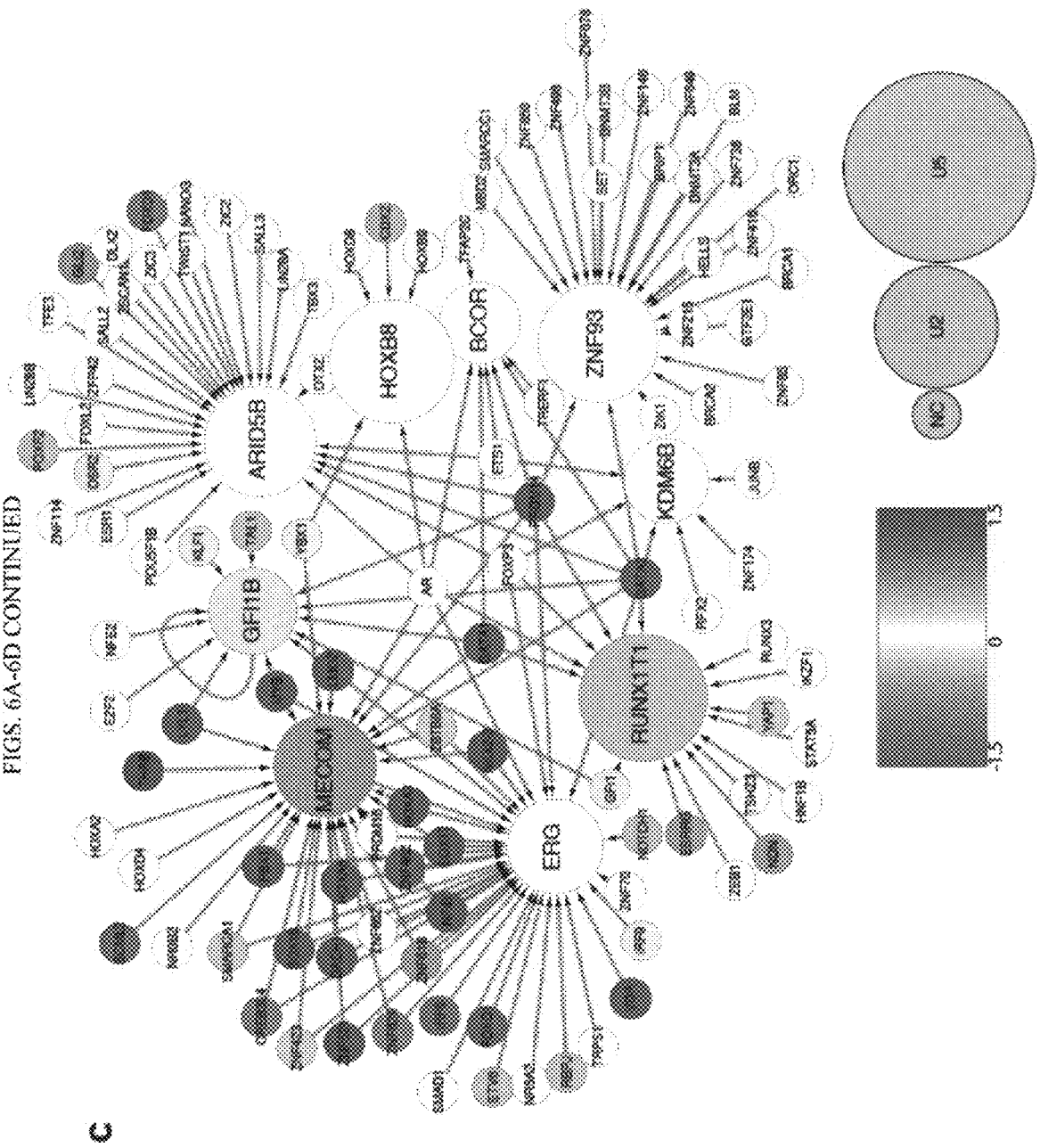
Figures 6A, 6B, 6C, 6D:
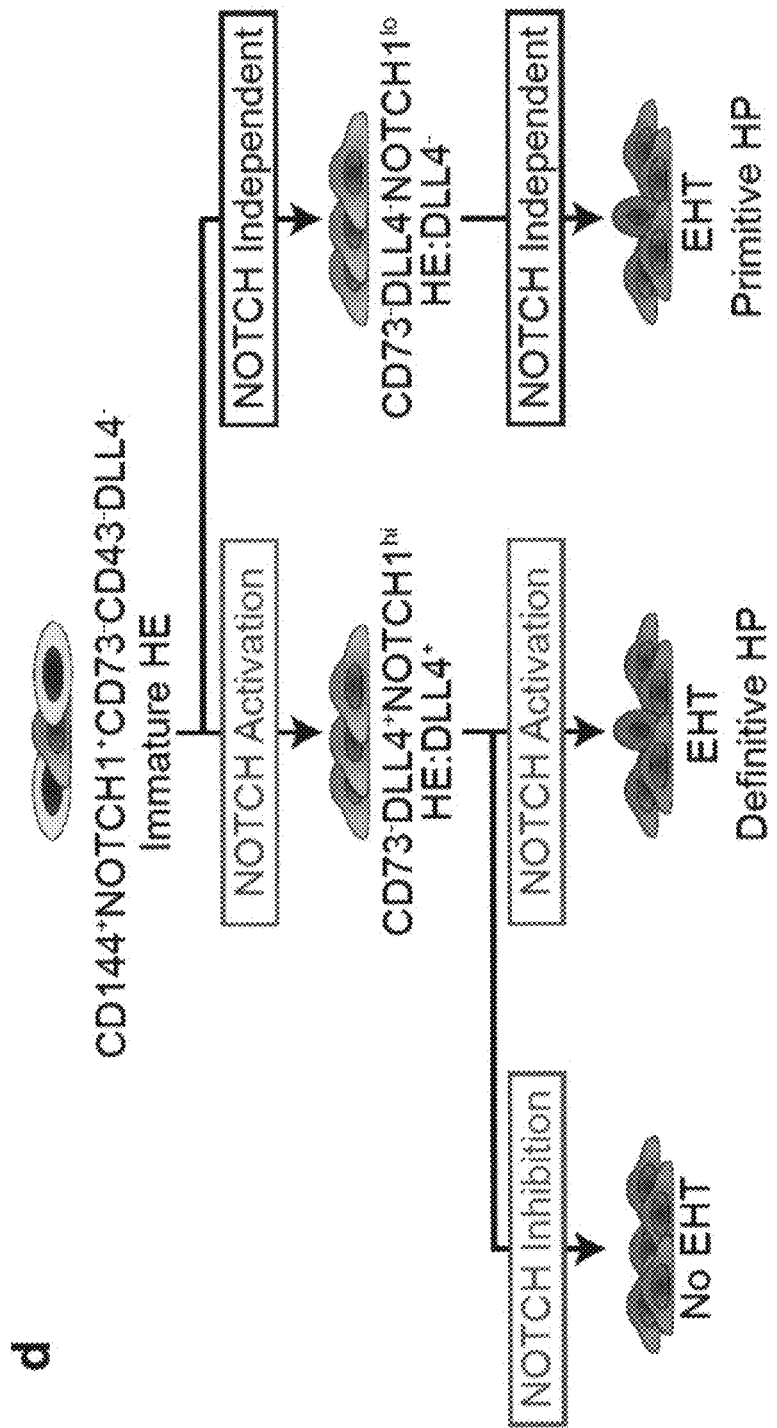

FIG. 13 shows heat map demonstrating expression of NOTCH signaling associated and arterial genes in immature D4 HE, D5 HE:DLL4+ and HE:DLL4−, and hematopoietic progenitors CD34+CD45+ generated from D5 HE:DLL4+ and HE:DLL4− on wild type OP9 or OP9-DLL4 as depicted in FIG. 6a. Log 2-transformed Transcripts Per Million (log 2(TPM)) are used for color mapping. The color gradient is set to reflect highly expressed genes as red, non-expressed genes as green and genes expressed at 30 tpm as black.

FIG. 14 shows a table reciting antibodies used in the Examples.

FIG. 15 shows a table reciting the fluorescent reagents used in the Examples.

FIG. 16 shows a table reciting the primers used for qRT-PCT in the Examples.

DETAILED DESCRIPTION OF THE INVENTION

The present disclosure demonstrates methods that allow for the promoting of arterial hemogenic progenitors by NOTCH activation from immature CD144+CD43−CD73− HE and post-transition expansion of blood cells.

Figures 4A, 4B, 4C, 4D, 4E:
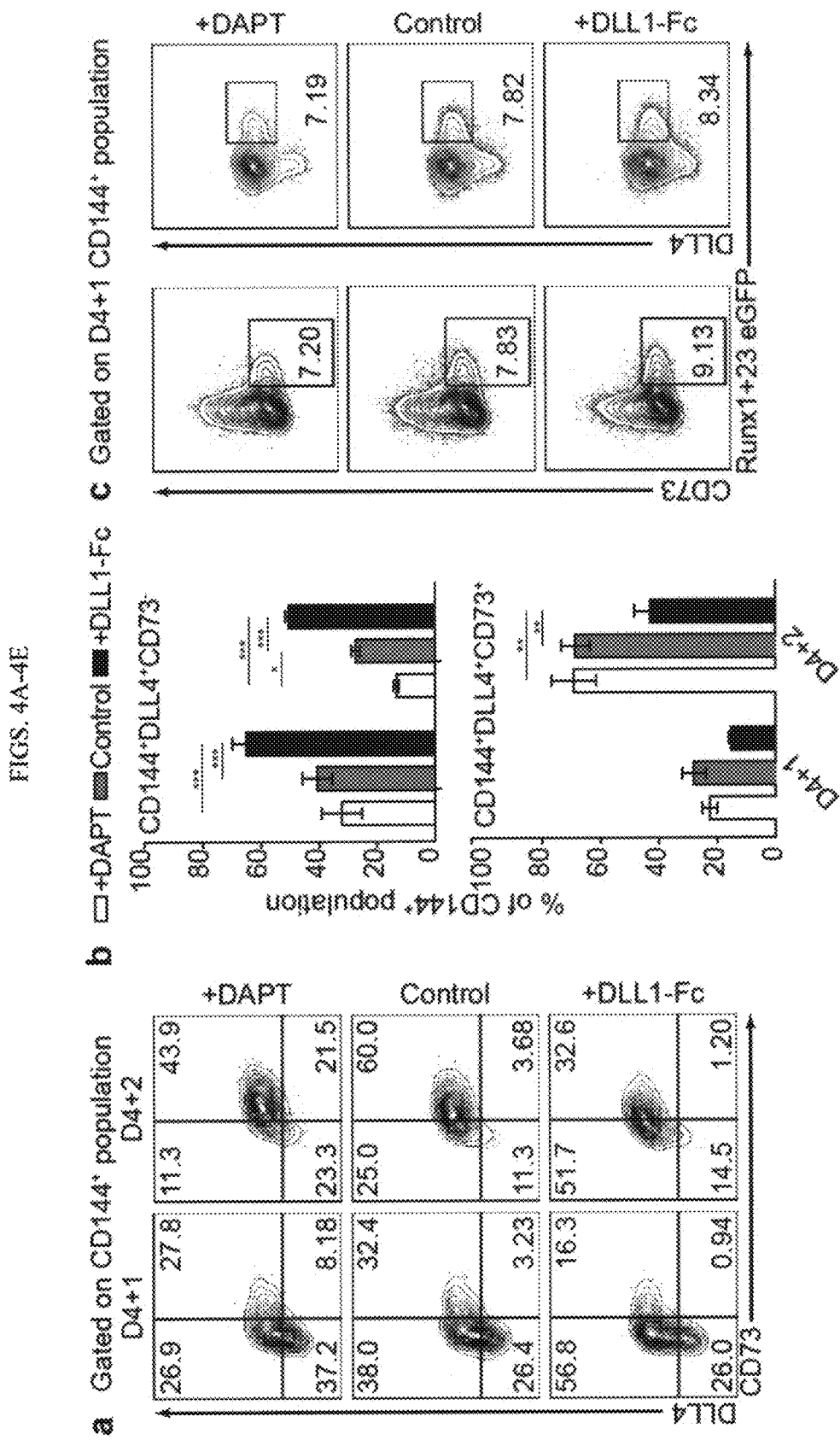

CD144+CD43−CD73− hemogenic endothelial (HE) cells on day 4 of differentiation are immature or primordial hemogenic endothelial cells which express HAND1. The immature CD144+CD43−CD73− hemogenic endothelial (HE) cells are also referred to herein as D4 HE cells. Methods of producing and obtaining D4 HE are described in the Examples and description herein. This cell population of immature HE can be seen in FIG. 4E, showing expression of HAND1.

Generating autologous hematopoietic stem cells (HSCs) from pluripotent stem cells (PSCs) that can be precisely genetically modified with designer endonucleases, and subsequently clonally selected, represents a promising approach for novel patient-specific gene therapies. Although multiple studies were able to generate hematopoietic progenitors with HSC phenotype from PSCs, these cells failed to produce multilineage engraftment. By "failure to produce multilineage engraftment," we mean that the cells did not have the capacity to reconstitute the hematopoietic system when transplanted into immunocompromised murine host (i.e. to repopulate bone marrow and produce lymphoid, myeloid and erythromegakaryocytic cells for more than 6 weeks post-transplantation). Thus, identification of key elements of cellular and molecular programs that reproduce in vitro the proper specification of HSCs would be essential to overcome current roadblocks on the way to de novo HSC generation.

We use the term "arterial specification" and "arterial type" interchangeably herein. The term arterial type hemogenic endothelial cells (AHE) of the present invention are CD144+CD43−CD73−DLL4+ HE that express high level of EFNB2 and NOTCH1 arterial markers and MYB gene required for definitive hematopoiesis. These cells have broad lympho-myeloid and definitive erythroid potentials.

During development, HSCs emerge by budding from hemogenic endothelium (HE) lining arterial vessels, most robustly from the ventral wall of the dorsal aorta. (See Bertrand, J. Y., Chi, N.C., Santoso, B., Teng, S., Stainier, D. Y., and Traver, D. (2010); Haematopoietic stem cells derive directly from aortic endothelium during development. Nature 464, 108-111; Dzierzak, E., and Speck, N. A. (2008)); Of lineage and legacy: the development of mammalian hematopoietic stem cells. Nat Immunol 9, 129-136; Medvinsky, A., Rybtsov, S., and Taoudi, S. (2011); Embryonic origin of the adult hematopoietic system: advances and questions. Development 138, 1017-1031.)

In the present invention, we disclose that NOTCH activation promotes EHT (endothelial to hematopoietic transition) from CD144+CD43−CD73− HE and post-transition expansion of blood cells. We have also found that NOTCH induces the arterial type CD144+CD43−CD73−DLL4+ HE (AHE) that express high level of EFNB2 and NOTCH1 arterial markers and MYB gene required for definitive hematopoiesis.

Definitive hematopoiesis produces the entire spectrum of adult-type erythro-myeloid progenitors (EMP), lymphoid cells and cells capable of limited engraftment and HSCs with capacity of long-term repopulation of an adult recipient. Definitive-type hematopoietic progeny with adult-like characteristics are CD144+CD43−CD73−DLL4+ HE that express high level of EFNB2 and NOTCH1 arterial markers and MYB gene. These definitive-type hematopoietic progeny with adult-like characteristics are cells able to give rise to hematopoietic progeny, such as platelet-producing megakaryocytes, adult-globin expressing erythrocytes, multipotential granulocyte/erythrocyte/megakaryocyte/macrophage colony forming cells (CFC-GEMM) and T-lymphocytes.

As described in the Examples, using transgenic reporter H1 human embryonic stem cell (hESC) line in which RUNX1+23 enhancer mediates GFP expression, we found that only DLL4+ HE demonstrated enhancer activity which is typically found in HE at sites of definitive hematopoiesis in mouse and zebra fish embryos (Swiers et al 2013, Tamplin et al 2015s). Hematopoiesis from CD144+CD43−CD73−DLL4+ AHEs requires stroma and is strictly dependent on NOTCH activation.

It is important to note that one aspect of the present invention comprises exposing the CD144+CD43−CD73−DLL4+ AHE to a sufficient amount of a NOTCH activation agent such that the AHE undergo endothelial-to-hematopoietic transition and produce definitive-type hematopoietic progeny with adult-like characteristics. Without sufficient NOTCH activation, the AHE cannot undergo endothelial-to-hematopoietic transition. In one embodiment of the present invention, one may wish to collect the hematopoietic progenitors and place them into specialized differentiation conditions to generate hematopoietic progeny, such as platelet-producing megakaryocytes, adult-globin expressing erythrocytes, CFC-GEMM and T-lymphocytes.

The present invention allows clear commercial advantages. Current methods of generating hematopoietic progenitors from human PSCs do not efficiently produce adult-type hematopoietic progenitors. Many of the hematopoietic progeny are not adult-type and have limited lymphoid potential and maintain embryonic-globin expression in erythrocytes. Here, we describe a method that generates definitive-type (adult-type) hematopoietic progenitors that give rise to progeny with increased T-lymphocyte potential and erythrocytes that express adult-globins. This technology allows us to derive the arterial hemogenic endothelial precursor to facilitate the production of definitive hematopoietic stem cells from human PSCs.

In summary, our disclosure reveals that the activation of NOTCH allows for specification of the arterial type of definitive HE that is the proper precursor for HSC formation in the embryo.

Cells of the Present Invention

In one embodiment, the present invention is a population of arterial hemogenic endothelium cells (AHE) that are CD144+CD43−CD73−DLL4+ HE. Preferably, the cells express high level of EFNB2 and NOTCH1 arterial markers and MYB gene required for definitive hematopoiesis. These cells have broad lympho-myeloid and definitive erythroid potentials.

The present invention involves the creation of cells with definitive potential. Definitive erythroid potential includes the ability to generate red blood cells that express increased levels of adult-type alpha- and beta-globin expression, while hematopoietic progenitors with only primitive erythroid potential only generate erythrocytes that express embryonic (zeta and epsilon) globins. This invention discloses that AHE-derived hematopoietic progenitors have increased potential to generate erythrocytes with increased adult-type alpha- and beta-globins.

Preferably, the population is at least 90%, at least 95% or at least 99% pure.

The ability to specifically derive arterial hemogenic endothelial precursors also allows for the increase in the ability to in vitro differentiate the AHEs into T cells. AHEs derived by the present methods have at least a four (4)-fold increase in T cell potential than prior methods of in vitro differentiation.

Methods of the Present Invention

In one embodiment, the present invention is a method of creating AHE cells. In another embodiment, the present invention is a method of creating various kinds of hematogenic cells by differentiation of AHE cells. The AHE cells in these embodiments may be differentiated from pluripotent stem cells (PSCs) or from AHE isolated from mammalian tissues. Preferred examples of differentiated cells include platelet-producing megakaryocytes, adult-globin expressing erythrocytes, or T-lymphocytes.

The Example below describes exemplary methods to create the AHE of the present invention. However, these methods may be modified, with one or more of the modifications listed below, and still be within the scope of the invention.

As Example 1 discloses, we utilized a modified version of the serum- and feeder-free differentiation system described previously (Uenishi et al., 2014) where we identified developmental stage equivalencies to in vivo development that can be identified by cell-surface antigens and functional assays on specific days of differentiation: Day 2 APLNR$^+$ PDGFRα$^+$ Primitive Mesoderm (D2 PM), Day 4 KDR$^{hi}$PDGFRα$^{low/-}$CD31$^-$ Hematovascular Mesoderm Precursors (D4 HVMP), Day 4 and 5 CD144$^+$CD43$^-$CD73$^-$ Hemogenic Endothelial cells (D4 or D5 HE), and Day 8 CD34$^+$CD43$^+$ Hematopoietic Progenitors (D8 HP) (Choi et al., 2012b). During differentiation, we found that the Notch1 receptor is first expressed at high levels uniquely on D4 HEPs while the Notch ligand, DLL4, is first expressed on D5 within the CD144+ (VE-Cadherin) population (FIG. 1A) suggesting that NOTCH signaling in hPSC cultures is established at the time of HE formation.

Therefore, in one embodiment of the present invention, one will isolate D4 HE, preferably by simple magnetic enrichment of CD31+ cells since at this stage, the CD31+ population is entirely CD144+CD43−CD73− (Choi et al., 2012b; Uenishi et al., 2014)). D4 HEs can be isolated by the way disclosed in Example 1 and other equivalent ways, such as FACS.

In some embodiments, the defined conditions comprise culturing the cells with stromal cells, preferably OP9 cells.

In another embodiment, the defined conditions in which PSCs are differentiated to the immature HE cells include the conditions described in Uenishi et al. 2014, incorporated by reference in its entirety. In brief, in one embodiment, the defined conditions and differentiating step comprises (1) exposing the stem cells to a xenogen-free and serum albumin-free mixture comprising components of about 25 ng/ml to about 50 ng/ml FGF2, high levels of BMP4 of at least 50 ng/ml, low levels of Activin A of less than 15 ng/ml, and about 1 mM to about 2 mM LiCl under hypoxic conditions for a period of about two days to form a population of EMHlin-KDR+APLNR+PDGFRalpha+primitive mesoderm cells without the formation of embryoid bodies or coculture with stromal cell lines and (2) exposing the cells at the hematovascular mesoderm stage of step (1) to a mixture comprising components FGF2, VEGF, IL6, SCF, TPO, and IL3 for about one day to achieve formation of CD144+CD73−CD235a/CD43− immature hemogenic endothelial, and (3) detecting and isolating the CD144+ CD73−CD235a/CD43− HE from culture of step (2).

The isolated D4 HE cells may be plated onto an NOTCH activation agent, such as immobilized Notch ligands, to activate NOTCH signaling (Hadland et al., 2015; Ohishi et al., 2002) (See FIG. 1B). Activation of NOTCH signaling by any means is suitable; for example, overexpression of the active form of NOTCH receptor or NOTCH ligands. See Bigas, A., D'Altri, T., and Espinosa, L. (2012). The Notch pathway in hematopoietic stem cells. Curr Top Microbiol Immunol 360, 1-18.

Bigas, A., and Espinosa, L. (2012). Hematopoietic stem cells: to be or Notch to be. Blood 119, 3226-3235.

Butko, E., Pouget, C., and Traver, D. (2016). Complex regulation of HSC emergence by the Notch signaling pathway. Dev Biol 409, 129-138.

Lu, Y F., Cahan, P., Ross, S., Sahalie, J., Sousa, P M., Hadland, B. K., Cai, W., Serrao, E., Engelman, A N., Bernstein, I D., Daley, G Q. (2016) Engineered Murine HSCs Reconstitute Multi-lineage Hematopoiesis and Adaptive Immunity. Cell Report 17, 3178-3192

Examples of suitable Notch ligands include DLL1-Fc (which has been described in other papers as Delta1ext-IgG), Jag1 ligand, and DLL4 (see Example 1)). Other examples would include an immobilized synthetic molecule that can bind to NOTCH and sufficiently activate the NOTCH receptor and the ectopic expression of the active, intracellular domain of NOTCH1 (Notch-ICD).

We confirmed by western blot analysis of the active form of Notch1, Notch-ICD, and qPCR analysis of the downstream Notch1 target gene, HES1, by qPCR, these respective conditions efficiently activated NOTCH signaling (FIG. 1C). Kinetic analysis of CD144 (endothelial marker) and CD43 (hematopoietic marker) from D4+1 to D4+4 reveals a significant increase in hematopoiesis in the NOTCH activation condition, and a significant decrease in hematopoiesis in the NOTCH inhibition condition compared to the control condition. We also found that there was a significant increase in the total cell number, particularly the hematopoietic progenitors in the NOTCH activation condition (FIG. 1E, F). The effect of DLL1-Fc on hematopoiesis increased as the concentration of immobilized DLL1-Fc and cell density increased. Similar results were obtained when day 4 HEPs were cultured in serum-containing medium on wild type or DLL4-expressing OP9 stromal cells.

In another embodiment of the present invention, one would differentiate AHE cells into another hematopoietic cell type. Suitable hematopoietic cell types include, T lymphocytes, B-cell, definitive (adult-type) erythrocytes, myeloid progenitors and mature myelomonocytic cells. There are numerous prior art examples of differentiation protocols.

Another embodiment provides a method of differentiating the AHE cells into T cells by culturing the AHEs in T cell differentiation medium with sufficient amount of NOTCH activating agent in order to differentiate the cells into T lymphocytes (T cells). Suitable conditions for differentiating T cells are known in the art. The T cells can be identified as CD4+CD8+. In some embodiments, the T cells are identified as CD7+CD5+, CD8+CD4+, or a combination thereof (CD7+CD5+ and CD8+/CD4+).

In yet another embodiment, the disclosure provides a method of obtaining a cellular composition comprising more than 95% arterial-type hemogenic endothelium (AHE) cell population, comprising the steps of a. differentiating human pluripotent stem cells (hPSCs) for five days in defined conditions to induce formation of CD144+CD43−CD73− Dll4+ arterial HE; and b. detecting and isolating a cell fraction being characterized by CD144+CD43−CD73− DLL4+ phenotype. The defined conditions necessary to differentiate the hPSCs are known in the art, for example, as described in Vodyanik et al. 2005 and Uenishi et al. 2014, the contents of which are incorporated by reference and detailed above. However, other suitable methods known in the art can be used.

In some embodiments, the defined conditions comprise culturing the cells with stromal cells, preferably OP9 cells.

In another embodiment, the defined conditions include the conditions described in Uenishi et al. 2014, incorporated by reference in its entirety. In brief, in one embodiment, the defined conditions and differentiating step comprises (1) exposing the stem cells to a xenogen-free and serum albumin-free mixture comprising components of about 25 ng/ml to about 50 ng/ml FGF2, high levels of BMP4 of at least 50 ng/ml, low levels of Activin A of less than 15 ng/ml, and about 1 mM to about 2 mM LiCl under hypoxic conditions for a period of about two days to form a population of EMHlin-KDR+APLNR+PDGFRalpha+primitive mesoderm cells without the formation of embryoid bodies or coculture with stromal cell lines and (2) exposing the cells at the hematovascular mesoderm stage of step (1) to a mixture comprising components FGF2, VEGF, IL6, SCF, TPO, and IL3 for about one day to achieve formation of CD144+CD73−CD235a/CD43− immature hemogenic endothelial, and (3) detecting and isolating the CD144+ CD73−CD235a/CD43− HE from culture of step (2).

In some embodiments, after step (a), the cells are combined with a detecting agent specific for different cell surface markers, for example, CD144, CD43, CD73 and DLL4, and wherein the detecting agents with different labels are used to separate the cell fraction characterized by CD144+CD43− CD73−DLL4+ phenotype. In a preferred embodiment, the detecting agents are antibodies, for example, monoclonal antibodies with different labels that are specific to the cell surface markers. In an embodiment, the monoclonal antibodies are labeled with different fluorescent labels.

In some embodiments, the different labels are different fluorescent labels or fluorophores. Suitable fluorescent labels or fluorophores are known in the art and include, but are not limited to, for example, dyes green fluorescent protein (GFP), red fluorescent protein (RFP), CFP, Alexa Fluor (available from ThermoFisherScientific, Waltham Mass.), including Alexa Fluor 350, Alexa Fluor 405, Alexa Fluor 488, Alexa Fluor 532, Alexa Fluor 546, Alexa Fluor 555, Alexa Fluor 568, Alexa Fluor 594, Alexa Fluor 647, Alexa Fluor 680, Alexa Fluor 750, BODIPY FL, Coumarin, Cyanine 3 (Cy3), Cyanine 5 (Cy5), Fluorescein (FITC), Oregon Green, Pacific Blue, Pacific Green, Pacific Orange, Tetramethylrhodamine (TRITC), Texas Red, Super Bright dyes including Super Bright 436, Super Bright 600, Super Bright 645, Super Bright 702, among others. Suitable fluorescently labeled detecting agents (including antibodies and monoclonal antibodies) are known in the art and not limited herein. Suitable methods of detection and isolation are known in the art and include, but are not limited to, FACSorting.

In another embodiment of the present invention, one would isolate AHE cells from mammalian cells and further differentiate the AHE as described above.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit's interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim.

The following non-limiting examples are included for purposes of illustration only, and are not intended to limit the scope of the range of techniques and protocols in which the compositions and methods of the present invention may find utility, as will be appreciated by one of skill in the art and can be readily implemented. The present invention has been described in terms of one or more preferred embodiments, and it should be appreciated that many equivalents, alternatives, variations, and modifications, aside from those expressly stated, are possible and within the scope of the invention.

EXAMPLES

Example 1: NOTCH Signaling Specifies Arterial-Type Definitive Hemogenic Endothelium from Human Pluripotent Stem Cells This Example demonstrates that NOTCH activation in hPSC-derived immature HE progenitors leads to formation of $CD144^+CD43^-CD73^-DLL4^+Runx1+23$-$GFP^+$ arterial-type HE which requires NOTCH signaling to undergo endothelial-to-hematopoietic transition and produce definitive lympho-myeloid and erythroid cells. These findings demonstrate that NOTCH-mediated arterialization of HE is an essential prerequisite for establishing definitive lympho-myeloid program and suggest that exploring molecular pathways that lead to arterial specification may aid in vitro approaches to enhance definitive hematopoiesis from hPSCs.

During in vivo development, HSCs emerge by budding from hemogenic endothelium (HE) lining arterial vessels, primarily from the ventral wall of the dorsal aorta[5-7]. NOTCH signaling is essential for arterial specification and generation of HSCs[8-11]. $Notch1^{-/-}$, $Dll4^{-/-}$ and $Rbpjk^{-/-}$ mice, which are embryonic lethal, have severe impairment in arterial vasculogenesis, fail to develop the dorsal artery[10, 12, 13] and lack intra-embryonic hematopoiesis. NOTCH signaling is also required for the acquisition of arterial identity in extraembryonic vessels, including the yolk sac vasculature[14, 15]. Interestingly, definitive hematopoietic progenitors with lymphoid potential in the yolk sac, umbilical cord and vitelline vessels only emerge within the arterial vasculature[16, 17]. In contrast, the primitive extraembryonic wave of erythropoiesis and the first wave of definitive yolk sac erythro-myelopoiesis (EMP), which lack lymphoid potential, are not NOTCH-dependent or specific to arterial vessels[10, 13, 16, 18-20]. The lack of venous contribution to HSCs along with the shared requirements of Notch, VEGF, and Hedgehog signaling for both arterial fate acquisition and HSC development[21-25], led to the hypothesis that arterial specification could be a critical prerequisite for HSC formation. However, a direct progenitor-progeny link between arterial specification and definitive hematopoiesis has never been demonstrated. Moreover, demonstration in recent studies that HE represents a distinct $CD73^-$ lineage of endothelial cells[26, 27] and that hematopoietic specification is initiated at the HE stage [28-30] raises the question whether NOTCH signaling at arterial sites creates a permissive environment for HSC development following endothelial-to-hematopoietic transition (EHT), or that arterial specification per se is required for HE to become HSCs. Although, recent studies have demonstrated that NOTCH activation induces arterialization of $CD73^+$ non-HE[27], and that NOTCH inhibition with DAPT reduces production of $CD45^+$ cells from $CD34^+CD43^-CD73^-$ HE progenitors[27, 31], the effect of NOTCH signaling on HE specification has never been explored.

Here, using a chemically defined human pluripotent stem cell (hPSC) differentiation system combined with the use of DLL1-Fc and the small molecule DAPT to manipulate NOTCH signaling following the emergence of the well-defined $CD144^+CD43^-CD73^-$ population of HE during EHT, the inventors discovered that NOTCH activation leads to the formation of arterial-type $CD144^+CD43^-CD73^-DLL4^+$ HE (AHE) that expresses arterial markers and possesses definitive lympho-myeloid and erythroid potentials. Using a transgenic reporter H1 hESC line in which the Runx1+23 enhancer mediates eGFP expression, the inventors found that only $DLL4^+$, and not $DLL4^-$ HE cells, demonstrated enhancer activity that is typically found in HE at sites of definitive hematopoiesis in mouse and zebra fish embryos.

Hematopoiesis from $CD144^+CD43^-CD73^-DLL4^+$ AHE required stroma and was strictly dependent on NOTCH activation. In contrast, NOTCH modulation has limited effect on EHT from the HE fraction that remains $DLL4^-$ following NOTCH activation, indicating that definitive hematopoietic activity segregates to AHE. Together, this Example established a direct progenitor-progeny link between arterialization of HE and embryonic definitive hematopoiesis and revealed that NOTCH-mediated induction of AHE is an important prerequisite for establishing the definitive hematopoietic program from hPSCs.

Results

Immobilized DLL1-Fc Increases NOTCH Signaling in Hemogenic Endothelial Cells and Increases Hematopoietic Activity In order to determine the direct effect of NOTCH signaling on hematoendothelial differentiation from hPSCs, we utilized a modified version of the serum- and feeder-free differentiation system described previously[35] where the inventors identified developmental stage equivalencies to in vivo development that can be identified by cell-surface antigens and functional assays on specific days of differentiation: Day 2-3 APLNR$^+$PDGFRα$^+$ Primitive Mesoderm (D2 or D3 PM), Day 4 KDR$^{hi}$PDGFRα$^{hi}$PDGFRα$^{low/-}$CD31$^-$ Hematovascular Mesoderm Precursors (D4 HVMP), Day 4 and 5 CD144$^+$CD43$^-$CD73$^-$ Hemogenic Endothelial Cells (D4 or D5 HE), and Day 8 CD34$^+$CD43$^+$ Hematopoietic Progenitors (D8 HP)[26, 35]. During differentiation, the inventors found that the NOTCH1 receptor is first highly expressed on D4 HE cells while the NOTCH ligand, DLL4, is first expressed on D5 within the CD144$^+$ (VE-Cadherin) population (FIG. 1a) suggesting that NOTCH signaling in hPSC culture is established at the time of HE formation.

Figures 7A, 7B, 7C, 7D, 7E, 7F:
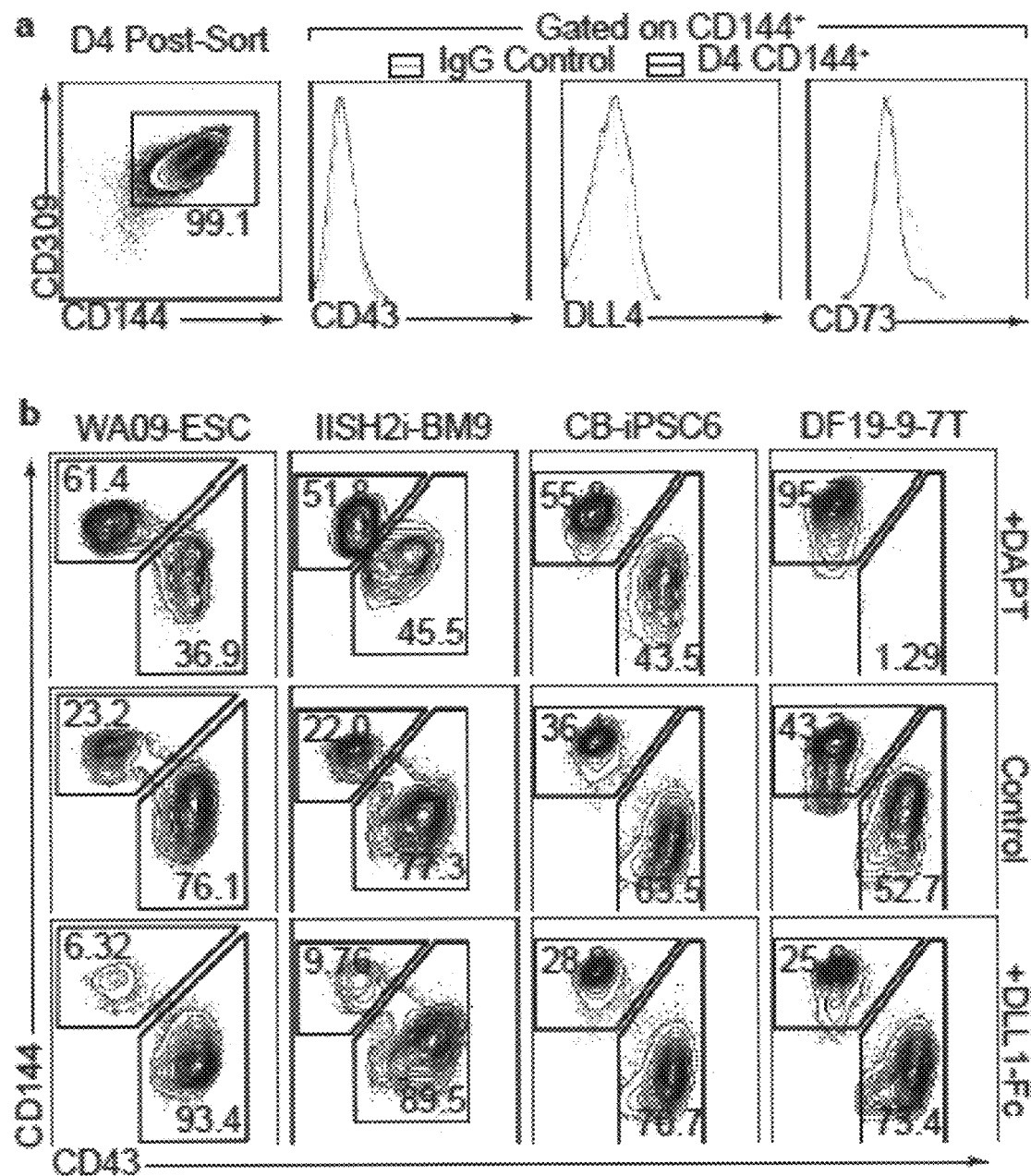
Figures 7A, 7B, 7C, 7D, 7E, 7F:
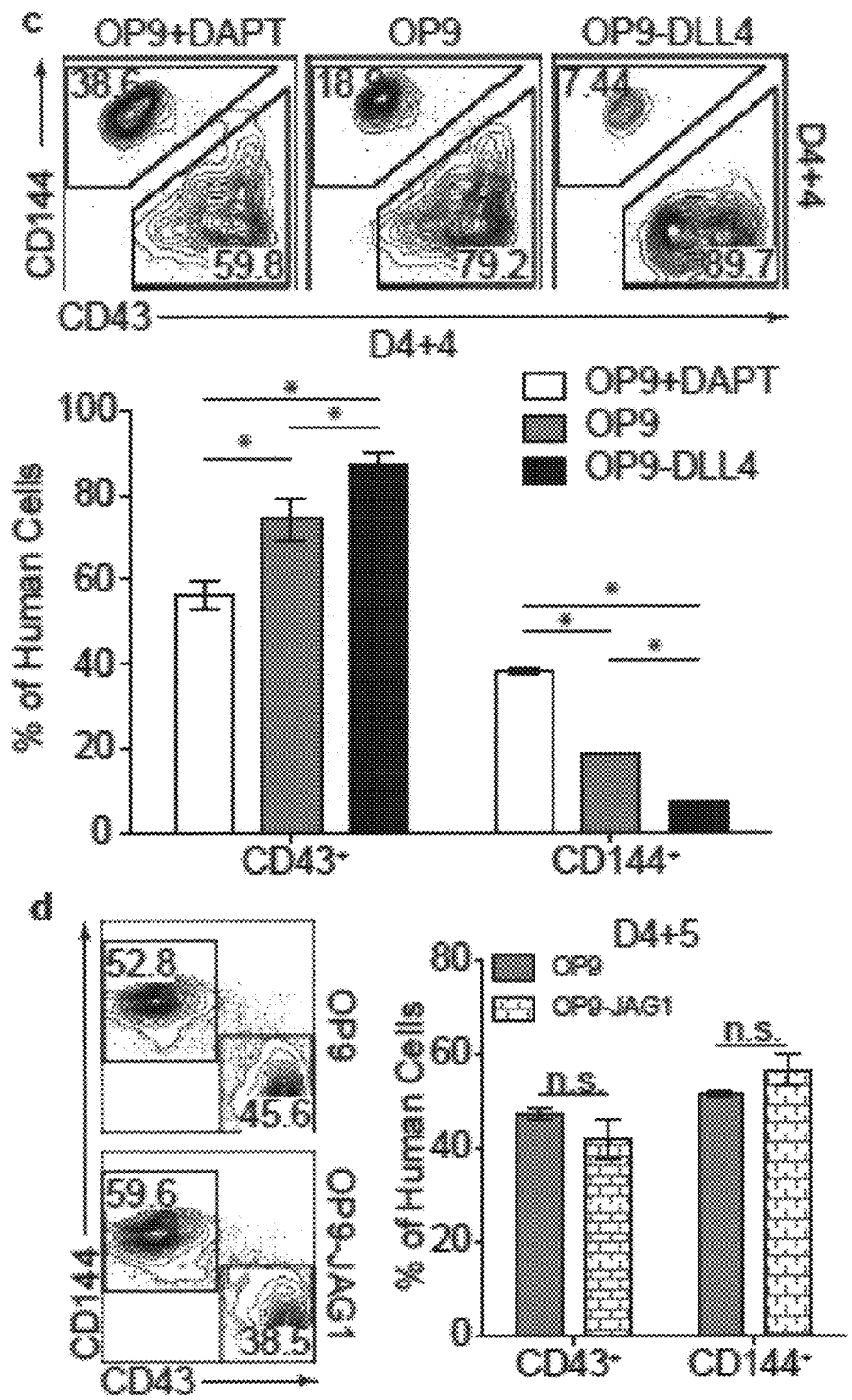
Figures 7A, 7B, 7C, 7D, 7E, 7F:
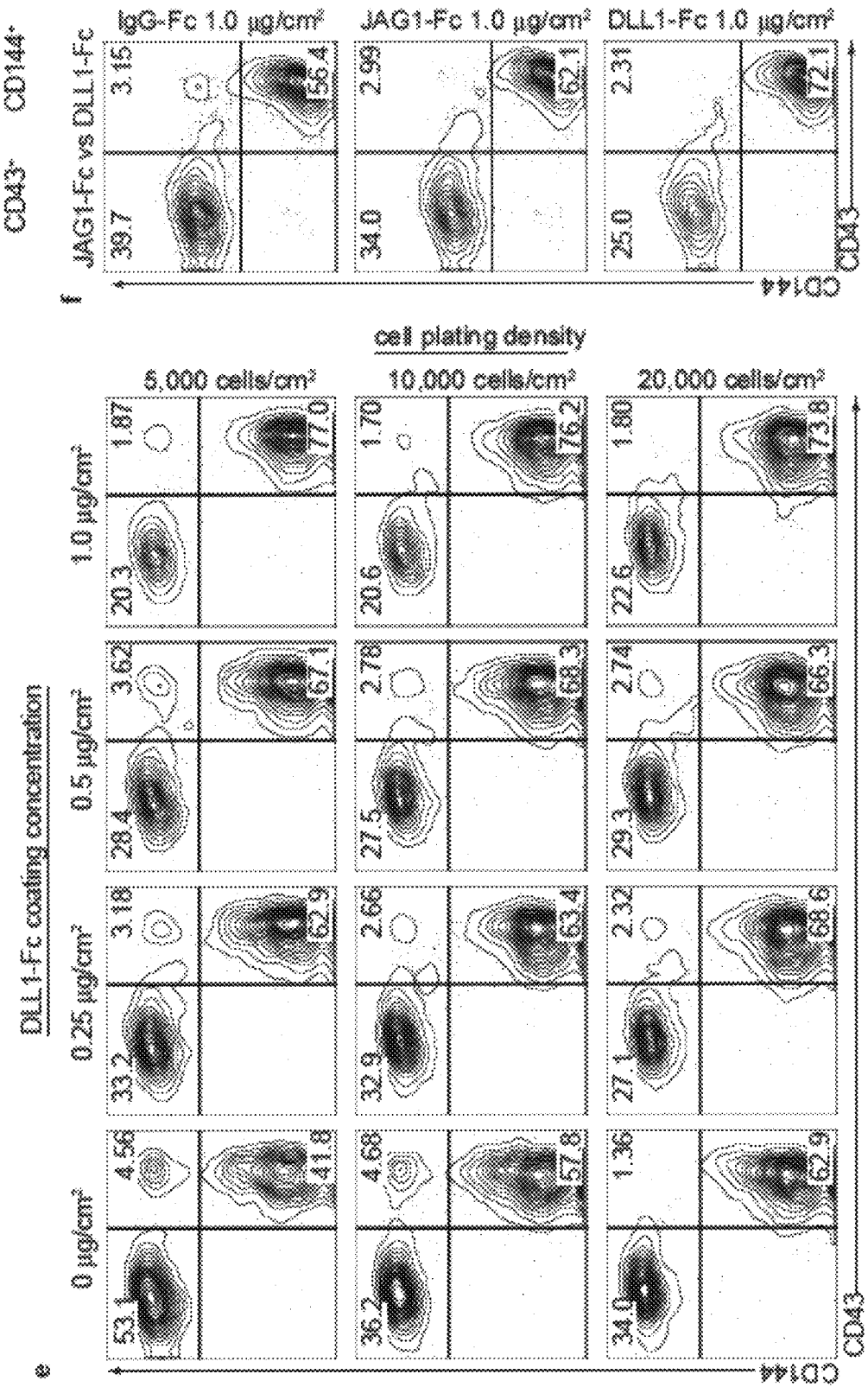

Following the establishment of optimal conditions for EHT culture in defined feeder- and serum-free conditions, the inventors isolated D4 HE by magnetic enrichment of CD31$^+$ cells, since at this stage (FIG. 1A), the CD31$^+$ population is entirely CD144$^+$CD43$^-$CD73$^-$DLL4$^-$ (FIG. 7A). Isolated D4 HE cells were cultured either in control conditions, with the small molecule gamma-secretase inhibitor, DAPT, to inhibit NOTCH signaling, or were plated onto the immobilized NOTCH ligand DLL1-Fc to activate NOTCH signaling (FIG. 1B). Confirmed by western blot analysis, the active form of NOTCH1, NOTCH:ICD, and qPCR analysis of the downstream NOTCH1 target gene, HES1, by qPCR, these respective conditions efficiently inhibited and activated NOTCH signaling (FIG. 1C, D). Kinetic analysis of CD144 (endothelial marker) and CD43 (hematopoietic marker) from D4+1 to D4+4 reveals a significant increase in hematopoiesis in the NOTCH activation condition and a significant decrease in hematopoiesis in the NOTCH inhibition condition, compared to control (FIG. 1E). These results were consistent with other hESC and hiPSC lines (FIG. 7B). In addition, similar results were obtained when D4 HE cells were cultured in serum-containing medium on wild type OP9 stromal cells or OP9 cells transduced with human DLL4 (OP9-DLL4; FIG. 7C). The inventors observed a significant increase in the total hematopoietic cell number in the NOTCH activation condition (FIG. 1F). The effect of DLL1-Fc on hematopoiesis increased as the concentration of immobilized DLL1-Fc and cell density increased (FIG. 7E). In contrast, culture of D4 HE on immobilized JAG1-Fc or OP9-JAG1 minimally affected hematopoiesis as compared to controls (FIGS. 7D and 7F), thereby suggesting suboptimal activation of NOTCH signaling by JAG1.

Figures 2A, 2B, 2C, 2D, 2E, 2F, 2G:
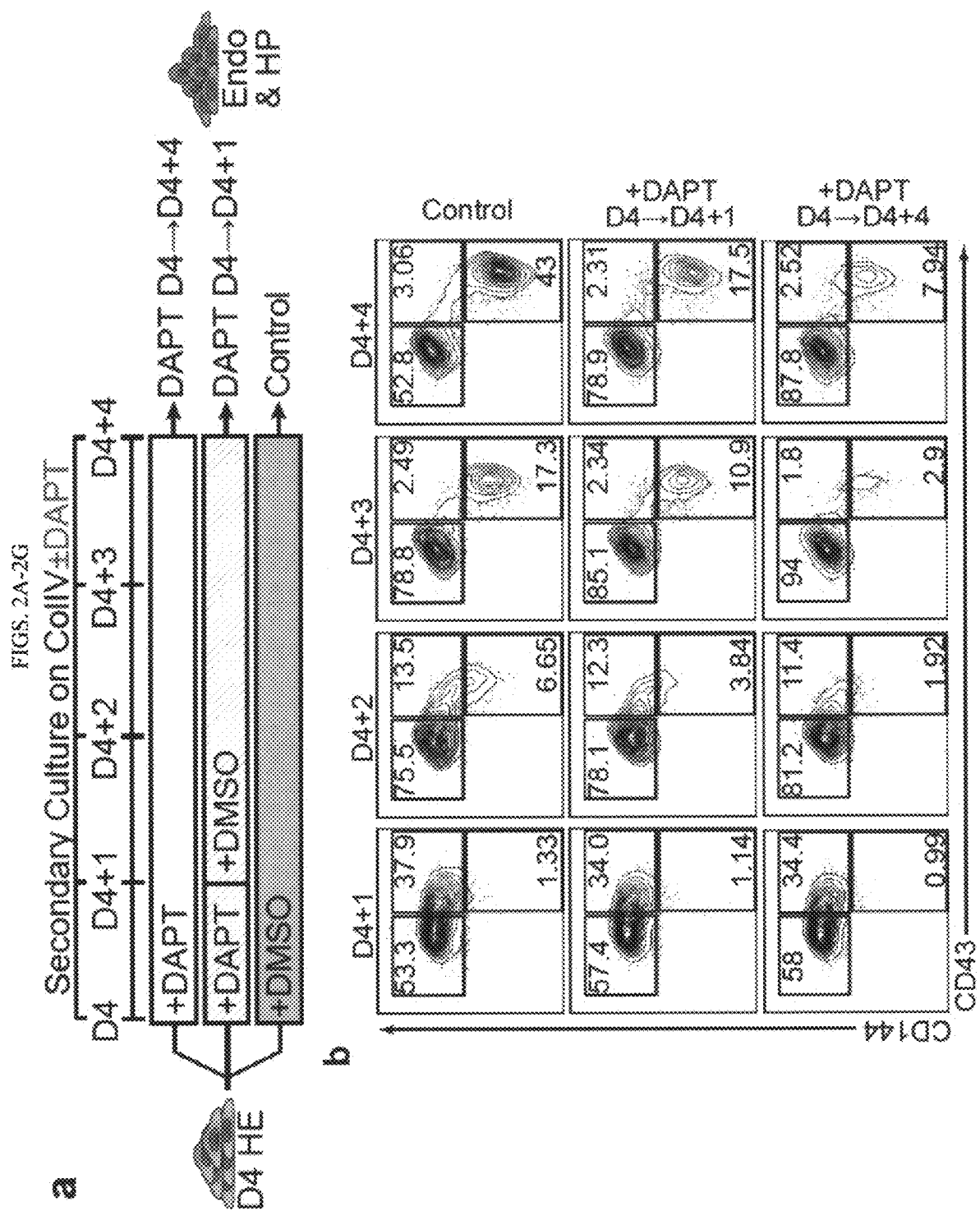
Figures 2A, 2B, 2C, 2D, 2E, 2F, 2G:
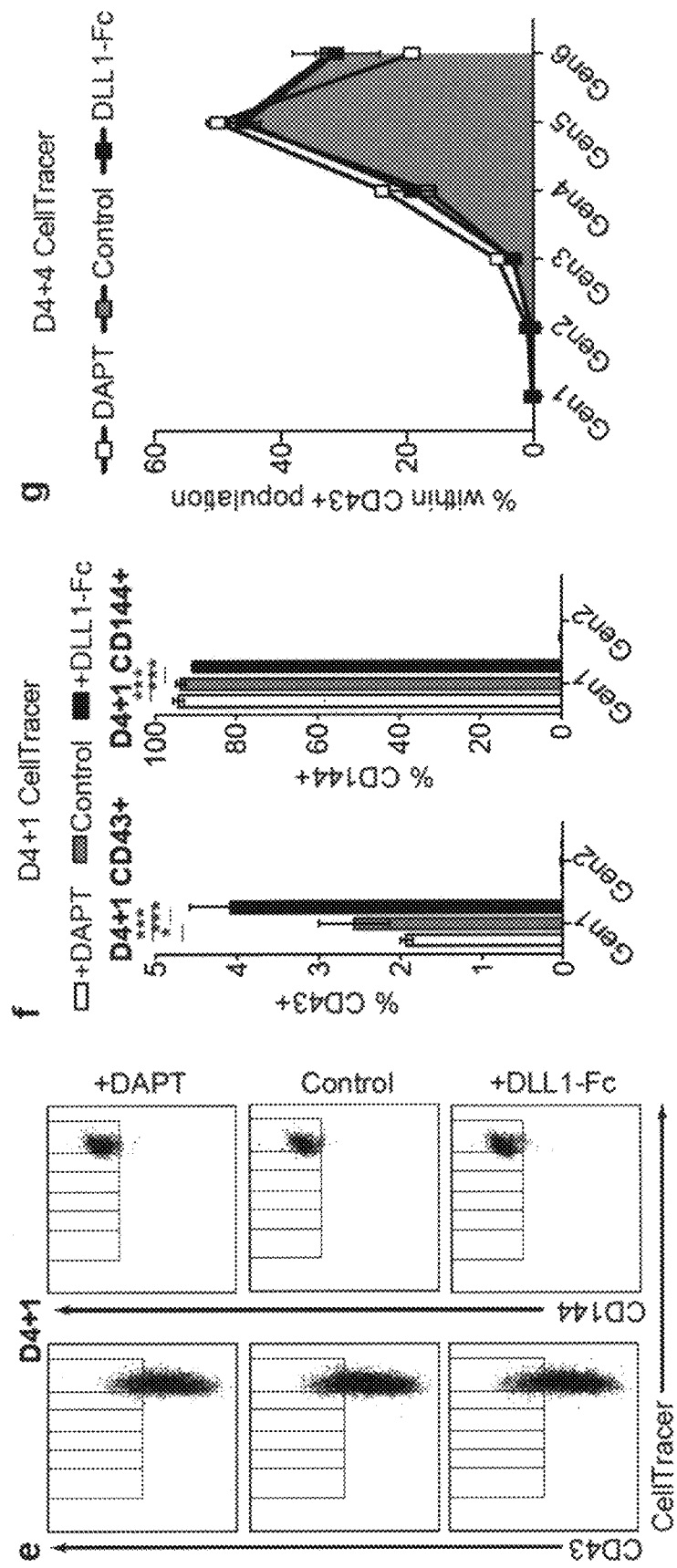

NOTCH Activation Facilitates Endothelial-to-Hematopoietic Transition in Hemogenic Endothelium The increase in hematopoiesis due to increased NOTCH signaling can be attributed to three reasons: 1) increased EHT, 2) increased hematopoietic expansion or 3) increased survival post-EHT. To evaluate these possibilities, the inventors isolated D4 HE cells and cultured them with DAPT for either 1 day during initiation of EHT (from D4 to D4+1), or throughout the entire culture (D4 to D4+4), followed by kinetic analysis of CD43 and CD144 expression on each day of the culture period (FIG. 2A). Following culture in defined conditions, HE weakly upregulate CD43 expression on D4+1, but retain flat endothelial morphology. Round CD43$^{hi}$ cells that have completed EHT appear after D4+2[38]. As shown in FIGS. 2B and 2C, HE treated for 24-hours with DAPT from D4 to D4+1 weakly express CD43 along with CD144 on D4+1, but fail to complete EHT efficiently, as evidenced by a significant drop in CD43$^{hi}$ CD144$^-$ cells on D4+2 through D4+4, although DAPT treatment throughout (D4 to D4+4) more profoundly decreased hematopoiesis.

To further verify that NOTCH activation affects EHT, the inventors also performed a single cell deposition assay of the D4 HE using the OP9 stromal cells and serum-containing medium which support hematoendothelial development from single cells. Using a DOX-inducible DLL4 OP9 cell line (OP9-iDLL4), D4 HE were deposited onto 96-well plates at three different conditions; OP9-iDLL4 with DAPT without DOX-pretreatment (NOTCH inhibition condition), OP9-iDLL4 with DMSO without DOX-pretreatment (control condition), and OP9-iDLL4 with DMSO with pretreatment of DOX (NOTCH activation condition). The inventors found that D4 HE in the NOTCH inhibition condition had a markedly decreased ratio of hematopoietic/endothelial colonies compared to D4 HE cells in the control condition. In contrast, the D4 HE in the NOTCH activation condition had substantially increased ratio of hematopoietic colonies compared to D4 HE in the NOTCH inhibition condition, and a slight increase compared to D4 HE in the control condition (FIG. 2D). Due to well-recognized fragility of hPSC-derived HE and survival after single cell sorting[1, 27], we found that only less than 40% of single cells formed endothelial/hematopoietic colonies. Nevertheless, the total number of colonies was consistent across each of the three NOTCH conditions, thereby indicating that the sorting experiments were not affected by differences in cell viability.

The inventors also stained the purified D4 HE before plating with CellTracer to track cell proliferation. When analyzed, the cells in each of the three NOTCH conditions on D4+1 showed a significant increase in the proportion of CD144$^+$CD43$^+$ to CD144$^+$CD43$^-$ cells within the first generation of cells in the NOTCH activation condition (+DLL-Fc), when compared to the NOTCH inhibition (+DAPT) condition. This result, in combination with the absence of a second generation on D4+1, suggests that the activation of NOTCH signaling at HE stage potentiate EHT initiation, but not proliferation (FIG. 2E, F). Assessment of cell proliferation on D4+4 with CellTracer in cultures treated with DAPT through D4+4 revealed no significant shift in distribution of CD43$^+$ cells within each generation (FIGS. 2G and 8A), consistent with the lack of NOTCH effect on post-EHT expansion. In addition, analysis of cell cycle in these cultures using EdU, demonstrated no differences in cycling CD43$^+$ cells in different conditions (FIG. 8B, C).

To evaluate whether NOTCH signaling affects apoptosis, the inventors performed Annexin V flow cytometric analysis of HE cultured with DAPT, DMSO or on DLL1-Fc on D4+4. As shown in FIGS. 9A and 9B, none of the conditions affected apoptosis of blood cells post-transition, suggesting that the difference in hematopoiesis from HE following manipulation of NOTCH signaling is not attributed to the NOTCH effect on cell survival.

Together, these results suggest that NOTCH activation at the HE stage facilitates EHT, but has minimal effect on expansion or survival of blood cells at post-EHT stage.

Figures 3A, 3B, 3C, 3D:
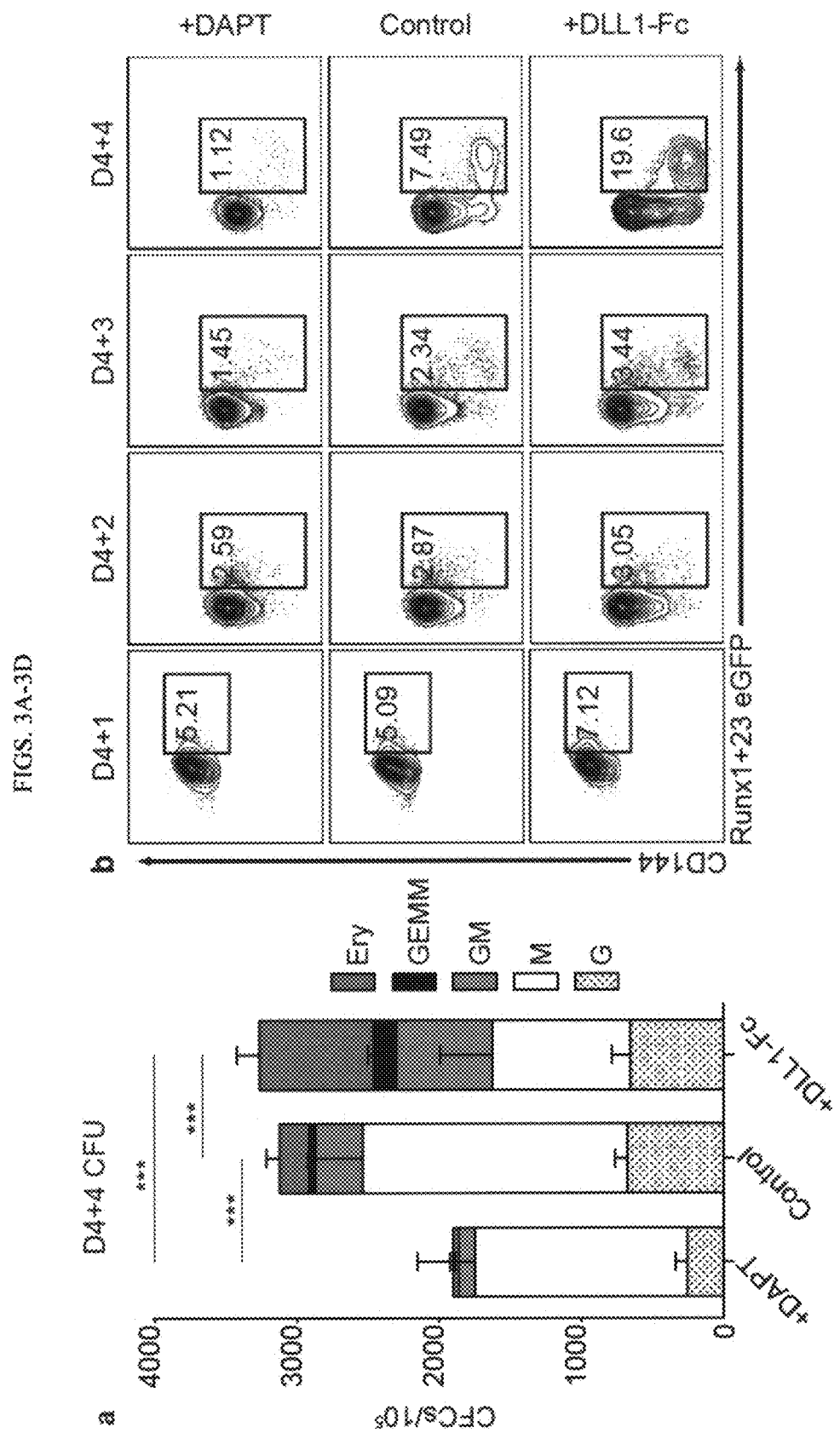
Figures 3A, 3B, 3C, 3D:
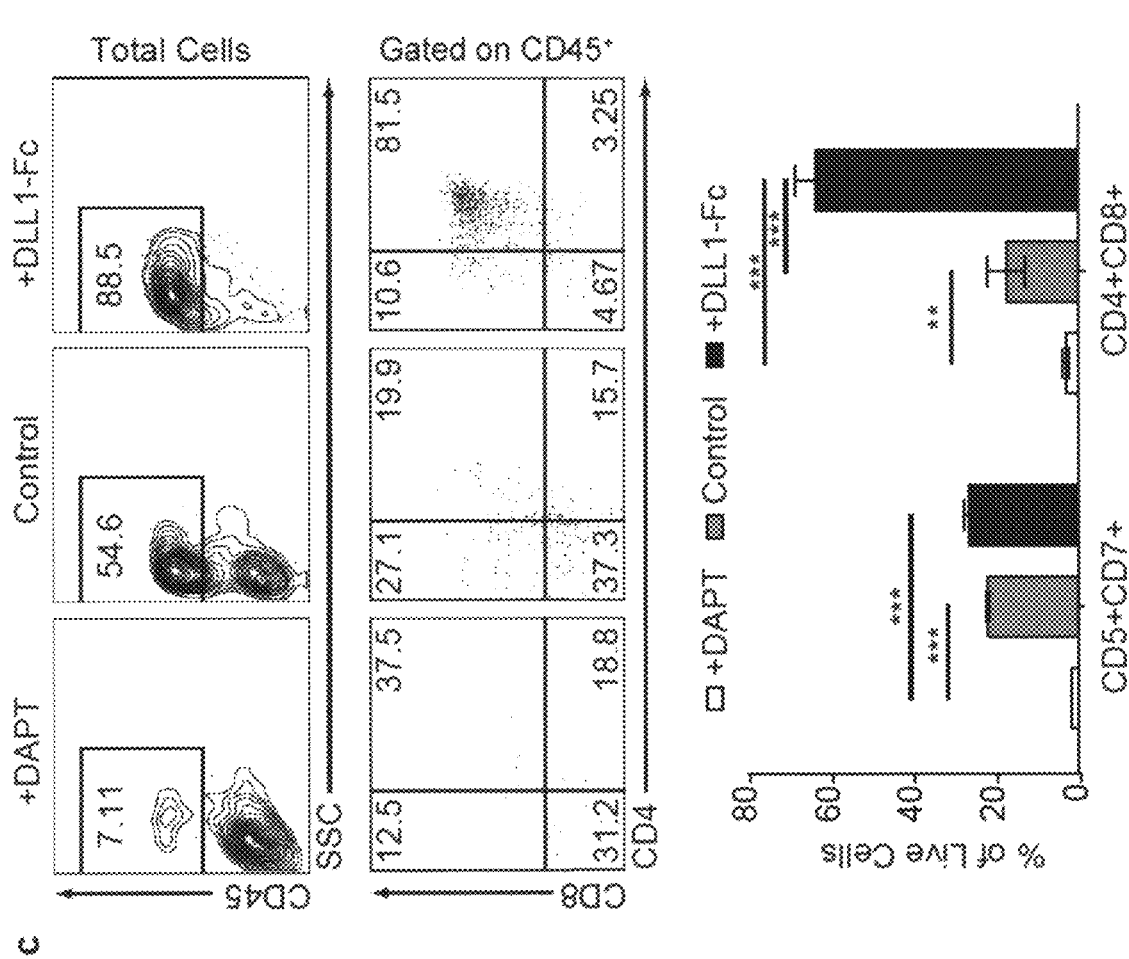

NOTCH Activation Maintains Multilineage Potential and Increases Definitive Characteristics of Hematopoietic Progenitors Emerging from HE Next, the inventors determined whether NOTCH has an effect on HPs emerging through the EHT. While NOTCH1 expression decreases among the CD144$^+$ endothelial population from D4+1 to D4+4, CD144$^-$CD43$^+$ blood cells increase and maintain expression of NOTCH1 post-transition from D4+2 to D4+4, notably among the CD34$^+$ subpopulation (FIG. 10A, B), thereby indicating that emerging blood cells are equipped to respond to NOTCH signaling. To determine how NOTCH affects post-EHT hematopoietic differentiation, cells collected from D4+4 HE cultures from the 3 different NOTCH conditions (DAPT, DMSO or DLL1-Fc) were plated in methocellulose to measure their colony forming potential. The total number of colonies was significantly lower in the DAPT treated NOTCH inhibition condition, while there was no significant change in the total number of colonies between the control condition and the NOTCH activation condition. Critically, however, there was a significant increase in multipotent GEMM-CFCs and GM-CFCs, as well as in E-CFCs among the hematopoietic progenitor cells from the HE cultured in NOTCH activation condition compared to control (FIG. 3A). These results suggest that NOTCH activation maintains multilineage potential of emerging HPs.

Next, whether increased NOTCH activation increases definitive-type hematopoiesis was determined. Previously, the Runx1+23 enhancer was found to be active in all hematopoietic progenitors, including yolk sac. HE found in regions where definitive hematopoiesis emerges have also been found to activate Runx1+23, including the para-aortic splanchnopleura, AGM region, vitelline and umbilical arteries[32-34, 39, 40]. The inventors generated a hESC reporter line with Runx1+23 enhancer driving eGFP expression knocked into the AAVS1 locus (FIG. 11A, B). We differentiated the Runx1+23 cell line, purified the D4 HE cells, and plated them in each of the 3 NOTCH conditions. There was significantly higher eGFP expression from D4+1 to D4+4 that emerge from the CD144$^+$ population in the NOTCH activation condition compared to the control. In contrast, cells treated with DAPT (NOTCH inhibition) had less eGFP expression compared to the control (FIG. 3B).

T cell potential is another hallmark of definitive hematopoiesis (Kennedy et al., 2012a). Comparative analysis of T-cell potential of the D4+4 CD43$^+$ cells from DAPT, DLL1-Fc and control conditions revealed that HPs from the NOTCH inhibition condition had no T-cell potential while HPs from the NOTCH activation condition had significantly increased T-cell potential (FIG. 3C). There was at least a four-fold increase in T-cell potential in the NOTCH activation conditions as compared to control (no NOTCH inhibition or activation).

In a separate assay, the inventors collected floating HPs on D4+4 and continued culture in a modified erythrocyte expansion condition (Dias et al., 2011). After 10 days, the inventors collected the cells and isolated mRNA to analyze their globin expression. The inventors found that erythrocytes generated from HPs from the NOTCH activation condition have significantly increased ratios of adult-type β-globin expression to embryonic ε-globin and fetal γ-globin expression, and the ratio of adult-type α-globin expression to embryonic ζ-globin expression, when compared to the erythrocytes generated from HPs from both the NOTCH inhibition condition and the control condition (FIG. 3D). Overall, these findings suggest that NOTCH signaling is required for definitive hematopoietic stem/progenitor cell specification.

NOTCH Activation of Day 4 HE Increases a Transient Population of DLL4$^+$ HE Cells with Arterial Identity Previously, the inventors identified CD73 expression to demark the loss of hemogenic potential within the D5 CD144$^+$ endothelial population[26]. As demonstrated above, D4 HE cells lacked the expression of the arterial marker, DLL4. However, when the inventors analyze CD73 and DLL4 expression within the D4+1 and D4+2 CD144$^+$ populations in each of the three NOTCH conditions, a significant increase in a unique transient population of CD73$^-$DLL4$^+$ endothelial cells in the NOTCH activation condition was found, and a delayed upregulation of CD73 expression on DLL4$^+$ endothelial cells was found, compared to the NOTCH inhibition and control conditions (FIG. 4A, B). In addition, when the inventors analyzed the CD144$^+$ population of the Runx1+23 cell line on D4+1, all eGFP$^+$ cells were found within the CD144$^+$CD73$^-$DLL4$^+$ population (FIG. 4C and FIG. 11C). Since DLL4 is expressed by HE underlying intraaortic hematopoietic clusters in the AGM[43], these results suggest that the DLL4$^+$ population may resemble arterial-type definitive HE found in arterial vasculature.

To corroborate this hypothesis, the inventors evaluated the expression of arterial, venous and definitive hematopoietic markers by real-time qPCR analysis of sorted D4 CD144$^+$CD43$^-$CD73$^-$ HE that are DLL4$^-$ by default (D4 HE) and D5 CD144$^+$ endothelial subpopulations CD144$^+$CD43$^-$CD73$^-$DLL4$^+$ (D5 HE:DLL4$^+$), CD144$^+$CD43$^-$CD73$^-$DLL4$^-$ (D5 HEDLL4$^-$), and CD144$^+$CD43$^-$CD73$^+$DLL4$^-$ (D5 nonHE:DLL4$^-$), (FIG. 4D). This analysis reveals that the D5 HE:DLL4$^+$ and nonHE:DLL4$^+$ populations have increased expression of NOTCH1, DLL4, EFNB2, HEY2, SOX17, and CXCR4 genes associated with arterial endothelium, and decreased expression of NR2F2 associated with venous endothelium, when compared to D5 DLL4$^-$ HE and nonHE populations. In contrast, D5 HE:DLL4$^-$ demonstrated an increased expression of NR2F2 venous marker. Interestingly, genes associated with definitive hematopoiesis, MYB and GATA2, were expressed significantly higher in the D5 HE:DLL4$^+$ population compared to the D5 HE:DLL4$^-$ population and D5 nonHE:DLL4$^+$ populations (FIG. 4E). We also revealed that emerging D4 HE cells that are lacking DLL4 expression were different from D5 HE:DLL4$^-$ and D5 HE:DLL4$^+$ cells. D4 HE did not express significant levels of arterial and venous markers, but retained expression of HAND1, which is expressed in extraembryonic and lateral plate mesoderm[44], suggesting that D4 HE may represent immature HE cells.

Figures 5A, 5B, 5C, 5D, 5E, 5F, 5G:
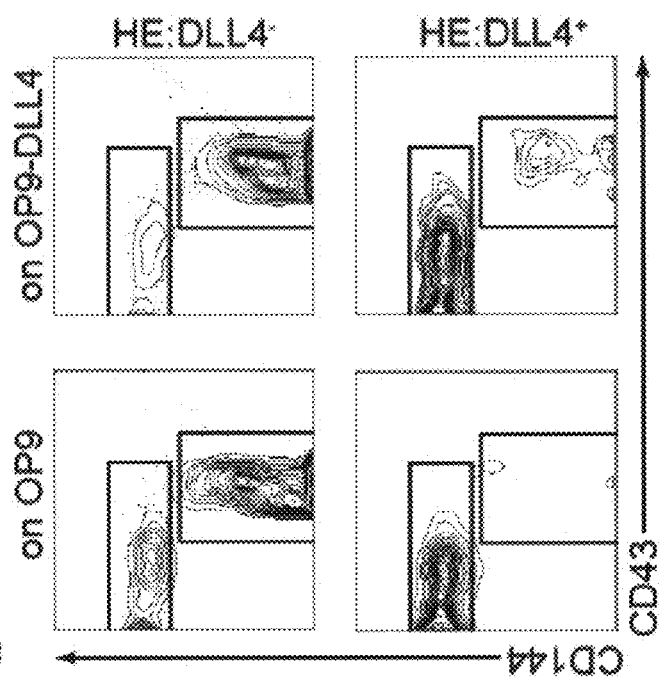
Figures 5A, 5B, 5C, 5D, 5E, 5F, 5G:
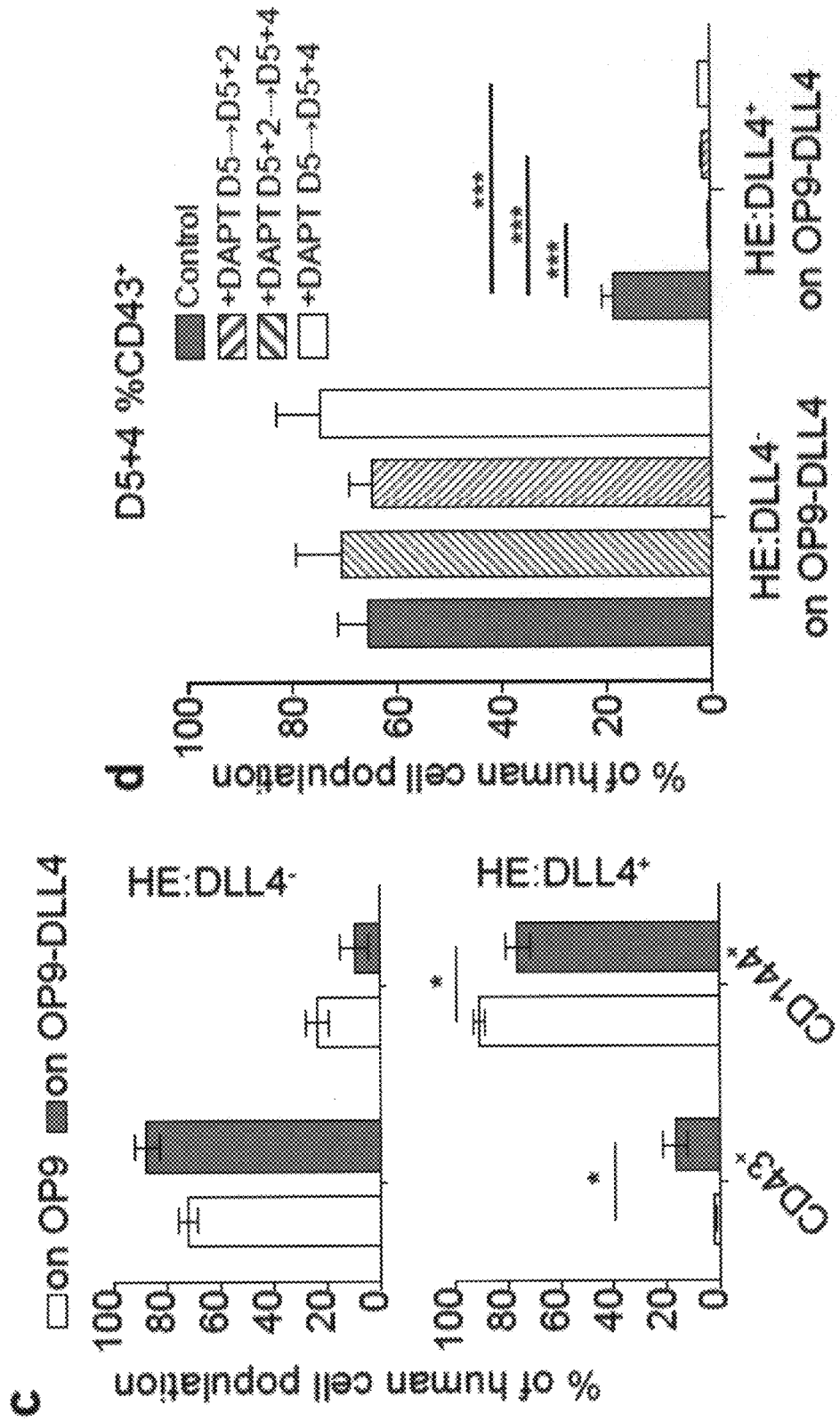
Figures 5A, 5B, 5C, 5D, 5E, 5F, 5G:
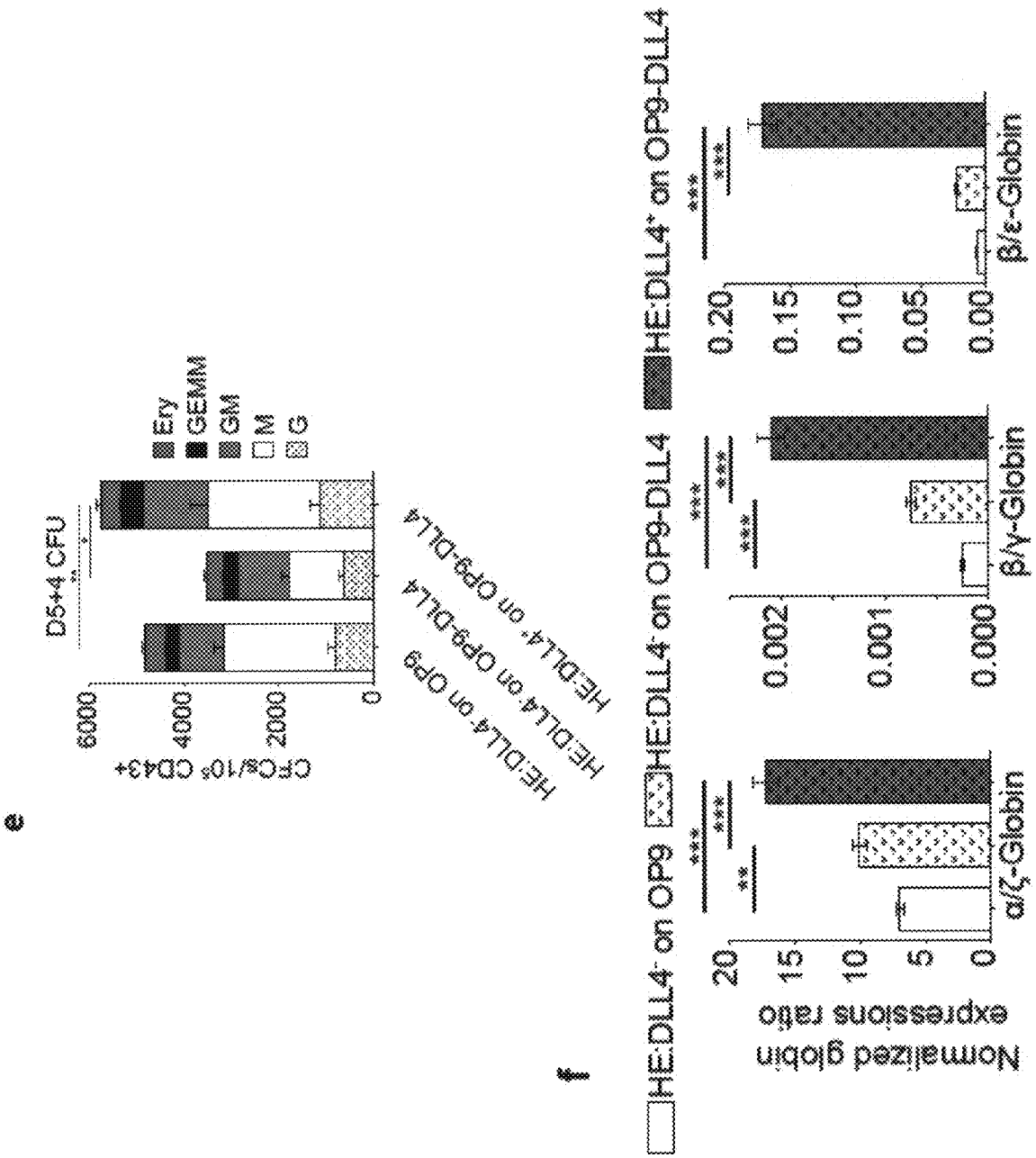
Figures 5A, 5B, 5C, 5D, 5E, 5F, 5G:
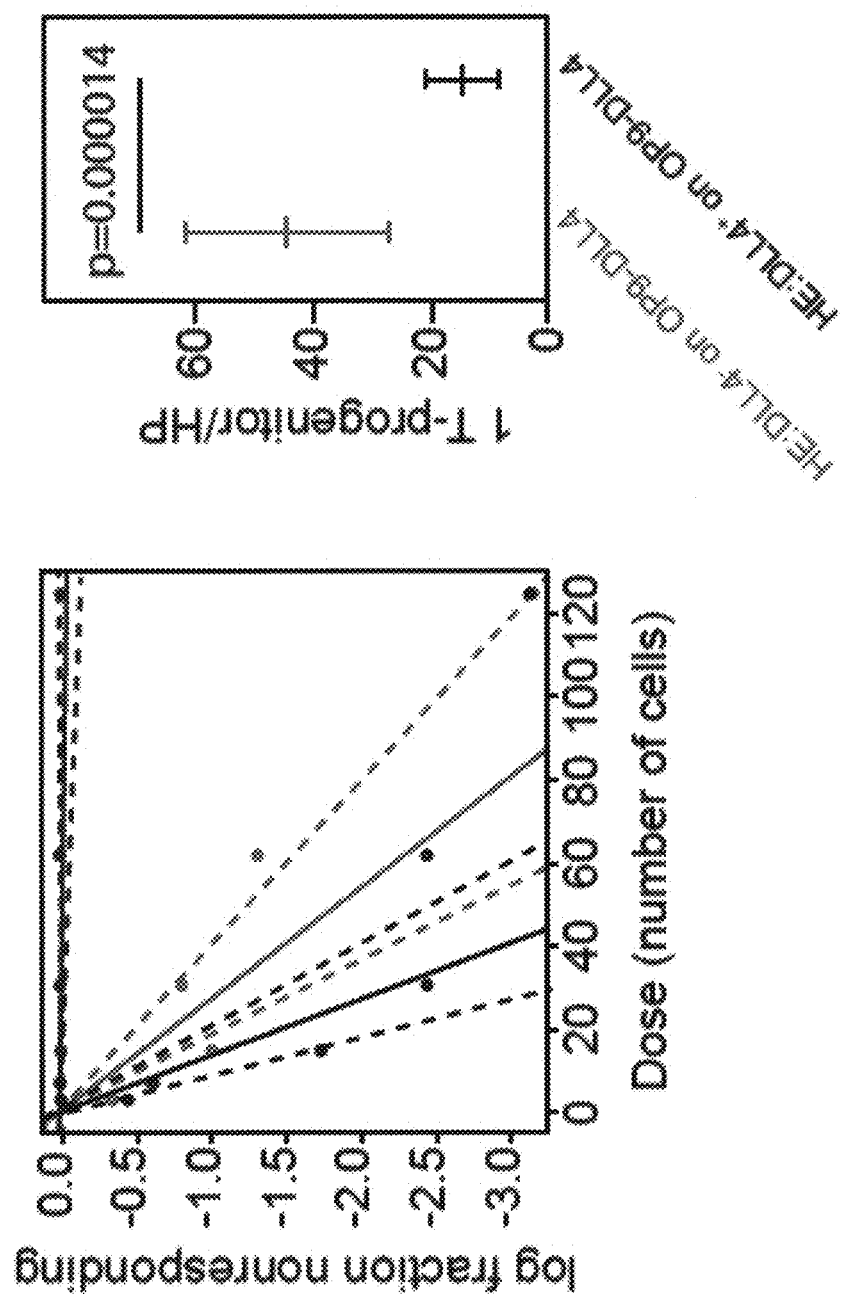

Definitive-Type Hematopoietic Progenitors Emerge from Arterial-Type Hemogenic Endothelium Upon NOTCH Activation To determine the hematopoietic potential of endothelium with arterial identity, the inventors continued differentiation of hPSCs to D5 and then sorted the D5 CD144$^+$CD43$^-$CD73$^-$ DLL4$^-$ (HE:DLL4$^-$) and D5 CD144$^+$CD43$^-$CD73$^-$DLL4$^+$ (HE:DLL4$^+$) endothelial subpopulations (FIG. 5A). While the inventors did not detect any CD43$^+$ blood cells from D5 HE:DLL4$^+$ on D5+4 in serum- and feeder-free conditions with or without DLL1-Fc (data not shown), these cells did produce blood when plated on OP9-DLL4 (FIG. 5B). In contrast, D5 HE:DLL4$^-$ cells undergo EHT and develop HPs on D5+4 on both OP9 and OP9-DLL4. However, unlike previously, when the inventors used D4 HE cells before they bifurcate into D5 HE:DLL4$^+$ and D5 HE:DLL4$^-$, there was no significant difference in blood production between the D5 HE:DLL4⁻ cells plated on OP9 versus OP9-DLL4 (FIG. 5B, C). The results were consistent across different iPSC lines as well (FIG. 12). In addition, DAPT treatment from D5 to D5+2, D5+2 to D5+4, and from D5 to D5+4 significantly inhibited hematopoietic activity of the HE:DLL4⁺ population, while DAPT treatment of HE:DLL4⁻ cultures had no effect on hematopoietic activity (FIG. 5D), suggesting that hematopoiesis from D5 HE:DLL4⁺, in contrast to D5 HE:DLL4⁻, is NOTCH-dependent.

Next, the inventors determined whether the HPs from each of the D5 HE subsets have differential definitive hematopoietic potential. When the HPs from the D5 HE subpopulations were plated in colony forming medium, the HPs which emerged from the HE:DLL4⁺ subpopulation cultured on OP9-DLL4 had increased colony forming cells, particularly of GEMM-CFCs compared to the HPs from D5 HE:DLL4⁻ on OP9 and OP9-DLL4 (FIG. 5E).

When we collected the floating HPs derived from D5 HE:DLL4⁻ on OP9 and OP9-DLL4, and HPs derived from D5 HE:DLL4⁺ on OP9-DLL4, and continued to grow them in the aforementioned erythrocyte expansion and maturation culture[42], the inventors found that erythrocytes generated from HPs derived from the D5 HE:DLL4⁺ on OP9-DLL4 have significantly increased ratios of β-globin expression to ε-globin and γ-globin expression, and an increased ratio of α-globin expression to ζ-globin expression, when compared to the erythrocytes generated from HPs derived from D5 HE:DLL4– on OP9 and OP9-DLL4 (FIG. 5F).

A limiting dilution assay (LDA) for lymphoid potential was also performed and we found that 1 in 14 HPs derived from D5 HE:DLL4⁺ on OP9-DLL4 have T-cell potential, while 1 in 44 HPs derived from D5 HE:DLL4⁻ on OP9-DLL4 have lymphoid potential. HPs derived from D5 HE:DLL4⁻ on OP9 and D5 HE:DLL4⁻ on OP9 with DAPT had only 1 in 10,706 and 1 in 10,895 cells had T-cell potential, respectively (FIG. 5G), thereby suggesting that D5 HE:DLL4⁺ phenotype enriches for HE that can produce HPs with T lymphoid potential.

In order to determine whether there are any molecular differences between HPs derived from HE:DLL4⁺ and HE:DLL4⁻ cells, the inventors performed RNA-seq analysis of CD235a/CD41a⁻CD34⁺CD43⁺CD45⁺ cells generated from these two different hemogenic endothelial cells following tertiary culture on either OP9 or OP9-DLL4 (FIG. 6A). As a basis for the analysis, genes that were differentially expressed in a 3-way Bayesian model involving HPs from HE:DLL4⁻ on OP9 (condition 1), HE:DLL4⁻ on OP9-DLL4 (condition 2) and HE:DLL4⁺ on OP9-DLL4 (condition 3) were used with focus specifically on genes upregulated in HE:DLL4⁺ vs. HE:DLL4⁻-derived HPs obtained from OP9-DLL4 cocultures. Among 131 differentially expressed genes in this category (Supplementary dataset 1, not shown), we identified two cell surface markers of HSCs in AGM: ACE and TEK[45, 46], and the following nine transcription factors: MECOM, GFIIB and ERG, essential for AGM and fetal liver hematopoiesis[47-50]; ARID5B, BCOR, and KDM6B, control lymphoid development[51-53]; ZNF93, highly expressed in T cells[54]; and RUNX1T1 and HOXB8, regulate expansion of blood progenitors[55, 56] (FIG. 6B). Using the known transcription-target relationships obtained by combining largely complementary data from HTRIdb[57] and CellNet[58], 163 regulatory interactions involving 110 transcription factors upstream of the nine differentially expressed transcription factor-encoding genes were pulled to construct a regulatory network in HPs derived from HE:DLL4⁺ cells on OP9-DLL4 (FIG. 6C). The database-derived structure of the network has been confirmed by our RNA-Seq data: transcription factors that are active according to our regulon analysis (red nodes) are apparently responsible for the upregulation of mRNA level of the target genes (large nodes). For three out of nine target genes (MECOM, RUNX1T1, GFI1B) we also have evidence of their protein-level activity (reddish color on the graph) detected as enrichment of their known targets among the differentially expressed genes. Interestingly, GATA2, SOX17, SOX18, MYB, PBX1, PRDM14, DACH1, KLF4, HOXA5, HOXA7 and NOTCH1 were identified as upstream regulators of these genes, thereby suggesting that the molecular program in HPs derived from the arterial-type HE:DLL4⁺ is driven by transcriptional regulators implicated in definitive hematopoiesis.

RNAseq analysis of NOTCH ligands, receptors and their downstream targets in D5 DLL4⁺ and DLL4⁻ HE, and HPs obtained from these populations, revealed D5 DLL4⁺ AHE express greater levels of NOTCH1, NOTCH4, DLL4, and JAG2 as compared to DLL4⁻ HE. However, expression of NOTCH associated molecules and SOX17 was substantially lower in HPs, including HPs generated from DLL4⁺ AHE on OP9-DLL4, suggesting a downregulation of NOTCH signaling and arterial program following EHT (FIG. 13). These findings are consistent with observations in the mouse system which demonstrated that downregulation of NOTCH1 and SOX17 is essential for EHT[59]. The exact mechanism of NOTCH downregulation at EHT stage remains unknown. Although NOTCH receptors are activated by cell surface ligands in neighboring cells (trans-activation of NOTCH), NOTCH ligands expressed by the same cell typically inactivate NOTCH signaling (cis-inhibition of NOTCH)[60]. While the response to trans-Delta is graded, cis-Delta response is abrupt and occurs at fixed threshold[61]. Thus, it is likely that in response to trans-DLL4 signaling from OP9-DLL4, AHE upregulates DLL4 expression to the threshold level required for cis-inhibition of NOTCH signaling in its own NOTCH1-expressing AHE cells allowing for EHT to proceed. This interpretation is consistent with studies in mouse system which demonstrated that expression of NOTCH ligands, including DLL1 and DLL4 in the AGM vascular niche and co-expression of DLL4 and NOTCH1 on emerging hematopoietic cells is critical for HE to undergo EHT and subsequent HSC amplification through limiting NOTCH1 receptor activation by cis-inhibition[36, 62]. Interestingly, despite downregulation of SOX17 and NOTCH1 expression following transition from DLL4⁺ HE, the inventors observed an enrichment of known targets (regulon members) of these genes in lin⁻CD34⁺CD45⁺ progenitors at post-EHT stage in OP9-DLL4 cultures (FIG. 7C). These finding suggest that following EHT, the expression of arterial genes decreases, but downstream program activated by these genes in the presence of NOTCH ligands remains active.

Together, these results imply that arterial-type CD144⁺CD43⁻CD73⁻DLL4⁺ HE represents the precursor of definitive NOTCH-dependent hematopoiesis with broad lympho-myeloid and definitive erythroid potential, while the CD144⁺CD43⁻CD73⁻DLL4⁻ phenotype is associated with emerging immature HE endothelium (D4) or HE that has primitive NOTCH-independent hematopoietic potential (D5).

DISCUSSION

In the current Example, the inventors revealed that NOTCH signaling is essential for specification of definitive lympho-myeloid hematopoiesis by eliciting arterial specification of HE from hPSCs. The inventors demonstrated that NOTCH activation promotes formation of transient CD144$^+$CD43$^-$CD73$^-$DLL4$^+$ HE population with high expression of arterial genes and active Runx1+23 enhancer that mark arterial type HE in AGM, umbilical and vitelline arteries[32, 33, 39, 40, 43]. Although CD144$^+$CD43$^-$CD73$^-$DLL4$^+$ AHE have lower hemogenic capacity compared to DLL4$^-$ HE, the hematopoietic potential of AHE is strictly NOTCH dependent. AHE is specified from CD144$^+$CD43$^-$CD73$^-$DLL4$^-$ immature HE cells emerging on D4 of differentiation in a NOTCH-dependent manner following acquisition of an arterial CD144$^+$CD43$^-$CD73$^-$DLL4$^+$ phenotype, while CD144$^+$CD43$^-$CD73$^-$DLL4$^-$ HE cells that failed to undergo arterial specification on day 5 of differentiation retained mostly primitive hematopoietic potential and were minimally affected by NOTCH activation (FIG. 6D). Demonstrating that definitive hematopoietic potential is highly enriched in arterial type HE is in concordance with in vivo studies that established the restriction of lymphoid cell and HSC formation to the arterial vasculature in the yolk sac and embryo proper[16, 17, 63-65] and enrichment of HSC precursors in DLL4$^+$ HE in AGM region[62]. Interestingly, DLL4$^+$ HE produced blood cells only on OP9-DLL4, but failed to undergo EHT in DLL1-Fc cultures in defined serum- and stroma-free conditions, thereby indicating that AHE in contrast to non-AHE, requires some additional signaling factor, either soluble factors in serum, matrix proteins or a paracrine signaling between the OP9-DLL4 and AHE, that are necessary for EHT.

In the present study, we provided evidence that NOTCH has several effects on hematopoiesis from HE. First, the inventors demonstrated that NOTCH signaling is important for the specification of arterial-type HE cells with definitive hematopoietic program. In addition, NOTCH activation also potentiates the EHT from these cells, while having little effect on expansion and survival of blood cells at post-EHT stage.

Overall, this Example indicate that regulation of NOTCH signaling would be important to mimic the arterial HE, definitive lympho-myeloid hematopoiesis and HSC specification in hPSC culture.

Materials and Methods

Human Pluripotent Stem Cell Maintenance and Differentiation

Human pluripotent stem cells, H1 hESC line, DF19-9-7T fibroblast-hiPSC line, IISH2i-BM9 bone marrow-iPSC line, and IISH3i-CB6 cord blood-iPSC line, were maintained and passaged in chemically defined conditions using vitronectin and E8 medium, as previously described[85]. The human PSCs were differentiated into hematoendothelial lineages using a modified protocol previously described[35]. On Day −1, hPSCs were singularized and plated on collagen IV-coated plates (0.5 µg/cm$^2$) at a cell density of 7,500 cells/cm$^2$ in E8 medium supplemented with 10 uM Rock inhibitor (Y-27632, Cayman Chemicals). On Day 0, the medium was changed to IF9S medium supplemented with BMP4, FGF2 (50 ng/ml), Activin A (15 ng/ml, Peprotech), LiCl (2 mM, Sigma), and ROCK inhibitor (0.5 µM, Cayman Chemicals) and cultured in hypoxia (5% O$_2$, 5% CO$_2$). On day 2, the medium was changed to IF9S medium supplemented with FGF2, VEGF (50 ng/ml, Peprotech), and 2.5 µM TGFβ inhibitor (SB-431542, Cayman Chemicals). On day 4, cell cultures were singularized and stained with anti-CD31 microbeads (Miltenyi) for 15 minutes. Cells were washed and HE were purified using CD31 antibody and MACS LS columns (Miltenyi). Purified CD31$^+$ HE were then plated at a density of 20,000 to 30,000 cells/cm$^2$ on collagen IV-coated plates (1 µg/cm$^2$) that were either co-coated with IgG-Fc fragments or human DLL1-Fc (made in-house), in IF9S medium supplemented with FGF2, VEGF, EGF, IGF-I, IGF-II, TPO, IL-6 (50 ng/ml), SCF (20 ng/ml), IL-3, FLT3L (10 ng/ml, Peprotech), and ROCK inhibitor (5 µM, Cayman Chemicals), and where specified, DMSO (1:1000, Fisher Scientific) or DAPT (10 µM, Cayman Chemicals), and cultured in normoxia (20% O$_2$, 5% CO$_2$). In some experiments, HE was cultured on plates co-coated with human JAG1-Fc (R&D Systems). A sample of the purified cells was analyzed by flow cytometry, and experiments were continued only if the purity of the HE was over 95% CD144$^+$. On Day 4+1, the medium was replaced with fresh medium containing the same supplements without ROCK inhibitor. On day 4+3, extra medium with the same supplements was added to the culture.

OP9 Maintenance and Co-Culture

OP9, OP9-DLL4, and the inducible OP9-iDLL4 (made in-house) cell lines were maintained in αMEM with 20% FBS (GE) on gelatin-coated plates in normoxia as previously described[86]. Using TrypLE (Thermo), OP9 were passaged at a 1:8 ratio every 3-4 days when they were 80% confluent. One day before co-culture with differentiated human HE cells, OP9 lines were treated with mitomycin C (1 mg/ml) for 2 hours and then plated at a density of 12,500 cells/cm$^2$ as previously described[87]. D4 HE cells or D5 CD144$^+$ subsets were plated onto OP9 lines at a density between 1000 to 2000 cells/cm$^2$ in medium containing αMEM with 10% FBS (GE), TPO, SCF, IL-6 (50 ng/ml), IL-3, and FLT3L (10 ng/ml). Medium was changed after 24 hours, and extra medium added 2 days later. Experiments conducted with DAPT were treated with 20 µM, while corresponding control conditions had DMSO added at a 1:500 dilution.

Generation of OP9-DLL4, OP9-JAG1 and DOX-Inducible OP9-iDLL4

Human DLL4 gene fragment was amplified by PCR from a vector previously used to establish the OP9-DLL4 cell line, and the JAG1 gene was amplified by PCR from cDNA of D5 differentiation cultures that were treated with Sonic Hedgehog from D2-5, which has been found to increase Jag1 expression (data not shown). The DLL4 and JAG1 gene fragments were subsequently cloned into a pSIN-EF1a-DLL4-IRES-Puro and pSIN-EF1a-JAG1-IRES-Puro lentiviral expression vector for the constitutively expressed OP9-DLL4 and JAG1 lines, respectively. Virus production and concentration was carried out by calcium phosphate transfection of Lenti-X 293T cells (Clonetech, Mountain View, Calif.). After 12 hours, virus-containing medium was replaced with fresh OP9 culture medium. After 3 days, cells were treated with Puromycin for 2 weeks. For dox-inducible OP9-DLL4, the DLL4 gene fragment was subsequently cloned into a pPB-TRE-DLL4-P2A-Venus-EF1α-Zeo‖EF1a-M2rtTA-T2A-Puro PiggyBac vector made in house. OP9 cells were then transfected with pPB vector. 3 days later the transfected OP9 cells were treated with Puromycin/Zeocin for 2 weeks. Samples of the OP9-iDLL4 cells were treated with doxycycline for 24 hours, then DLL4 and Venus expression were confirmed by flow cytometry.

Single-Cell Deposition Assay for Endothelial-to-Hematopoietic Transition\

One day before single-cell deposition, the OP9-iDLL4 cell line was treated with mitomycin C as described above, and passaged into 96-well plates at a density of 12,500 cells/cm2. OP9-iDLL4 used for the NOTCH activation condition was incubated with doxycycline for 24 hours after passaging into 96-well plates. On the day of single-cell sorting, OP9-iDLL4 medium was changed to αMEM with 10% FBS (GE), TPO, SCF, IL-6 (50 ng/ml), IL-3, FLT3L (10 ng/ml), and DMSO (1:500) for the control, and NOTCH activation conditions, or DAPT (20 μM) for the NOTCH inhibition condition. Day 4 differentiated human pluripotent stem cells were singularized, stained for CD309-PE and CD144-APC (Miltenyi Biotech), and single-cell sorted into individual wells of the 96-well plates using a FACS Aria II. To exclude possibility of doublets, we used a low density (less than 1 million cells/ml) cells suspension, sorting speed less than 1000 cellular events/per second and stringent gating on single cells using both FSC-A vs FSC-H and SSC-A vs SSC-H. One day after sorting, the medium was changed to fresh medium without DMSO or DAPT, and extra medium was added every 3 days. Seven days later, the plates were fixed and stained for immunofluorescent staining with anti-CD144 (rabbit, eBioscience) and anti-CD43 (mouse, BD Biosciences) primary antibodies and anti-rabbit AlexaFluor488 and anti-mouse AlexaFluor594 secondary antibodies (Jackson Immunology) in order to score the hematopoietic/endothelial colonies.

CellTracer Proliferation Assay and Cell Cycle Analysis

D4 $CD31^+$ HE cells were incubated in PBS with Cell-Tracer (1 μg/ml, Thermo) for 20 minutes at 37° C. After washing, the cells were plated on collagen IV-coated plates with either Fc-IgG or DLL1-Fc and the modified Day 4 medium, as described above, at a higher density of 30,000 to 40,000 $cells/cm^2$ due to toxicity from the CellTracer. Aliquots of the purified cells were analyzed by flow cytometry to determine the purity of the MACS cells and establish the Generation 0 peak for the proliferation assay. Secondary cultures were collected every day after plating for flow cytometry analysis, and calibration beads were used to generate compatible CellTracer results. After D4+4, FlowJo™ Analysis software was used to concatenate the data from each day. The average number of cell divisions was calculated based on the number of cells on each day (FIG. 1F) and applied to the proliferation platform algorithm in FlowJo™ to determine the specific generation gates. Those peaks were re-applied to individual sets of data to determine the percentage of each generation within the hematoendothelial populations. For cell cycle analysis, D4+4 cells were incubated in culture medium with EdU (10 μM, Thermo Fisher) for 2 hours and stained with CD43 and CD144 antibodies for 20 min. For EdU detection, the Click-IT EdU Alexa Fluor 647 kit (Thermo Fisher) with DAPI (4 μg/ml, Sigma) was used as described by the manufacturer.

T-Cell Differentiation and T-Cell Limiting Dilution Assay

Total D4+4 cultures were singularized, strained, and cultured in T-cell differentiation conditions on OP9-DLL4 for 3 weeks as described[35]. For D5+4 cultures, only the floating hematopoietic cells were collected and cultured in T-cell differentiation conditions. Limiting Dilution Assays were conducted with the floating cells collected from D5+4 cultures (HE:DLL4$^-$ on OP9+DAPT, OP9+DMSO, and OP9-DLL4, and HE:DLL4$^+$ on OP9-DLL4). Row A of a 96-well plate received 500 cells/well, and each subsequent row afterwards had half the previous row (Row B contained 250, Row C contained 125 . . . Row H contained 3-4 cells). The wells were scored 2 weeks later by eye and flow-cytometry for $CD5^+CD7^+$ containing cells. Positive threshold was set at 167 $CD5^+CD7^+$ cells/well. Extreme limiting dilution analysis was conducted using the previously established algorithm[88]

Red Blood Cell Differentiation and Maturation of D4+4 Cultures

In order to assess the definitive erythropoietic potential of hematopoietic progenitor cells, we adopted our previously describe red blood cell differentiation protocol[42] to become chemically defined and feeder- and serum-free. Floating cells were collected, washed, and plated back into their respective cultures for D4+5 cells, or plated onto collagen IV-coated plates for D5+4 cells, with IF9S supplemented with dexamethasone (10 μM), EPO (2 U/ml), SCF, FLT3L, TPO, IL-6 (100 ng/ml), and IL-3 (10 ng/ml). Extra medium with the same supplements was added 2 days later. An additional 2 days later, the cultures were treated with half-medium changes every 2 days with IF9S supplemented with dexamethasone (10 μM), SCF (100 ng/ml), and EPO (2 U/ml). The floating cells were collected 10 days later to analyze by flow cytometry and RNA isolated for qPCR analysis.

Generating Runx1+23 Enhancer Reporter Cell Line

Runx1+23 enhancer fragment[33] was amplified by PCR and subsequently cloned into the AAVS-SA-2A-PURO vector (gift from Gadue Lab, The Children's Hospital of Philadelphia). Human ESCs were transfected with zinc-finger nuclease vectors and later puromycin-resistant individual cells were clonally expanded and on-targeted clones were selected, as previously described[38]. Southern Blot (SB) analysis was performed by DIG-labeling hybridization (Roche). Briefly, 10 μg genomic DNA was digested using a EcoRV restriction enzyme for overnight, separated on a 0.7% agarose gel for 6 hours, transferred to a nylon membrane (Amersham), and incubated with DIG-labeling probes. The external probe is a DIG-labeled 600 nucleotide fragment that binds to the EcoRV-digested fragment of the 5' external region. The internal probe is a DIG-labeled 700 nucleotide fragment that binds to the EcoRV-digested fragment of the of the eGFP region.

Hematopoietic Colony Forming Unit Assay

Hematopoietic colony forming unit assay was conducted in serum-containing H4436 Methocult (Stem Cell Technologies) as previously described[26, 35].

Flow Cytometry and FACS-Sorting

Flow Cytometry was conducted using the MACSQuant 10 (Miltenyi Biotech). FACS-sorting was conducted on a FACS Aria II (BD) as previously described[26, 35, 86].

Western Blot

Cell extracts were prepared by adding IP Lysis buffer (Thermo Scientific) with protease inhibitor cocktail (Sigma). Cell lysates (10 μg) were separated by 6% SDS-PAGE. Separated proteins were transferred to a PVDF membrane, and were stained with Notch1 and Notch1-ICD antibody (Cell Signaling Technology) and GAPDH (Santa Cruz). Immunoblots were visualized using the ECL PLUS detection kit (Amersham Pharmacia).

qPCR Analysis

Cells were differentiated for the respective days and sorted on a FACS Aria II. RNA was collected using RNA MiniPrep Plus (Invitrogen) and quantified on a NanoDrop (GE Healthcare). Equal amounts of RNA were used for cDNA synthesis using SuperScript III First-Strand Synthesis System (Life Technologies). qPCR was conducted using Platinum SYBR Green qPCR SuperMix (Life Technologies). The reactions were run on a Mastercycler RealPlex Thermal Cycler (Eppendorf) and the expression levels were calculated by minimal cycle threshold values (Ct) normalized to the reference expression of RPL13a. The qPCR products were run on an agarose gel and stained with ethidium bromide to confirm specificity of the primers. Primer sequences can be found in FIG. 16.

RNA-Seq Data Processing and Analysis

Total RNA was isolated from the D4 HE, D5 HE:DLL4$^+$ and HE:DLL4$^-$ and CD235a/CD41a$^-$CD34$^+$CD45$^+$ derived from HE:DLL4$^+$ and HEDLL4$^-$ cells using the RNeasy mini Plus Kit (Qiagen). RNA purity and integrity was evaluated by capillary electrophoresis on the Bioanalyzer 2100 (Agilent Technologies, Santa Clara, Calif.). One hundred nanograms of total RNA was used to prepare sequencing libraries using the TruSeq RNA Sample Preparation kit (Illumina, San Diego, Calif.). Final cDNA libraries were quantitated with the Qubit Fluorometer (Life Technologies, Carlsbad, Calif.) and multiplexed with eighteen total indexed libraries per lane. Sequencing was performed using the HiSeq 3000 (Illumina, San Diego, Calif.) with a single read of 64 bp and index read of 7 bp.

Base-calling and demultiplexing were completed with the Illumina Genome Analyzer Casava Software, version 1.8.2. Following quality assessment and filtering for adapter molecules and other sequencing artifacts, the remaining sequencing reads were aligned to transcript sequences corresponding to hg19 human genome annotation. Bowtie v 1.1.2 was used, allowing two mismatches in a 25 bp seed, and excluding reads with more than 200 alignments[89]. RSEM v 1.3.0 was used to estimate isoform or gene relative expression levels in units of "transcripts per million" (tpm), as well as posterior mean estimate of the "expected counts" (the non-normalized absolute number of reads assigned by RSEM to each isoform/gene)[90, 91]. R statistical environment (R core team, 2014) was used at all of the stages of downstream data analysis. The entire set of libraries was pre-normalized as a pool using median normalization routine from EBSeq package[92]. EBSeq with 10 iterations was applied to call for differential expression. The EBSeq's default procedure of filtering low-expressed genes was suppressed by setting the QtrmCut parameter to zero. Genes with assigned value of Posterior Probability of Differential Expression above 0.95 were preliminary selected. Subsequently, only genes demonstrating the Critical Coefficient[93] value above 1.5 were retained as differentially expressed.

Statistical Analysis

Statistical analysis was performed in PRISM software. Data obtained from multiple experiments were reported as mean+/−standard error. Where appropriate, either a 1-way ANOVA or 2-way ANOVA were utilized with a Bonferroni post-hoc test. Differences were considered significant when *p<0.05, p<0.01, or *p<0.001.

Additional Information

Accession codes: The RNAseq data has been deposited in Gene Expression Omnibus under accession number GSE95028 and GSE96815.

REFERENCES

1. Sugimura, R. et al. Haematopoietic stem and progenitor cells from human pluripotent stem cells. *Nature* 545, 432-438 (2017).
2. Rahman, N. et al. Engineering the haemogenic niche mitigates endogenous inhibitory signals and controls pluripotent stem cell-derived blood emergence. *Nat Commun* 8, 15380 (2017).
3. Ledran, M. H. et al. Efficient hematopoietic differentiation of human embryonic stem cells on stromal cells derived from hematopoietic niches. *Cell Stem Cell* 3, 85-98. (2008).
4. Wang, L. et al. Generation of hematopoietic repopulating cells from human embryonic stem cells independent of ectopic HOXB4 expression. *J Exp Med* 201, 1603-1614. Epub 2005 May 1609. (2005).
5. Dzierzak, E. & Speck, N. A. Of lineage and legacy: the development of mammalian hematopoietic stem cells. *Nat Immunol* 9, 129-136 (2008).
6. Bertrand, J. Y. et al. Haematopoietic stem cells derive directly from aortic endothelium during development. *Nature* 464, 108-111 (2010).
7. Medvinsky, A., Rybtsov, S. & Taoudi, S. Embryonic origin of the adult hematopoietic system: advances and questions. *Development* 138, 1017-1031 (2011).
8. Bigas, A., D'Altri, T. & Espinosa, L. The Notch pathway in hematopoietic stem cells. *Curr Top Microbiol Immunol* 360, 1-18 (2012).
9. Bigas, A. & Espinosa, L. Hematopoietic stem cells: to be or Notch to be. *Blood* 119, 3226-3235 (2012).
10. Kumano, K. et al. Notch1 but not Notch2 is essential for generating hematopoietic stem cells from endothelial cells. *Immunity* 18, 699-711 (2003).
11. Burns, C. E., Traver, D., Mayhall, E., Shepard, J. L. & Zon, L. I. Hematopoietic stem cell fate is established by the Notch-Runx pathway. *Genes Dev* 19, 2331-2342 (2005).
12. Robert-Moreno, A. et al. Impaired embryonic haematopoiesis yet normal arterial development in the absence of the Notch ligand Jagged1. *EMBO J* 27, 1886-1895 (2008).
13. Robert-Moreno, A., Espinosa, L., de la Pompa, J. L. & Bigas, A. RBPjkappa-dependent Notch function regulates Gata2 and is essential for the formation of intra-embryonic hematopoietic cells. *Development* 132, 1117-1126 (2005).
14. Duarte, A. et al. Dosage-sensitive requirement for mouse Dll4 in artery development. *Genes Dev* 18, 2474-2478 (2004).
15. Deng, Y. et al. Endothelial RAF1/ERK activation regulates arterial morphogenesis. *Blood* 121, 3988-3996, S3981-3989 (2013).
16. Yzaguirre, A. D. & Speck, N. A. Insights into blood cell formation from hemogenic endothelium in lesser-known anatomic sites. *Dev Dyn* (2016).
17. Gordon-Keylock, S., Sobiesiak, M., Rybtsov, S., Moore, K. & Medvinsky, A. Mouse extraembryonic arterial vessels harbor precursors capable of maturing into definitive HSCs. *Blood* 122, 2338-2345 (2013).
18. Bigas, A., Guiu, J. & Gama-Norton, L. Notch and Wnt signaling in the emergence of hematopoietic stem cells. *Blood Cells Mol Dis* 51, 264-270 (2013).
19. Nakagawa, M. et al. AML1/Runx1 rescues Notch1-null mutation-induced deficiency of para-aortic splanchnopleural hematopoiesis. *Blood* 108, 3329-3334 (2006).
20. Hadland, B. K. et al. A requirement for Notch1 distinguishes 2 phases of definitive hematopoiesis during development. *Blood* 104, 3097-3105 (2004).
21. Lawson, N. D., Vogel, A. M. & Weinstein, B. M. sonic hedgehog and vascular endothelial growth factor act upstream of the Notch pathway during arterial endothelial differentiation. *Dev Cell* 3, 127-136 (2002).
22. Lawson, N. D. et al. Notch signaling is required for arterial-venous differentiation during embryonic vascular development. *Development* 128, 3675-3683 (2001).
23. Gering, M. & Patient, R. Hedgehog signaling is required for adult blood stem cell formation in zebrafish embryos. *Dev Cell* 8, 389-400 (2005).

24. Kim, P. G. et al. Signaling axis involving Hedgehog, Notch, and Scl promotes the embryonic endothelial-to-hematopoietic transition. *Proc Natl Acad Sci USA* 110, E141-150 (2013).
25. Burns, C. E. et al. A genetic screen in zebrafish defines a hierarchical network of pathways required for hematopoietic stem cell emergence. *Blood* 113, 5776-5782 (2009).
26. Choi, K.-D. et al. Identification of the Hemogenic Endothelial Progenitor and Its Direct Precursor in Human Pluripotent Stem Cell Differentiation Cultures. *Cell Rep* 2, 553-567 (2012).
27. Ditadi, A. et al. Human definitive haemogenic endothelium and arterial vascular endothelium represent distinct lineages. *Nat Cell Biol* 17, 580-591 (2015).
28. Elcheva, I. et al. Direct induction of haematoendothelial programs in human pluripotent stem cells by transcriptional regulators. *Nat Commun* 5, 4372 (2014).
29. Slukvin, I I Generating human hematopoietic stem cells in vitro-exploring endothelial to hematopoietic transition as a portal for stemness acquisition. *FEBS Lett* (2016).
30. Guibentif, C. et al. Single-Cell Analysis Identifies Distinct Stages of Human Endothelial-to-Hematopoietic Transition. *Cell Rep* 19, 10-19 (2017).
31. Ayllon, V. et al. The Notch ligand DLL4 specifically marks human hematoendothelial progenitors and regulates their hematopoietic fate. *Leukemia* 29, 1741-1753 (2015).
32. Swiers, G. et al. Early dynamic fate changes in haemogenic endothelium characterized at the single-cell level. *Nat Commun* 4, 2924 (2013).
33. Tamplin, O. J. et al. Hematopoietic stem cell arrival triggers dynamic remodeling of the perivascular niche. *Cell* 160, 241-252 (2015).
34. Nottingham, W. T. et al. Runx1-mediated hematopoietic stem-cell emergence is controlled by a Gata/Ets/SCL-regulated enhancer. *Blood* 110, 4188-4197 (2007).
35. Uenishi, G. et al. Tenascin C promotes hematoendothelial development and T lymphoid commitment from human pluripotent stem cells in chemically defined conditions. *Stem cell reports* 3, 1073-1084 (2014).
36. Hadland, B. K. et al. Endothelium and NOTCH specify and amplify aorta-gonad-mesonephros-derived hematopoietic stem cells. *J Clin Invest* 125, 2032-2045 (2015).
37. Ohishi, K., Varnum-Finney, B. & Bernstein, I. D. Delta-1 enhances marrow and thymus repopulating ability of human CD34(+)CD38(-) cord blood cells. *J Clin Invest* 110, 1165-1174 (2002).
38. Jung, H. S. et al. A human VE-cadherin-tdTomato and CD43-green fluorescent protein dual reporter cell line for study endothelial to hematopoietic transition. *Stem Cell Res* 17, 401-405 (2016).
39. Ng, C. E. et al. A Runx1 intronic enhancer marks hemogenic endothelial cells and hematopoietic stem cells. *Stem Cells* 28, 1869-1881 (2010).
40. Bee, T. et al. The mouse Runx1+23 hematopoietic stem cell enhancer confers hematopoietic specificity to both Runx1 promoters. *Blood* 113, 5121-5124 (2009).
41. Kennedy, M. et al. T lymphocyte potential marks the emergence of definitive hematopoietic progenitors in human pluripotent stem cell differentiation cultures. *Cell Rep* 2, 1722-1735 (2012).
42. Dias, J. et al. Generation of red blood cells from human induced pluripotent stem cells. *Stem Cells Dev* 20, 1639-1647 (2011).
43. Richard, C. et al. Endothelio-mesenchymal interaction controls runx1 expression and modulates the notch pathway to initiate aortic hematopoiesis. *Dev Cell* 24, 600-611 (2013).
44. Barnes, R. M., Firulli, B. A., Conway, S. J., Vincentz, J. W. & Firulli, A. B. Analysis of the Hand1 cell lineage reveals novel contributions to cardiovascular, neural crest, extra-embryonic, and lateral mesoderm derivatives. *Dev Dyn* 239, 3086-3097 (2010).
45. Jokubaitis, V. J. et al. Angiotensin-converting enzyme (CD143) marks hematopoietic stem cells in human embryonic, fetal, and adult hematopoietic tissues. *Blood* 111, 4055-4063. Epub 2007 November 4059. (2008).
46. Hsu, H. C. et al. Hematopoietic stem cells express Tie-2 receptor in the murine fetal liver. *Blood* 96, 3757-3762 (2000).
47. Goyama, S. et al. Evi-1 is a critical regulator for hematopoietic stem cells and transformed leukemic cells. *Cell Stem Cell* 3, 207-220 (2008).
48. Sato, T. et al. Evi-1 promotes para-aortic splanchnopleural hematopoiesis through up-regulation of GATA-2 and repression of TGF-b signaling. *Cancer Sci* 99, 1407-1413 (2008).
49. Thambyrajah, R. et al. GFI1 proteins orchestrate the emergence of haematopoietic stem cells through recruitment of LSD1. *Nat Cell Biol* 18, 21-32 (2016).
50. Taoudi, S. et al. ERG dependence distinguishes developmental control of hematopoietic stem cell maintenance from hematopoietic specification. *Genes Dev* 25, 251-262 (2011).
51. Manna, S. et al. Histone H3 Lysine 27 demethylases Jmjd3 and Utx are required for T-cell differentiation. *Nat Commun* 6, 8152 (2015).
52. Lahoud, M. H. et al. Gene targeting of Desrt, a novel ARID class DNA-binding protein, causes growth retardation and abnormal development of reproductive organs. *Genome Res* 11, 1327-1334 (2001).
53. Beguelin, W. et al. EZH2 and BCL6 Cooperate to Assemble CBX8-BCOR Complex to Repress Bivalent Promoters, Mediate Germinal Center Formation and Lymphomagenesis. *Cancer Cell* 30, 197-213 (2016).
54. Bellefroid, E. J. et al. Clustered organization of homologous KRAB zinc-finger genes with enhanced expression in human T lymphoid cells. *EMBO J* 12, 1363-1374 (1993).
55. Basecke, J. et al. AML1/ETO promotes the maintenance of early hematopoietic progenitors in NOD/SCID mice but does not abrogate their lineage specific differentiation. *Leuk Lymphoma* 46, 265-272 (2005).
56. Redecke, V. et al. Hematopoietic progenitor cell lines with myeloid and lymphoid potential. *Nat Methods* 10, 795-803 (2013).
57. Bovolenta, L. A., Acencio, M. L. & Lemke, N. HTRIdb: an open-access database for experimentally verified human transcriptional regulation interactions. *BMC Genomics* 13, 405 (2012).
58. Cahan, P. et al. CellNet: network biology applied to stem cell engineering. *Cell* 158, 903-915 (2014).
59. Lizama, C. O. et al. Repression of arterial genes in hemogenic endothelium is sufficient for haematopoietic fate acquisition. *Nat Commun* 6, 7739 (2015).
60. del Alamo, D., Rouault, H. & Schweisguth, F. Mechanism and significance of cis-inhibition in Notch signalling. *Curr Biol* 21, R40-47 (2011).
61. Sprinzak, D. et al. Cis-interactions between Notch and Delta generate mutually exclusive signalling states. *Nature* 465, 86-90 (2010).

62. Hadland, B. K. et al. A Common Origin for B-1a and B-2 Lymphocytes in Clonal Pre-Hematopoietic Stem Cells. *Stem cell reports* 8, 1563-1572 (2017).
63. Rybtsov, S., Ivanovs, A., Zhao, S. & Medvinsky, A. Concealed expansion of immature precursors underpins acute burst of adult HSC activity in ketal liver. *Development* 143, 1284-1289 (2016).
64. de Bruijn, M. F., Speck, N. A., Peeters, M. C. & Dzierzak, E. Definitive hematopoietic stem cells first develop within the major arterial regions of the mouse embryo. *The EMBO journal* 19, 2465-2474 (2000).
65. North, T. et al. Cbfa2 is required for the formation of intra-aortic hematopoietic clusters. *Development* 126, 2563-2575 (1999).
66. Jang, I. H. et al. Notch1 acts via Foxc2 to promote definitive hematopoiesis via effects on hemogenic endothelium. *Blood* 125, 1418-1426 (2015).
67. Lee, J. B. et al. Notch-HES1 signaling axis controls hemato-endothelial fate decisions of human embryonic and induced pluripotent stem cells. *Blood* 122, 1162-1173 (2013).
68. Shojaei, F. et al. Hierarchical and ontogenic positions serve to define the molecular basis of human hematopoietic stem cell behavior. *Dev Cell* 8, 651-663. (2005).
69. Gerhardt, D. M. et al. The Notch1 transcriptional activation domain is required for development and reveals a novel role for Notch1 signaling in fetal hematopoietic stem cells. *Genes Dev* 28, 576-593 (2014).
70. Guiu, J. et al. Hes repressors are essential regulators of hematopoietic stem cell development downstream of Notch signaling. *J Exp Med* 210, 71-84 (2013).
71. Gama-Norton, L. et al. Notch signal strength controls cell fate in the haemogenic endothelium. *Nat Commun* 6, 8510 (2015).
72. Souilhol, C. et al. Inductive interactions mediated by interplay of asymmetric signalling underlie development of adult haematopoietic stem cells. *Nat Commun* 7, 10784 (2016).
73. Dou, D. R. et al. Medial HOXA genes demarcate haematopoietic stem cell fate during human development. *Nat Cell Biol* 18, 595-606 (2016).
74. Ng, E. S. et al. Differentiation of human embryonic stem cells to HOXA+hemogenic vasculature that resembles the aorta-gonad-mesonephros. *Nat Biotechnol* (2016).
75. Monteiro, R. et al. Transforming Growth Factor beta Drives Hemogenic Endothelium Programming and the Transition to Hematopoietic Stem Cells. *Dev Cell* (2016).
76. Chanda, B., Ditadi, A., Iscove, N. N. & Keller, G. Retinoic acid signaling is essential for embryonic hematopoietic stem cell development. *Cell* 155, 215-227 (2013).
77. Ghiaur, G. et al. Regulation of human hematopoietic stem cell self-renewal by the microenvironment's control of retinoic acid signaling. *Proc Natl Acad Sci USA* 110, 16121-16126 (2013).
78. He, Q. & Liu, F. Unexpected role of inflammatory signaling in hematopoietic stem cell development: its role beyond inflammation. *Curr Opin Hematol* 23, 18-22 (2016).
79. He, Q. et al. Inflammatory signaling regulates hematopoietic stem and progenitor cell emergence in vertebrates. *Blood* 125, 1098-1106 (2015).
80. Li, Y. et al. Inflammatory signaling regulates embryonic hematopoietic stem and progenitor cell production. *Genes Dev* 28, 2597-2612 (2014).
81. Heo, H. R. et al. Hormonal regulation of hematopoietic stem cells and their niche: a focus on estrogen. *IntJ Stem Cells* 8, 18-23 (2015).
82. Kim, H. R. et al. Improved hematopoietic differentiation of human pluripotent stem cells via estrogen receptor signaling pathway. *Cell Biosci* 6, 50 (2016).
83. Kim, P. G. et al. Flow-induced protein kinase A-CREB pathway acts via BMP signaling to promote HSC emergence. *J Exp Med* 212, 633-648 (2015).
84. North, T. E. et al. Hematopoietic stem cell development is dependent on blood flow. *Cell* 137, 736-748 (2009).
85. Chen, G. et al. Chemically defined conditions for human iPSC derivation and culture. *Nat Methods* 8, 424-429 (2011).
86. Vodyanik, M. A. & Slukvin, I. I. Hematoendothelial differentiation of human embryonic stem cells. *Current protocols in cell biology/editorial board, Juan S. Bonifacino . . . [et al.]* Chapter 23, Unit 23.26 (2007).
87. Zhang, W. J., Park, C., Arentson, E. & Choi, K. Modulation of hematopoietic and endothelial cell differentiation from mouse embryonic stem cells by different culture conditions. *Blood* 105, 111-114. Epub 24 Jul. 2001. (2005).
88. Hu, Y. & Smyth, G. K. ELDA: extreme limiting dilution analysis for comparing depleted and enriched populations in stem cell and other assays. *J Immunol Methods* 347, 70-78 (2009).
89. Langmead, B., Trapnell, C., Pop, M. & Salzberg, S. L. Ultrafast and memory-efficient alignment of short DNA sequences to the human genome. *Genome Biol* 10, R25 (2009).
90. Li, B. & Dewey, C. N. RSEM: accurate transcript quantification from RNA-Seq data with or without a reference genome. *BMC Bioinformatics* 12, 323 (2011).
91. Li, B., Ruotti, V., Stewart, R. M., Thomson, J. A. & Dewey, C. N. RNA-Seq gene expression estimation with read mapping uncertainty. *Bioinformatics* 26, 493-500 (2010).
92. Leng, N. et al. EBSeq: an empirical Bayes hierarchical model for inference in RNA-seq experiments. *Bioinformatics* 29, 1035-1043 (2013).
93. Moskvin, O. V., McIlwain, S. & Ong, I. M. CAMDA 2014: Making sense of RNA-Seq data: from low-level processing to functional analysis. *Systems Biomedicine* 2, 31-40 (2014).
94. Shannon, P. et al. Cytoscape: a software environment for integrated models of biomolecular interaction networks. *Genome Res* 13, 2498-2504 (2003).

The invention claimed is:

1. A method of inducing differentiation of human pluripotent stem cells into an arterial type hemogenic endothelium (AHE) cell population, comprising the steps of
   (a) differentiating pluripotent stem cells (PSCs) in a xenogen-free and serum albumin-free medium containing FGF2, BMP4, Activin A, and LiCl under hypoxic conditions for about two days to obtain a population of EMHlin−KDR+APLNR+PDGFRalpha+mesoderm cells without the formation of embryoid bodies or coculture with stromal cell lines;
   (b) culturing the population of EMHlin−KDR+APLNR+PDGFRalpha+mesoderm cells of step (a) in a medium containing FGF2 and VEGF, for about two days to obtain a population of CD144+CD43−CD73− immature hemogenic endothelial (HE) cells, and
   (c) culturing the CD144+CD43−CD73− immature HE cells of step (b) in a medium containing a sufficient amount of a NOTCH activation agent to obtain arterial hemogenic endothelial (AHE) cells, wherein the AHE cells are detected as CD144+CD43−CD73−DLL4+ HE that express EFNB2 and NOTCH1 arterial markers and MYB gene, and wherein the AHE cells have the potential to produce lympho-myeloid cells and erythrocytes with increased ratios of adult β-globin expression to embryonic ε-globin and adult β-globin expression to fetal γ-globin expression when compared to erythrocytes generated from HE cells without NOTCH activation agent.

2. The method of claim 1, further comprising the step of culturing the AHE to a sufficient amount of a NOTCH activation agent, such that the AHE undergo endothelial-to hematopoietic transition and produce lympho-myeloid and definitive erythroid progenitors.

3. The method of claim 1, wherein the NOTCH activation agent is a NOTCH ligand.

4. The method of claim 1, wherein the NOTCH activation agent is selected from the group consisting of DLL4, DLL1-Fc, DLL1-expressing feeder cell, DLL1-expressing stromal cell, DLL4-expressing feeder cell, and DLL4-expressing stromal cell.

5. The method of claim 1, wherein the NOTCH activation agent is an immobilized NOTCH ligand.

6. The method of claim 5, wherein the immobilized NOTCH ligand is plates coated with DLL4-Fc or plates coated with DLL1-Fc.

7. The method of claim 3, wherein the NOTCH ligand is DLL1-Fc.

8. The method of claim 1, wherein the pluripotent stem cells are embryonic stem cells or induced pluripotent stem cells.

9. The method of claim 2, wherein the AHE cells are differentiated into erythrocytes, wherein the erythrocytes generated from NOTCH activation have increased ratios of adult β-globin expression to embryonic ε-globin and adult β-globin expression to fetal γ-globin expression when compared to erythrocytes generated from hemogenic progenitors (HPs) without NOTCH activation.

\* \* \* \* \*

UNITED STATES PATENT AND TRADEMARK OFFICE
CERTIFICATE OF CORRECTION

PATENT NO. : 10,982,192 B2
APPLICATION NO. : 15/932317
DATED : April 20, 2021
INVENTOR(S) : Igor L. Sulkvin et al.

It is certified that error appears in the above-identified patent and that said Letters Patent is hereby corrected as shown below:

In the Specification

Column 5, Line 19, "(iPSUs) should be --(iPSCs)--.

Column 13, Lines 18-19, "$KDR^{hi}PDGFR\alpha^{hi}PDGFR\alpha^{low/-}CD31^{-}$" should be --$KDR^{hi}PDGFR\alpha^{low/-}CD31^{-}$--.

Column 13, Line 27, "culture" should be --cultures--.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 34

<210> SEQ ID NO 1
<211> LENGTH: 20
<212> TYPE: DNA
<213> ORGANISM: Artificial Sequence

```
<220> FEATURE:
<223> OTHER INFORMATION: synthetic

<400> SEQUENCE: 1
tcagtggctg acctcctctt                                                    20

<210> SEQ ID NO 2
<211> LENGTH: 20
<212> TYPE: DNA
<213> ORGANISM: Artificial Sequence
<220> FEATURE:
<223> OTHER INFORMATION: synthetic

<400> SEQUENCE: 2
cttggccttt gactgttggt                                                    20

<210> SEQ ID NO 3
<211> LENGTH: 20
<212> TYPE: DNA
<213> ORGANISM: Artificial Sequence
<220> FEATURE:
<223> OTHER INFORMATION: synthetic

<400> SEQUENCE: 3
cagtgggcag cgaagctaca                                                    20

<210> SEQ ID NO 4
<211> LENGTH: 22
<212> TYPE: DNA
<213> ORGANISM: Artificial Sequence
<220> FEATURE:
<223> OTHER INFORMATION: synthetic

<400> SEQUENCE: 4
acaggcagtg gtagccatcc tc                                                 22

<210> SEQ ID NO 5
<211> LENGTH: 21
<212> TYPE: DNA
<213> ORGANISM: Artificial Sequence
<220> FEATURE:
<223> OTHER INFORMATION: synthetic

<400> SEQUENCE: 5
ctcctcaact gtgccaaacc a                                                  21

<210> SEQ ID NO 6
<211> LENGTH: 20
<212> TYPE: DNA
<213> ORGANISM: Artificial Sequence
<220> FEATURE:
<223> OTHER INFORMATION: synthetic

<400> SEQUENCE: 6
ggttatccag gccctccaaa                                                    20

<210> SEQ ID NO 7
<211> LENGTH: 18
<212> TYPE: DNA
<213> ORGANISM: Artificial Sequence
<220> FEATURE:
<223> OTHER INFORMATION: synthetic

<400> SEQUENCE: 7
ccctaagcag cgcagcaa                                                      18
```

```
<210> SEQ ID NO 8
<211> LENGTH: 20
<212> TYPE: DNA
<213> ORGANISM: Artificial Sequence
<220> FEATURE:
<223> OTHER INFORMATION: synthetic

<400> SEQUENCE: 8
tgacttctcc tgcatgcact                                                20

<210> SEQ ID NO 9
<211> LENGTH: 20
<212> TYPE: DNA
<213> ORGANISM: Artificial Sequence
<220> FEATURE:
<223> OTHER INFORMATION: synthetic

<400> SEQUENCE: 9
gcctacctga tggacgtgct                                                20

<210> SEQ ID NO 10
<211> LENGTH: 20
<212> TYPE: DNA
<213> ORGANISM: Artificial Sequence
<220> FEATURE:
<223> OTHER INFORMATION: synthetic

<400> SEQUENCE: 10
gccggtgcgt cctttaatcc                                                20

<210> SEQ ID NO 11
<211> LENGTH: 21
<212> TYPE: DNA
<213> ORGANISM: Artificial Sequence
<220> FEATURE:
<223> OTHER INFORMATION: synthetic

<400> SEQUENCE: 11
cggtcaactt caagctccta a                                              21

<210> SEQ ID NO 12
<211> LENGTH: 18
<212> TYPE: DNA
<213> ORGANISM: Artificial Sequence
<220> FEATURE:
<223> OTHER INFORMATION: synthetic

<400> SEQUENCE: 12
gcccactcag actttatt                                                  18

<210> SEQ ID NO 13
<211> LENGTH: 18
<212> TYPE: DNA
<213> ORGANISM: Artificial Sequence
<220> FEATURE:
<223> OTHER INFORMATION: synthetic

<400> SEQUENCE: 13
ggcacctttg ccacactg                                                  18

<210> SEQ ID NO 14
<211> LENGTH: 20
<212> TYPE: DNA
<213> ORGANISM: Artificial Sequence
<220> FEATURE:
<223> OTHER INFORMATION: synthetic
```

```
<400> SEQUENCE: 14
cactggtggg gtgaattctt                                               20

<210> SEQ ID NO 15
<211> LENGTH: 20
<212> TYPE: DNA
<213> ORGANISM: Artificial Sequence
<220> FEATURE:
<223> OTHER INFORMATION: synthetic

<400> SEQUENCE: 15
gcctgtggag caagatgaat                                               20

<210> SEQ ID NO 16
<211> LENGTH: 16
<212> TYPE: DNA
<213> ORGANISM: Artificial Sequence
<220> FEATURE:
<223> OTHER INFORMATION: synthetic

<400> SEQUENCE: 16
gcgggcttga ggttgt                                                   16

<210> SEQ ID NO 17
<211> LENGTH: 21
<212> TYPE: DNA
<213> ORGANISM: Artificial Sequence
<220> FEATURE:
<223> OTHER INFORMATION: synthetic

<400> SEQUENCE: 17
cttcaagctc ctgggaaatg t                                             21

<210> SEQ ID NO 18
<211> LENGTH: 25
<212> TYPE: DNA
<213> ORGANISM: Artificial Sequence
<220> FEATURE:
<223> OTHER INFORMATION: synthetic

<400> SEQUENCE: 18
gcagaataaa gcctatcctt gaaag                                         25

<210> SEQ ID NO 19
<211> LENGTH: 18
<212> TYPE: DNA
<213> ORGANISM: Artificial Sequence
<220> FEATURE:
<223> OTHER INFORMATION: synthetic

<400> SEQUENCE: 19
cggtgaagag catcgacg                                                 18

<210> SEQ ID NO 20
<211> LENGTH: 23
<212> TYPE: DNA
<213> ORGANISM: Artificial Sequence
<220> FEATURE:
<223> OTHER INFORMATION: synthetic

<400> SEQUENCE: 20
ggatacgacc gataggaact tgt                                           23

<210> SEQ ID NO 21
```

```
<211> LENGTH: 19
<212> TYPE: DNA
<213> ORGANISM: Artificial Sequence
<220> FEATURE:
<223> OTHER INFORMATION: synthetic

<400> SEQUENCE: 21
taccccagcc agtgtcaac                                                  19

<210> SEQ ID NO 22
<211> LENGTH: 20
<212> TYPE: DNA
<213> ORGANISM: Artificial Sequence
<220> FEATURE:
<223> OTHER INFORMATION: synthetic

<400> SEQUENCE: 22
tcagctggct cagactttca                                                 20

<210> SEQ ID NO 23
<211> LENGTH: 23
<212> TYPE: DNA
<213> ORGANISM: Artificial Sequence
<220> FEATURE:
<223> OTHER INFORMATION: synthetic

<400> SEQUENCE: 23
ttcaaggcag ctcggtaact gac                                             23

<210> SEQ ID NO 24
<211> LENGTH: 23
<212> TYPE: DNA
<213> ORGANISM: Artificial Sequence
<220> FEATURE:
<223> OTHER INFORMATION: synthetic

<400> SEQUENCE: 24
catactgatg cactgctgga tgg                                             23

<210> SEQ ID NO 25
<211> LENGTH: 21
<212> TYPE: DNA
<213> ORGANISM: Artificial Sequence
<220> FEATURE:
<223> OTHER INFORMATION: synthetic

<400> SEQUENCE: 25
acggtccgaa acgttggtct g                                               21

<210> SEQ ID NO 26
<211> LENGTH: 22
<212> TYPE: DNA
<213> ORGANISM: Artificial Sequence
<220> FEATURE:
<223> OTHER INFORMATION: synthetic

<400> SEQUENCE: 26
ccccagtctc ttgtgtgcct gg                                              22

<210> SEQ ID NO 27
<211> LENGTH: 22
<212> TYPE: DNA
<213> ORGANISM: Artificial Sequence
<220> FEATURE:
<223> OTHER INFORMATION: synthetic

<400> SEQUENCE: 27
```

```
caatgtggat gccgcagttg tg                                            22

<210> SEQ ID NO 28
<211> LENGTH: 21
<212> TYPE: DNA
<213> ORGANISM: Artificial Sequence
<220> FEATURE:
<223> OTHER INFORMATION: synthetic

<400> SEQUENCE: 28
cagcaccttg gcggtctcgt a                                             21

<210> SEQ ID NO 29
<211> LENGTH: 24
<212> TYPE: DNA
<213> ORGANISM: Artificial Sequence
<220> FEATURE:
<223> OTHER INFORMATION: synthetic

<400> SEQUENCE: 29
tggttccaaa ccagtttatt ctgt                                          24

<210> SEQ ID NO 30
<211> LENGTH: 24
<212> TYPE: DNA
<213> ORGANISM: Artificial Sequence
<220> FEATURE:
<223> OTHER INFORMATION: synthetic

<400> SEQUENCE: 30
aagtgcgttt ccatcatctt tgag                                          24

<210> SEQ ID NO 31
<211> LENGTH: 23
<212> TYPE: DNA
<213> ORGANISM: Artificial Sequence
<220> FEATURE:
<223> OTHER INFORMATION: synthetic

<400> SEQUENCE: 31
cctggaggag aagaggaaag aga                                           23

<210> SEQ ID NO 32
<211> LENGTH: 25
<212> TYPE: DNA
<213> ORGANISM: Artificial Sequence
<220> FEATURE:
<223> OTHER INFORMATION: synthetic

<400> SEQUENCE: 32
ttgaggacct ctgtgtattt gtcaa                                         25

<210> SEQ ID NO 33
<211> LENGTH: 19
<212> TYPE: DNA
<213> ORGANISM: Artificial Sequence
<220> FEATURE:
<223> OTHER INFORMATION: synthetic

<400> SEQUENCE: 33
gccaagggcg agtcccgta                                                19

<210> SEQ ID NO 34
<211> LENGTH: 27
<212> TYPE: DNA
```

```
<213> ORGANISM: Artificial Sequence
<220> FEATURE:
<223> OTHER INFORMATION: synthetic

<400> SEQUENCE: 34
gcatcttgct caactcggcg ttgtgca                                              27
```